US008637658B2

(12) United States Patent
Ewing et al.

(10) Patent No.: US 8,637,658 B2
(45) Date of Patent: Jan. 28, 2014

(54) NON-FLUORESCENT QUENCHER COMPOUNDS AND BIOMOLECULAR ASSAYS

(71) Applicants: Debra Kay Ewing-Fieri, Oceanside, CA (US) Applied Biosystems, LLC, Carlsbad, CA (US)

(72) Inventors: Gregory J. Ewing, Oceanside, CA (US); Khairuzzaman Bashar Mullah, Union City, CA (US); Ronald Graham, Carlsbad, CA (US)

(73) Assignee: Applied Biosystems, LLC, Carlsbad, CA (US)

( * ) Notice: Subject to any disclaimer, the term of this patent is extended or adjusted under 35 U.S.C. 154(b) by 0 days.

(21) Appl. No.: 13/629,021

(22) Filed: Sep. 27, 2012

(65) Prior Publication Data
US 2013/0123475 A1 May 16, 2013

Related U.S. Application Data

(63) Continuation of application No. 13/363,594, filed on Feb. 1, 2012, now abandoned, which is a continuation of application No. 12/970,829, filed on Dec. 16, 2010, now abandoned, which is a continuation of application No. 12/770,641, filed on Apr. 29, 2010, now abandoned, which is a continuation of application No. 12/098,378, filed on Apr. 4, 2008, now abandoned, which is a continuation of application No. 10/897,583, filed on Jul. 23, 2004, now abandoned, which is a continuation of application No. 10/425,674, filed on Apr. 30, 2003, now abandoned, which is a continuation of application No. 09/942,342, filed on Aug. 27, 2001, now abandoned.

(51) Int. Cl.
*C07H 19/04* (2006.01)
*C07D 221/18* (2006.01)
*C12Q 1/00* (2006.01)
*A61K 38/00* (2006.01)

(52) U.S. Cl.
USPC .............. 536/26.6; 546/75; 435/4; 530/300

(58) Field of Classification Search
USPC .............. 546/75; 536/26.6; 530/300; 435/4
See application file for complete search history.

(56) References Cited

U.S. PATENT DOCUMENTS

| | | | |
|---|---|---|---|
| 2,830,943 A | 4/1958 | Mackenzie | |
| 2,945,849 A | 7/1960 | Kruckenberg et al. | |
| 3,369,013 A | 2/1968 | Weaver et al. | |
| 3,445,452 A | 5/1969 | Wallace et al. | |
| 3,709,870 A | 1/1973 | Wolfrum | |
| 4,069,012 A | 1/1978 | Heinrich | |
| 4,313,872 A | 2/1982 | Heinrich et al. | |
| 4,588,517 A | 5/1986 | Kaneko et al. | |
| 4,623,716 A | 11/1986 | Stevenson et al. | |
| 4,888,385 A | 12/1989 | Hudson | |
| 4,965,349 A | 10/1990 | Woo et al. | |
| 5,384,411 A | 1/1995 | Robotti et al. | |
| 5,538,848 A | 7/1996 | Livak et al. | |
| 5,723,591 A | 3/1998 | Livak et al. | |
| 5,736,626 A | 4/1998 | Mullah et al. | |
| 5,770,716 A | 6/1998 | Khan et al. | |
| 5,821,356 A | 10/1998 | Kahn et al. | |
| 5,846,726 A | 12/1998 | Nadeau et al. | |
| 5,866,336 A | 2/1999 | Nazarenko et al. | |
| 5,928,869 A | 7/1999 | Nadeau et al. | |
| 6,008,379 A | 12/1999 | Benson et al. | |
| 6,037,130 A | 3/2000 | Tyagi et al. | |
| 6,080,868 A | 6/2000 | Lee et al. | |
| 6,103,476 A | 8/2000 | Tyagi et al. | |
| 6,117,986 A | 9/2000 | Nardone et al. | |
| 6,150,097 A | 11/2000 | Tyagi et al. | |
| 6,727,356 B1 | 4/2004 | Reed et al. | |
| 7,019,129 B1 | 3/2006 | Cook et al. | |
| 7,109,312 B2 | 9/2006 | Cook et al. | |
| 2003/0082547 A1 | 5/2003 | Ewing et al. | |
| 2004/0005607 A1 | 1/2004 | Ewing et al. | |
| 2005/0164225 A1 | 7/2005 | Ewing et al. | |

FOREIGN PATENT DOCUMENTS

| | | |
|---|---|---|
| WO | 95/13399 | 5/1995 |
| WO | 99/64431 | 6/1999 |
| WO | 00/75378 | 12/2000 |
| WO | 01/31063 | 5/2001 |
| WO | 01/38584 | 5/2001 |
| WO | 01/42505 | 6/2001 |
| WO | 01/86001 | 11/2001 |

OTHER PUBLICATIONS

PCT International Search Report from PCT/US02/27256 dated Dec. 6, 2002.
Cardullo, R. A. et al., "Detection of Nucleic Acid Hybridization by Nomadiative Fluorescence Resonance", *Proc. Natl. Acad. Sci. USA*, vol. 85, 1988, 8790-8794.
De Angelis, D. A., "Why Fret over genomics?", *Physiol. Genomics*, vol. 1, 1999, 93-99.
Endo, H. et al., "Studies on Antitumor Activity of Phenazine Derivatives Against S 180 and C 63 in Mice (I)", *Sci. Rep. Res. Inst. Tohoku Univ. C*, vol. 12, 1965, 53-57.
Hodgkiss, R. J. et al., "Fluorescent Markers for Hypoxic Cells: A Study of Novel Heterocyclic Compounds that Undergo Bio-Reductive Binding", *Biochem. Pharmacol.*, vol. 41, 1991, 533-541.
Nazarenko, Irina A. et al., "A Closed Tube Format for Amplification and Detection of DNA Based on Energy Transfer", *Nucleic Acids Research*, vol. 25, No. 12, 1997, 2516-2521.
Sawicki, E., "Physical Properties of the Aminoazobenzene Dyes. IX. Absorption Spectra in Alcohol and Acid Solution of Disazobenzene Dyes", *J. Org. Chem.*, vol. 23, 1958, 532-535.
Wang, S.S., "p-Alkoxybenzyl Alcohol Resin and p-Alkoxybenzyloxycarbonylhydrazide Resin for Solid Phase Synthesis of Protected Peptide Fragments", *J. Am. Chem. Soc.*, vol. 95, 1973, 1328-1333.

Primary Examiner — Jezia Riley

(57) ABSTRACT

Bis-diazo, triaryl and aryldiazo-N-arylphenazonium quencher moieties, substituted with electron-withdrawing and electron-donating substituents which induce polarity in the delocalized aryl/diazo ring systems, are useful as labels when attached to biomolecules such as polynucleotides, nucleosides, nucleotides and polypeptides. The quencher moieties are non-fluorescent and accept energy transfer from fluorescent reporter labels by any energy-transfer mechanism, such as FRET.
Fluorescence quencher compositions are useful in preparing quencher labeled biomolecules for various molecular biology assays based on fluorescence detection.

29 Claims, No Drawings

NON-FLUORESCENT QUENCHER COMPOUNDS AND BIOMOLECULAR ASSAYS

I. CROSS REFERENCE TO RELATED APPLICATION(S)

This application is a continuation of U.S. application Ser. No. 13/363,594, filed Feb. 1, 2012, which is a continuation of U.S. application Ser. No. 12/970,829, filed Dec. 16, 2010 (now abandoned), which is a continuation of U.S. application Ser. No. 12/770,641, filed Apr. 29, 2010 (now abandoned), which is a continuation of U.S. application Ser. No. 12/098,378, filed Apr. 4, 2008 (now abandoned), which is a continuation of U.S. application Ser. No. 10/897,583, filed Jul. 23, 2004 (now abandoned), which is a continuation of U.S. application Ser. No. 10/425,674, filed Apr. 30, 2004 (now abandoned), which is a continuation of application Ser. No. 09/942,342, filed Aug. 27, 2001 (now abandoned), the disclosure of which is hereby incorporated by reference in its entirety.

II. FIELD OF THE INVENTION

This invention relates generally to the field of molecular biology and more particularly, to methods and reagents of biomolecular detection and fluorescence-based assays.

III. INTRODUCTION

Researchers use fluorescence quenching biomolecular assays to detect the interaction, assembly, cleavage, dissociation and conformations of proteins, nucleic acids, and other biomolecules. Fluorescence resonance energy transfer (FRET) is an important technique for investigating a variety of biological phenomena that produce changes in molecular proximity, conformation, and bond formation and cleavage. FRET has been applied in detection of labelled biomolecules to important areas of genomics: identification of single-nucleotide polymorphisms and other allelic variants, protein-protein interactions, and genome-wide analysis of regulatory sequences. Genetic information is being rapidly gleaned by automated sequencing of genomes from all kinds of organisms. As this information becomes available, functions are sought for individual gene products, factors that influence the expression level of these gene products will be identified; and allelic variants that act alone or in combination to give rise to complex traits will be characterized. Because of the size and number of genomes of interest, methods and reagents that can streamline or automate these processes are highly desirable. Fluorescence is an attractive readout for such high-throughput tasks because of the availability of instruments, reagents, methods, and software which are designed to detect light-emitting compounds with great speed, accuracy and at high throughput (De Angelis, D. (1999) Physiol. Genomics 1:93-99).

Fluorescent quenching acceptors, e.g. TAMRA (tetramethylrhodamine), have been employed in FRET assays, but have at least two significant limitations: background fluorescence and the preclusion of detection of reporter fluorescence at the acceptor fluorescence emission. For example, the emission maxima at about 582 nm of TAMRA-labelled oligonucleotide probes hinders the use of reporter dyes with comparable emission maxima. There is a need for non-fluorescent quencher compositions for FRET assays with reporter dyes that fluoresce above about 550 nm. Reporter dyes with absorption maximum at wavelengths at about 600 nm allow for the use of cheaper He—Ne lasers.

IV. SUMMARY OF THE INVENTION

The present invention provides bis-diazo,triaryl I and aryldiazo-N-arylphenazonium II compounds which are useful as quencher labels when attached to biomolecules such as polynucleotides, nucleosides, nucleotides, carbohydrates, and polypeptides.

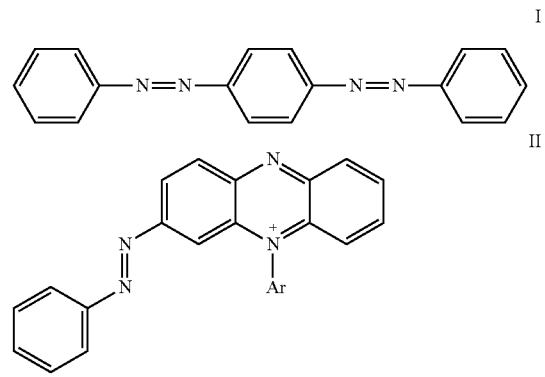

In one aspect of the invention, the fluorescence quencher compositions have structure III:

Y is N or CR, where R is H, $C_1$-$C_6$ alkyl or $C_5$-$C_{14}$ aryl. $L_1$, $L_2$, and $L_3$ are each, independently, a bond, or a linker such as $C_1$-$C_{12}$ alkyldiyl, $C_1$-$C_{12}$ alkoxydiyl, $C_1$-$C_{12}$ alkylaminodiyl, $C_1$-$C_{12}$ alkylamidediyl, $C_5$-$C_{14}$ aryldiyl, and 1-20 ethyleneoxy units.

X is a biomolecule such as an amino acid, a polypeptide, a nucleoside, a nucleotide, a polynucleotide, or protected form thereof; or X may be an acid-labile protecting group which can be removed to form a reactive linking group which can form an attachment to a biomolecule.

Z is a reactive linking group to form attachments to biomolecules and labels, a solid support, or a label.

Q is a bis-diazo,triaryl quencher moiety I or aryldiazo-N-arylphenazonium quencher moiety II. One of the aryl carbons of a quencher moiety, Q, is attached to linker $L_1$. At least one aryl carbon of the quencher moiety is substituted with an electron-withdrawing group, and at least one aryl carbon of a quencher moiety is substituted with an electron-donating group. The electron-withdrawing group may be on the same or different aryl ring as the electron-donating group.

Other aspects of the invention include compositions comprising nucleosides, nucleotides, polynucleotides, or polypeptides labelled with the bis-diazo,triaryl and aryldiazo-N-arylphenazonium quencher moieties. The quencher labelled biomolecules may further contain fluorescent reporter moieties which form energy transfer pairs.

Other aspects of the invention include methods of labelling polynucleotides and polypeptides with the bis-diazo,triaryl and aryldiazo-N-arylphenazonium quencher moieties of the invention. For example, polynucleotides can be labelled at the 3' terminus with fluorescence quencher solid support compositions. Polynucleotides can be labelled at the 5' terminus with fluorescence quencher phosphoramidite compositions.

Another aspect of the invention are methods of primer extension where a polynucleotide primer is annealed to a target polynucleotide and extended by polymerase-mediated incorporation of a nucleotide 5'-triphosphate. The primer or a nucleotide 5'-triphosphate may be labelled with a quencher moiety of the invention. The 3' terminus of the quencher labelled nucleotide may be modified to terminate primer extension. The resulting extension fragments may be separated and analyzed.

Embodiments of primer extension methods include nucleic acid amplification. A target polynucleotide may be amplified by the polymerase chain reaction, or other nucleic acid amplification method, with nucleotide 5'-triphosphates, a polymerase, and two or more primers. In one embodiment, a primer is labelled with a quencher moiety of the invention. In another embodiment, a nucleotide 5'-triphosphate is labelled with a quencher moiety of the invention. A detectable probe may be labelled with a fluorescent dye and a quencher moiety. Hybridization to the target polynucleotide may be monitored by FRET and used to detect the target sequence. The probe may be cleaved by nuclease activity of an enzyme during nucleic acid amplification. Cleavage may generate a detectable signal and used to monitor and detect nucleic acid hybridization and amplification. The primers and probes may be further labelled with hybridization-stabilizing moieties, such as minor groove binders.

Another embodiment of primer extension is a method of fragment analysis where polynucleotide fragments are formed by polymerase-directed primer extension of a primer. The primer can be labelled with a quencher moiety of the invention. The fragments are resolved, i.e. separated, and detected.

Another aspect of the invention is a method of oligonucleotide ligation. A probe labelled with a quencher moiety is hybridized to a complementary sequence, and adjacent to another probe labelled with a fluorescent reporter. Ligation may be performed with a ligase, generating a polynucleotide bearing the quencher moiety and the fluorescent reporter which interact to give a detectable fluorescent change.

Another aspect of the invention includes a method for hybridization detection. In one embodiment, a probe labelled with a fluorescent dye and a quencher moiety of the invention is annealed to a target polynucleotide sequence and a signal is detected from the fluorescent dye.

The invention further includes kits of reagents for performing the methods and uses detailed herein. The kits may contain the fluorescence quencher compositions, biomolecules labelled with the quencher moieties, and/or other reagents.

V. DETAILED DESCRIPTION

Reference will now be made in detail to certain embodiments of the invention, examples of which are illustrated in the accompanying Examples. While the invention will be described in conjunction with the exemplary embodiments, it will be understood that they are not intended to limit the invention to those embodiments. On the contrary, the invention is intended to cover all alternatives, modifications, and equivalents, which may be included within the scope of the claimed invention.

V.1 DEFINITIONS

"Biomolecule" means an amino acid, a polypeptide, a nucleoside, a nucleotide, a polynucleotide, a carbohydrate, a vitamin, a hormone, and any other compound produced by an organism.

"Nucleobase" means any nitrogen-containing heterocyclic moiety capable of forming Watson-Crick hydrogen bonds in pairing with a complementary nucleobase or nucleobase analog, e.g. a purine, a 7-deazapurine, or a pyrimidine. Typical nucleobases are the naturally occurring nucleobases adenine, guanine, cytosine, uracil, thymine, and analogs of the naturally occurring nucleobases, e.g. 7-deazaadenine, 7-deazaguanine, 7-deaza-8-azaguanine, 7-deaza-8-azaadenine, inosine, nebularine, nitropyrrole, nitroindole, 2-aminopurine, 2-amino-6-chloropurine, 2,6-diaminopurine, hypoxanthine, pseudouridine, pseudocytosine, pseudoisocytosine, 5-propynylcytosine, isocytosine, isoguanine, 7-deazaguanine, 2-thiopyrimidine, 6-thioguanine, 4-thiothymine, 4-thiouracil, $O^6$-methylguanine, $N^6$-methyladenine, $O^4$-methylthymine, 5,6-dihydrothymine, 5,6-dihydrouracil, 4-methylindole, pyrazolo[3,4-D]pyrimidines (U.S. Pat. Nos. 6,143,877 and 6,127,121; WO 01/38584), and ethenoadenine (Fasman (1989) in *Practical Handbook of Biochemistry and Molecular Biology*, pp. 385-394, CRC Press, Boca Raton, Fla.).

"Nucleoside" refers to a compound consisting of a nucleobase linked to the C-1' carbon of a sugar, such as ribose, arabinose, xylose, and pyranose. The sugar may be substituted or unsubstituted. Substituted ribose sugars include, but are not limited to, those riboses in which one or more of the carbon atoms, for example the 2'-carbon atom, is substituted with one or more of the same or different Cl, F, —R, —OR, —NR$_2$ or halogen groups, where each R is independently H, $C_1$-$C_6$ alkyl or $C_5$-$C_{14}$ aryl. Ribose examples include ribose, 2'-deoxyribose, 2',3'-dideoxyribose, 2'-haloribose, 2'-fluororibose, 2'-chlororibose, and 2'-alkylribose, e.g. 2'-O-methyl, 4'-α-anomeric nucleotides, 1'-α-anomeric nucleotides, 2'-4'- and 3'-4'-linked and other "locked" or "LNA", bicyclic sugar modifications (WO 98/22489; WO 98/39352; WO 99/14226). Exemplary LNA sugar analogs within a polynucleotide include the structures:

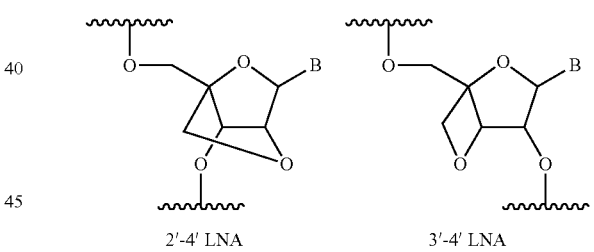

2'-4' LNA     3'-4' LNA where B is any nucleobase.

Modifications at the 2'- or 3'-position of ribose include hydrogen, hydroxy, methoxy, ethoxy, allyloxy, isopropoxy, butoxy, isobutoxy, methoxyethyl, alkoxy, phenoxy, azido, amino, alkylamino, fluoro, chloro and bromo. Nucleosides and nucleotides include the natural D optical isomer, as well as the L optical isomer forms (Garbesi (1993) Nucl. Acids Res. 21:4159-65; Fujimori (1990) J. Amer. Chem. Soc. 112:7435; Urata, (1993) Nucleic Acids Symposium Ser. No. 29:69-70). When the nucleobase is purine, e.g. A or G, the ribose sugar is attached to the $N^9$-position of the nucleobase. When the nucleobase is pyrimidine, e.g. C, T or U, the pentose sugar is attached to the $N^1$-position of the nucleobase (Kornberg and Baker, (1992) *DNA Replication*, 2$^{nd}$ Ed., Freeman, San Francisco, Calif.).

"Nucleotide" refers to a phosphate ester of a nucleoside, as a monomer unit or within a nucleic acid. "Nucleotide 5'-triphosphate" refers to a nucleotide with a triphosphate ester group at the 5' position, and are sometimes denoted as "NTP", or "dNTP" and "ddNTP" to particularly point out the structural features of the ribose sugar. The triphosphate ester group may include sulfur substitutions for the various oxygens, e.g. α-thio-nucleotide 5'-triphosphates. For a review of nucleic acid chemistry, see: Shabarova, Z. and Bogdanov, A. *Advanced Organic Chemistry of Nucleic Acids*, VCH, New York, 1994.

As used herein, the terms "polynucleotide" and "oligonucleotide" are used interchangeably and mean single-stranded and double-stranded polymers of nucleotide monomers, including 2'-deoxyribonucleotides (DNA) and ribonucleotides (RNA) linked by internucleotide phosphodiester bond linkages, or internucleotide analogs, and associated counter ions, e.g., $H^+$, $NH_4^+$, trialkylammonium, $Mg^{2+}$, $Na^+$ and the like. A polynucleotide may be composed entirely of deoxyribonucleotides, entirely of ribonucleotides, or chimeric mixtures thereof. Polynucleotides may be comprised of nucleobase and sugar analogs. Polynucleotides typically range in size from a few monomeric units, e.g. 5-40 when they are more commonly frequently referred to in the art as oligonucleotides, to several thousands of monomeric nucleotide units. Unless denoted otherwise, whenever a polynucleotide sequence is represented, it will be understood that the nucleotides are in 5' to 3' order from left to right and that "A" denotes deoxyadenosine, "C" denotes deoxycytidine, "G" denotes deoxyguanosine, and "T" denotes thymidine, unless otherwise noted.

"Internucleotide analog" means a phosphate ester analog or a non-phosphate analog of a polynucleotide. Phosphate ester analogs include: (i) $C_1$-$C_4$ alkylphosphonate, e.g. methylphosphonate; (ii) phosphoramidate; (iii) $C_1$-$C_6$ alkyl-phosphotriester; (iv) phosphorothioate; and (v) phosphorodithioate. Non-phosphate analogs include compounds wherein the sugar/phosphate moieties are replaced by an amide linkage, such as a 2-aminoethylglycine unit, commonly referred to as PNA (Buchardt, WO 92/20702; Nielsen (1991) Science 254: 1497-1500).

"Polypeptide" refers to a polymer including proteins, synthetic peptides, antibodies, peptide analogs, and peptidomimetics in which the monomers are amino acids and are joined together through amide bonds. When the amino acids are α-amino acids, either the L-optical isomer or the D-optical isomer can be used. Additionally, unnatural amino acids, for example, valanine, phenylglycine and homoarginine are also included. Commonly encountered amino acids that are not gene-encoded may also be used in the present invention. All of the amino acids used in the present invention may be either the D- or L-optical isomer. In addition, other peptidomimetics are also useful in the present invention. For a general review, see Spatola, A. F., in *Chemistry and Biochemistry of Amino Acids, Peptides and Proteins*, B. Weinstein, eds., Marcel Dekker, New York, p. 267 (1983). The term "amino acid" refers to naturally occurring and synthetic amino acids, as well as amino acid analogs and amino acid mimetics that function in a manner choices can be found in many art recognized references.

"Attachment site" refers to a site on a moiety or a molecule, e.g. a quencher, a fluorescent dye, a polynucleotide, or a PNA, to which is covalently attached, or capable of being covalently attached, a linker or another moiety.

"Linker" refers to a chemical moiety in a molecule comprising a covalent bond or a chain of atoms that covalently attaches one moiety or molecule to another, e.g. a quencher to a polynucleotide. A "cleavable linker" is a linker which has one or more covalent bonds which may be broken by the result of a reaction or condition. For example, an ester in a molecule is a linker that may be cleaved by a reagent, e.g. sodium hydroxide, resulting in a carboxylate-containing fragment and a hydroxyl-containing product "Reactive linking group" refers to a chemically reactive substituent or moiety, e.g. a nucleophile or electrophile, on a molecule which is capable of reacting with another molecule to form a covalent bond. Reactive linking groups include active esters, which are commonly used for coupling with amine groups. For example, N-hydroxysuccinimide (NHS) esters have selectivity toward aliphatic amines to form aliphatic amide products which are very stable. Their reaction rate with aromatic amines, alcohols, phenols (tyrosine), and histidine is relatively low. Reaction of NHS esters with amines under nonaqueous conditions is facile, so they are useful for derivatization of small peptides and other low molecular weight biomolecules. Virtually any molecule that contains a carboxylic acid or that can be chemically modified to contain a carboxylic acid can be converted into its NHS ester. NHS esters are available with sulfonate groups that have improved water solubility.

"Substituted" as used herein refers to a molecule wherein one or more hydrogen atoms are replaced with one or more non-hydrogen atoms, functional groups or moieties. For example, an unsubstituted nitrogen is —$NH_2$, While a substituted nitrogen is —$NHCH_3$. Exemplary substituents include but are not limited to halo, e.g., fluorine and chlorine, $C_1$-$C_8$ alkyl, sulfate, sulfonate, sulfone, amino, ammonium, amido, nitrile, nitro, alkoxy (—OR where R is $C_1$-$C_{12}$ alkyl), phenoxy, aromatic, phenyl, polycyclic aromatic, heterocycle, water-solubilizing group, and linking moiety.

"Alkyl" means a saturated or unsaturated, branched, straight-chain, branched, cyclic, or substituted hydrocarbon radical derived by the removal of one hydrogen atom from a single carbon atom of a parent alkane, alkene, or alkyne. Typical alkyl groups consist of 1-12 saturated and/or unsaturated carbons, including, but not limited to, methyl, ethyl, cyanoethyl, isopropyl, butyl, and the like.

"Alkyldiyl" means a saturated or unsaturated, branched, straight chain, cyclic, or substituted hydrocarbon radical of 1-12 carbon atoms, and having two monovalent radical centers derived by the removal of two hydrogen atoms from the same or two different carbon atoms of a parent alkane, alkene or alkyne. Typical alkyldiyl radicals include, but are not limited to, 1,2-ethyldiyl (—$CH_2CH_2$—), 1,3-propyldiyl (—$CH_2CH_2CH_2$—), 1,4-butyldiyl (—$CH_2CH_2CH_2CH_2$—), and the like. "Alkoxydiyl" means an alkoxyl group having two monovalent radical centers derived by the removal of a hydrogen atom from the oxygen and a second radical derived by the removal of a hydrogen atom from a carbon atom. Typical alkoxydiyl radicals include, but are not limited to, methoxydiyl (—$OCH_2$—) and 1,2-ethoxydiyl or ethyleneoxy (—$OCH_2CH_2$—). "Alkylaminodiyl" means an alkylamino group having two monovalent radical centers derived by the removal of a hydrogen atom from the nitrogen and a second radical derived by the removal of a hydrogen atom from a carbon atom. Typical alkylaminodiyl radicals include, but are not limited to —$NHCH_2$—, —$NHCH_2CH_2$—, and —$NHCH_2CH_2CH_2$—. "Alkylamidediyl" means an alkylamide group having two monovalent radical centers derived by the removal of a hydrogen atom from the nitrogen and a second radical derived by the removal of a hydrogen atom from a carbon atom. Typical alkylamidediyl radicals include, but are not limited to —$NHC(O)CH_2$—, —$NHC(O)CH_2CH_2$—, and —$NHC(O)CH_2CH_2CH_2$—.

"Aryl" means a monovalent aromatic hydrocarbon radical of 5-14 carbon atoms derived by the removal of one hydrogen atom from a single carbon atom of a parent aromatic ring system. Typical aryl groups include, but are not limited to, radicals derived from benzene, substituted benzene, naphthalene, anthracene, biphenyl, and the like, including substituted aryl groups.

"Aryl carbon" means any carbon atom part of an aromatic ring system.

"Aryldiyl" means an unsaturated cyclic or polycyclic hydrocarbon radical of 5-14 carbon atoms having a conjugated resonance electron system and at least two monovalent radical centers derived by the removal of two hydrogen atoms from two different carbon atoms of a parent aryl compound, including substituted aryldiyl groups.

"Substituted alkyl", "substituted alkyldiyl", "substituted aryl" and "substituted aryldiyl" mean alkyl, alkyldiyl, aryl and aryldiyl respectively, in which one or more hydrogen atoms are each independently replaced with another substituent. Typical substituents include, but are not limited to, F, Cl, Br, I, R, OH, —OR, —SR, SH, $NH_2$, NHR, $NR_2$, —$^+NR_3$, —N=$NR_2$, —$CX_3$, —CN, —OCN, —SCN, —NCO, —NCS, —NO, —$NO_2$, —$N_2^+$, —$N_3$, —NHC(O)R, —C(O)R, —C(O)$NR_2$—S(O)$_2$O$^-$, —S(O)$_2$R, —OS(O)$_2$OR, —S(O)$_2$ NR, —S(O)R, —OP(O)(OR)$_2$, —P(O)(OR)$_2$, —P(O)(O$^-$)$_2$, —P(O)(OH)$_2$, —C(O)R, —C(O)X, —C(S)R, —C(O)OR, —CO$_2^-$, —C(S)OR, —C(O)SR, —C(S)SR, —C(O)$NR_2$, —C(S)$NR_2$, —C(NR)$NR_2$, where each R is independently —H, $C_1$-$C_6$ alkyl, $C_5$-$C_{14}$ aryl, heterocycle, or linking group: Substituents also include divalent, bridging functionality, such as diazo (—N=N—), ester, ether, ketone, phosphate, alkyldiyl, and aryldiyl groups.

"Electron-donating group" means a functional group that donates electron density into a bond or delocalized resonance system, and includes: O$^-$, S$^-$, $NR_2$, NHR, $NH_2$, —NHC(O)R, —OR, OH, —OC(O)R, —SR, SH, Br, I, Cl, F, R, and $C_5$-$C_{14}$ aryl, where R is $C_1$-$C_{12}$ alkyl.

"Electron-withdrawing group" means a functional group that removes electron density into a bond or delocalized resonance system, and includes: $NO_2$, CN, $CO_2$H, $CO_2$R, C(O)$NH_2$, C(O)NHR, C(O)$NR_2$, CHO, C(O)R, $SO_2$R, $SO_2$OR, NO, and $C_5$-$C_{14}$ aryl, where R is $C_1$-$C_{12}$ alkyl (J. March (1985) *Advanced Organic Chemistry*, Third Ed., John Wiley & Sons, New York, p. 238).

"Heterocycle" refers to a molecule with a ring system in which one or more ring atoms is a heteroatom, e.g. nitrogen, oxygen, and sulfur (as opposed to carbon).

"Enzymatically extendable" refers to a nucleotide which is: (i) capable of being enzymatically incorporated onto the terminus of a polynucleotide chain through the action of a polymerase enzyme, and (ii) capable of supporting further primer extension. Enzymatically extendable nucleotides include nucleotide 5'-triphosphates, i.e. dNTP and NTP.

"Enzymatically incorporatable" refers to a nucleotide which is capable of being enzymatically incorporated onto the terminus of a polynucleotide chain through the action of a polymerase enzyme. Enzymatically incorporatable nucleotides include dNTP, NTP, and 2',3'-dideoxy, nucleotide 5'-triphosphates, i.e. ddNTP.

"Target sequence" means a polynucleotide sequence that is the subject of hybridization with a complementary polynucleotide, e.g. a primer or probe. The target sequence can be composed of DNA, RNA, an analog thereof, and including combinations thereof.

The term "probe" means a polynucleotide that is capable of forming a duplex structure by complementary base pairing with a sequence of a target nucleic acid. For example, probes may be labelled, e.g. with a quencher moiety, or an energy transfer pair comprised of a fluorescent reporter and quencher.

The term "label" refers to any moiety which can be attached to a molecule and: (i) provides a detectable signal; (ii) interacts with a second label to modify the detectable signal provided by the second label, e.g. FRET; (iii) stabilizes hybridization, i.e. duplex formation; or (iv) provides a capture moiety, i.e. affinity, antibody/antigen, ionic complexation. Labelling can be accomplished using any one of a large number of known techniques employing known labels, linkages, linking groups, reagents, reaction conditions, and analysis and purification methods. Labels include light-emitting or light-absorbing compounds which generate or quench a detectable fluorescent, chemiluminescent, or bioluminescent signal (Kricka, L. in *Nonisotopic DNA Probe Techniques* (1992), Academic Press, San Diego, pp. 3-28). Fluorescent reporter dyes useful for labelling biomolecules include fluoresceins (U.S. Pat. Nos. 5,188,934; 6,008,379; 6,020,481), rhodamines (U.S. Pat. Nos. 5,366,860; 5,847,162; 5,936,087; 6,051,719; 6,191,278), benzophenoxazines (U.S. Pat. No. 6,140,500), energy-transfer dye pairs of donors and acceptors (U.S. Pat. Nos. 5,863,727; 5,800,996; 5,945,526), and cyanines (Kubista, WO 97/45539), as well as any other fluorescent label capable of generating a detectable signal. Examples of fluorescein dyes include 6-carboxyfluorescein; 2',4',1,4,-tetrachlorofluorescein; and 2',4',5',7',1,4-hexachlorofluorescein. See Example 50 and Menchen, U.S. Pat. No. 5,118,934.

Another class of labels are hybridization-stabilizing moieties which serve to enhance, stabilize, or influence hybridization of duplexes, e.g. intercalators, minor-groove binders, and cross-linking functional groups (Blackburn, G. and Gait, M. Eds. "DNA and RNA structure" in *Nucleic Acids in Chemistry and Biology*, 2$^{nd}$ Edition, (1996) Oxford University Press, pp. 15-81). Yet another class of labels effect the separation or immobilization of a molecule by specific or non-specific capture, for example biotin, digoxigenin, and other haptens (Andrus, A. "Chemical methods for 5' non-isotopic labelling of PCR probes and primers" (1995) in *PCR 2: A Practical Approach*, Oxford University Press, Oxford, pp. 39-54). Non-radioactive labelling methods, techniques, and reagents are reviewed in: *Non-Radioactive Labelling, A Practical Introduction*, Garman, A. J. (1997) Academic Press, San Diego.

As used herein, "energy transfer" refers to the process by which the excited state energy of an excited group, e.g. fluorescent reporter dye, is conveyed through space or through bonds to another group, e.g. a quencher moiety, which may attenuate (quench) or otherwise dissipate or transfer the energy. Energy transfer can occur through fluorescence resonance energy transfer, direct energy transfer, and other mechanisms. The exact energy transfer mechanisms is not limiting to the present invention. It is to be understood that any reference to energy transfer in the instant application encompasses all of these mechanistically-distinct phenomena.

"Energy transfer pair" refers to any two moieties that participate in energy transfer. Typically, one of the moieties acts as a fluorescent reporter, i.e. donor, and the other acts as a fluorescence quencher, i.e. acceptor ("Fluorescence resonance energy transfer." Selvin P. (1995) Methods Enzymol 246:300-334; dos Remedios C. G. (1995) J. Struct. Biol. 115:175-185; "Resonance energy transfer: methods and applications." Wu P. and Brand L. (1994) Anal Biochem 218:1-13). Fluorescence resonance energy transfer (FRET) is a distance-dependent interaction between two moieties in which excitation energy, i.e. light, is transferred from a donor ("reporter") to an acceptor without emission of a photon. The acceptor may be fluorescent and emit the transferred energy at a longer wavelength, or it may be non-fluorescent and serve to diminish the detectable fluorescence of the reporter (quenching). FRET may be either an intermolecular or intramolecular event, and is dependent on the inverse sixth power of the separation of the donor and acceptor, making it useful over distances comparable with the dimensions of biological macromolecules. Thus, the spectral properties of the energy transfer pair as a whole change in some measurable way if the distance between the moieties is altered by some critical amount. Self-quenching probes incorporating fluorescent donor-nonfluorescent acceptor combinations have been developed primarily for detection of proteolysis (Matayoshi, (1990) Science 247:954-958) and nucleic acid hybridization ("Detection of Energy Transfer and Fluorescence Quenching" Morrison, L., in *Nonisotopic DNA Probe Techniques*, L. Kricka, Ed., Academic Press, San Diego, (1992) pp. 311-352; Tyagi S. (1998) Nat. Biotechnol. 16:49-53; Tyagi S. (1996) Nat. Biotechnol 14:303-308). In most applications, the donor and acceptor dyes are different, in which case FRET can be detected by the appearance of sensitized fluorescence of the acceptor or by quenching of donor fluorescence.

The term "quenching" refers to a decrease in fluorescence of a fluorescent reporter moiety caused by a quencher moiety by energy transfer, regardless of the mechanism. Hence, illumination of the fluorescent reporter in the presence of the quencher leads to an emission signal that is less intense than expected, or even completely absent.

"Chimera" as used herein refers to a polynucleotide including one or more modification or analog to a sugar, a nucleobase, or an internucleotide linkage.

The terms "annealing" and "hybridization" are used interchangeably and mean the base-pairing interaction of one nucleic acid with another nucleic acid that results in formation of a duplex or other higher-ordered structure. The primary interaction is base specific, i.e. A/T and G/C, by Watson/Crick and Hoogsteen-type hydrogen bonding.

The term "solid support" refers to any solid phase material upon which a nucleic acid or polypeptide is synthesized, attached or immobilized. Solid support encompasses terms such as "resin", "solid phase", and "support". A solid support may be composed of organic polymers such as polystyrene, polyethylene, polypropylene, polyfluoroethylene, polyethyleneoxy, and polyacrylamide, as well as co-polymers and grafts thereof. A solid support may also be inorganic, such as glass, silica, controlled-pore-glass (CPG), or reverse-phase silica. The configuration of a solid support may be in the form of beads, spheres, particles, granules, or a surface. Surfaces may be planar, substantially planar, or non-planar. Solid supports may be porous or non-porous, and may have swelling or non-swelling characteristics. A solid support may be configured in the form of a well, depression or other vessel. A plurality of solid supports may be configured in an array, addressable for robotic delivery of reagents, or by detection means including scanning by laser illumination and confocal or deflective light gathering.

"Array" means a predetermined spatial arrangement of polynucleotides present on a solid support or in an arrangement of vessels.

The term "end-point analysis" refers to a method where data collection occurs only when a reaction is substantially complete.

The term "real-time analysis" refers to periodic monitoring during PCR. Certain systems such as the ABI 7700 and 7900HT Sequence Detection Systems (Applied Biosystems, Foster City, Calif.) conduct monitoring during each thermal cycle at a pre-determined or user-defined point. Real-time analysis of PCR with FRET probes measures fluorescent dye signal changes from cycle-to-cycle, preferably minus any internal control signals.

V.2 FLUORESCENCE QUENCHER COMPOSITIONS

Novel compositions including quencher moieties are disclosed which are used to conduct, or are used to prepare other novel compositions which conduct, fluorescence-based biomolecular assays and methods. When attached to biomolecules such as polynucleotides, nucleotides, nucleosides, and polypeptides, quencher moieties of the invention undergo efficient energy transfer with fluorescent dyes. The fluorescent dyes may be: (1) attached to the same biomolecule (intramolecular), or (2) attached to another biomolecule or reagent (intermolecular), which is free in solution or bound to a solid support. A quencher moiety can be matched with one or more fluorescent reporters to form an energy transfer pair, based on spectral overlap and other spectral properties. Typically, the fluorescent reporter in an energy transfer pair will have a longer wavelength absorbance or excitation maximum than the absorbance maximum of the quencher moiety. The quencher moieties of the invention include bis-diazo, triaryl structure I:

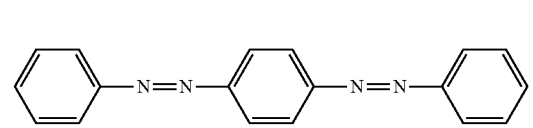

and aryldiazo-N-arylphenazonium structure II:

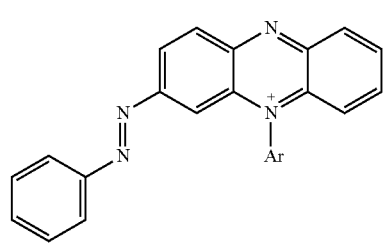

Various counterions may be associated with charged structures I and II. Ar in structure II is a $C_5$-$C_{14}$ aryl group, such as phenyl or substituted phenyl. One of the aryl carbons in each of I and II is the site of a covalent attachment, e.g. to the linker, $L_1$ of structure III.

Structures I and II have extended aromaticity for efficient spectral overlap with longer wavelength (redder) fluorescent dye reporters. Quencher moieties of the invention have broad absorbance above 500 nm and enable energy transfer of fluorescence emitted from fluorescent dyes in the range of about 500-700 nm. Quenchers of the invention also have the surprising and beneficial properties of non-fluorescence and accept energy from fluorescent reporter labels by an energy-transfer mechanism. Quencher moieties of the invention are effective at quenching reporter dyes across a broad spectra of fluorescence detection, especially at longer wavelengths, and eliminate problems of background fluorescence resulting from direct (i.e. nonsensitized) acceptor excitation (Lee, U.S. Pat. No. 6,080,868; Reed, WO 01/42505; Cook, WO 00/75378). Quencher moieties of the invention also have the surprising and unexpected properties of: ease and efficiency of preparation and purification, good chemical stability, good water-solubility, and efficient labelling of biomolecules.

The quencher moieties of the present invention are substituted with electron-withdrawing and electron-donating substituents which induce polarity in the delocalized aryl/diazo ring systems. In an unexpected discovery, it was found that when the aryl carbons of structures I and II were substituted with combinations of electron-withdrawing and electron-donating groups, efficient quenching of fluorescent dyes was attained. At least one aryl carbon of structures I and II is substituted with an electron-withdrawing group, and at least one aryl carbon of structures I and II is substituted with an electron-donating group. The electron-withdrawing group may be on the same or different aryl ring as the electron-donating group.

Electron-withdrawing groups are selected from $NO_2$, $CN$, $CF_3$, $CO_2H$, $CO_2R$, $CONH_2$, $CONHR$, $CONR_2$, $CHO$, $C(O)R$, $SO_2R$, $SO_2OR$, $SO_2CF_3$, $SO_3H$, $NO$, and $C_5$-$C_{14}$ aryl, where R is H, $C_1$-$C_{12}$ alkyl or $C_5$-$C_{14}$ aryl. Electron-donating groups are selected from $O^-$, $S^-$, $NR_2$, $NHR$, $NH_2$, $NHCOR$, $OR$, $OH$, $OCOR$, $SR$, $SH$, $Br$, $I$, $Cl$, $F$, $C_1$-$C_{12}$ alkyl, and $C_5$-$C_{14}$ aryl, where R is H, $C_1$-$C_{12}$ alkyl or $C_5$-$C_{14}$ aryl.

The electron-withdrawing and electron-donating groups on the aryl carbons of the aromatic rings of I and II may be in any configuration, i.e. ortho, meta, or para to the diazo group.

Procedures for the preparation of monocyclic (Examples 1-7) and bicyclic (Examples 8-27) precursors are detailed therein. The synthesis of bis-diazo, triaryl structures I from these precursors and from commercially available reagents are detailed in Examples 28-40. An exemplary synthesis of aryldiazo-N-arylphenazonium structures II is detailed in Example 41. Diazonium coupling reactions to form the aryl diazo compounds are typical electrophilic aromatic substitutions (J. McMurry in *Organic Chemistry, Fifth Edition*, Brooks/Cole, Pacific Grove, Calif., pp 1006-07). Compounds of the present invention may be prepared by reacting aryl compounds substituted with electron-donating groups and aryl diazonium compounds. The diazonium compounds may be purchased from commercial sources or prepared by diazotization of aryl amines with diazotizing reagents such as $NaNO_2$/HCl, nitrosylsulfuric acid, and nitrosonium tetrafluoroborate. The diazonium compounds can be isolated or used in situ by the subsequent addition of the aryl compound substituted with one or more electron-donating group such as an alkylamine or alkoxy group, e.g. methoxy. The compounds described in the Examples (1-88) may be prepared by other known reactions, using routes known in the art, or from other commercial sources. For a general review of azo dye chemistry, see: Zollinger, H. *Color Chemistry*; VCH, New York, 1987.

A fluorescence quencher composition of the invention may have structure III:

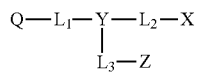

III

Y may be N or CR, where R is H, $C_1$-$C_6$ alkyl or $C_5$-$C_{14}$ aryl. The linkers, $L_1$, $L_2$, and $L_3$, are independently selected from a bond, $C_1$-$C_{12}$ alkyldiyl, $C_1$-$C_{12}$ alkoxyldiyl, $C_1$-$C_{12}$ alkylaminodiyl, $C_1$-$C_{12}$ alkylamidediyl, $C_5$-$C_{14}$ aryldiyl, and 1-20 ethyleneoxy units. X is an amino acid, a polypeptide, a nucleoside, a nucleotide, a polynucleotide, and protected forms thereof; or an acid-labile protecting group, e.g. 4,4'-dimethoxytrityl (DMT), 4-monomethoxytrityl (MMT), trityl, substituted trityl, 9-phenylxanthen-9-yl (pixyl), and trialkylsilyl (Beaucage (1992) Tetrahedron 48:2223-2311 at 2233-2242). Z is selected from H, $CO_2H$, $OH$, $NH_2$, $NHR$, $NR_2$, $SH$, an ester, a cleavable linker, a solid support, a reactive linking group, and a label selected from a fluorescent dye, a hybridization-stabilizing moiety, a chemiluminescent dye, and an affinity ligand. Q is selected from the diazo structures I and II.

Z may be any ester, such as an oxalate, phenoxymethyl, quinone, diglycolate, succinate, or allyloxycarbonyl. Z may be selected from the structures:

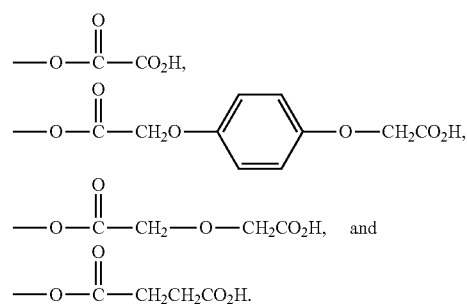

Exemplary embodiments of fluorescence quencher compositions include the structures:

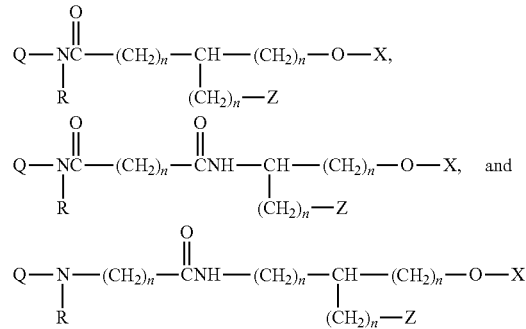

where $L_1$ is alkylamidediyl, $L_2$ is alkoxydiyl, $L_3$ is alkyldiyl, and n is 1 to 12.

Fluorescence quencher compositions of the invention may include a quencher moiety linked to a solid support through a cleavable linker, represented by the general structures IV and V:

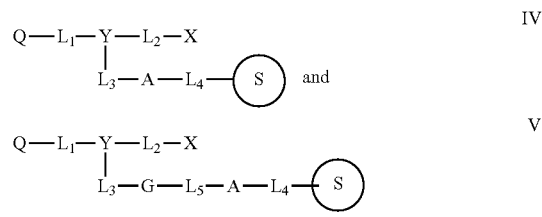

where Q, Y, $L_1$, $L_2$, and $L_3$ are selected from structures I, II, and III. A may be any cleavable linker, including the structures:

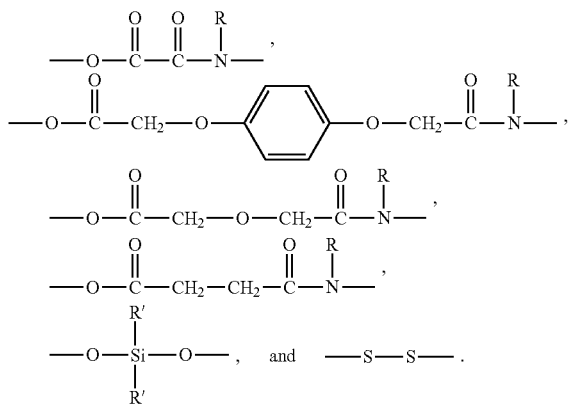

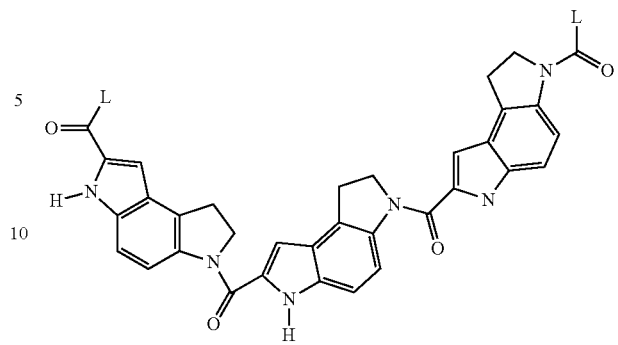

where L are the sites of attachment to $L_3$ and $L_5$ (Dempcy, WO 01/31063).

Fluorescence quencher compositions of the invention include quencher-phosphoramidites according to the structure VI:

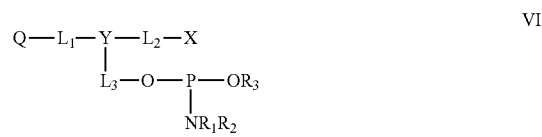

where Q, Y, $L_2$, and $L_3$ are selected from structures I, II, and III. Quencher-phosphoramidite reagents VI are particularly useful for the automated synthesis of labelled polynucleotides. The phosphoramidite reagents can be nucleosidic (X=nucleoside) or non-nucleosidic, according to structure VI, which can effect labelling of a polynucleotide or polypeptide with one or more protected or unprotected quencher moieties, Q. When taken separately, $R_1$ and $R_2$ are $C_1$-$C_{12}$ alkyl such as methyl, ethyl, or isopropyl; $C_5$-$C_{14}$ aryl; or cycloalkyl containing up to 10 carbon atoms such as, morpholino. When taken together with the phosphoramidite nitrogen atom, $R_1$ and $R_2$ may be $C_4$-$C_{11}$ cycloalkyl, e.g. morpholino. $R_3$ is a phosphite ester protecting group which prevents unwanted extension of the polynucleotide. Generally, $R_3$ is stable to polynucleotide or polypeptide synthesis conditions yet is able to be removed from a synthetic polynucleotide product with a reagent that does not adversely affect the integrity of the polynucleotide or the dye. $R_3$ may be $C_1$-$C_6$ alkyl, such as methyl, tert-butyl, or cyanoethyl; $C_5$-$C_{14}$ aryl, such as phenyl or 2-(4-nitrophenyl)ethyl.

Exemplary quencher-phosphoramidite 75 (Example 42) was prepared by coupling linker compound 76 with quencher NHS ester 36 by amide bond formation (Example 34) to form 77 which was phosphitylated to give 75.

Fluorescence quencher compositions of the invention include quencher-supports where a nucleotide is attached at its 3' or 5' position, according to the structures VII and VIII:

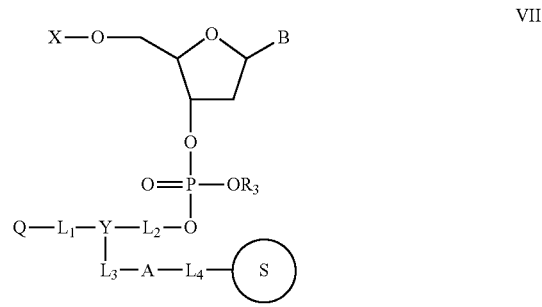

R' is H, $C_1$-$C_{12}$ alkyl or $C_1$-$C_{12}$ alkoxy. Additionally, the cleavable linker may be an allyl or propargyl linker, cleavable by a metal reagent, such as a palladium complex.

$L_4$ and $L_5$ may be a bond, $C_1$-$C_{12}$ alkyldiyl, $C_1$-$C_{12}$ alkoxyldiyl, $C_1$-$C_{12}$ alkylaminodiyl, $C_1$-$C_{12}$ alkylamidediyl, $C_5$-$C_{14}$ aryldiyl, or 1-20 ethyleneoxy units.

The ester linkers A may be cleaved by basic reagents such as aqueous or gaseous ammonium hydroxide, anhydrous amines, aqueous hydroxide reagents, and aqueous amines. The ester linkers may be selected on the basis of their cleavage rate and desired stability of the linkage between the quencher moiety and the solid support. For example, an oxalate linkage is relatively labile, being virtually completely cleaved within a few minutes in concentrated ammonium hydroxide at room temperature. The succinate linkage may require one hour or more under the same conditions. The quinone and diglycolate linkages have intermediate stability to basic cleavage. Alkoxysilyl linkers may be cleaved by strong base or fluoride reagents. Disulfide linkers may be cleaved by reducing agents such as dithiothreitol (DTT).

The solid support, (S), may be polystyrene, controlled-pore-glass, silica gel, silica, polyacrylamide, polyacrylate, hydroxyethylmethacrylate, polyamide, polyethylene, polyethyleneoxy, or copolymers and grafts of such. The solid support may be in any form, e.g. a particle, a bead, a membrane, a frit, a fiber, a tube, a capillary, a slide, a plate, a micromachined chip, an alkanethiol-gold layer, a magnetic bead, a non-porous surface, an addressable array, or any polynucleotide-immobilizing medium.

G is a hybridization-stabilizing moiety, such as a minor groove binder, intercalator, polycation, such as polylysine and spermine, and cross-linking functional group. Hybridization-stabilizers may increase the stability of base-pairing, i.e. affinity, or the rate of hybridization (Corey (1995) J. Amer. Chem. Soc. 117:9373-74) of the primer and target, or probe and target. Hybridization-stabilizers serve to increase the specificity of base-pairing, exemplified by large differences in Tm between perfectly complementary oligonucleotide and target sequences and where the resulting duplex contains one or more mismatches of Watson/Crick base-pairing (Blackburn, G. and Gait, M. Eds. "DNA and RNA structure" in *Nucleic Acids in Chemistry and Biology*, 3rd Edition, (1996) Oxford University Press, pp. 15-81 and 337-46). Minor groove binders include Hoechst 33258 (Rajur (1997) J. Org. Chem. 62:523-29), distamycin, netropsin, (Gong (1997) Biochem. and Biophys. Res. Comm. 240:557-60), and $CDPI_{1-3}$ (U.S. Pat. No. 5,801,155; WO 96/32496). An example of a minor groove binder is $CDPI_3$, represented by the structure:

VIII

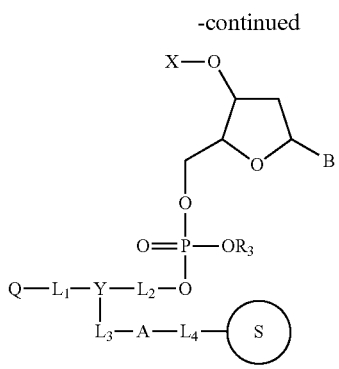

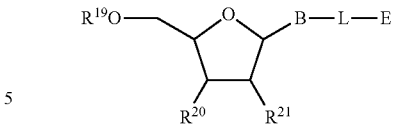

where Q, Y, L₁, L₂, L₃, and L₄ are selected from structures I, II, III, and IV. X is H or an acid-labile protecting group. B may be any protected or unprotected nucleobase. The exocyclic amino groups of nucleobase may be protected with acyl groups, e.g. isobutyryl or benzoyl, and as formamidines and acetamidines. $R_3$ may be unprotected, e.g. phosphodiester; or protected, e.g. cyanoethyl, $C_1$-$C_6$ alkyl, or $C_5$-$C_{14}$ aryl.

Compositions VII and VIII may be intermediates formed during automated oligonucleotide synthesis on a solid support. Composition VII may be formed by: (1) deprotecting quenchers-support IV, i.e. removing the acid-labile protecting group X with acid, (2) coupling a 3'-phosphoramidite nucleoside, and (3) oxidizing the internucleotide phosphite linkage to phosphate. For example, where $L_2$ is alkoxydiyl and X is DMT, IV is treated with trichloroacetic acid or dichloroacetic acid. Addition of subsequent nucleosides by iteration of the above steps (1), (2), and (3) in a cycle results in the 3' to 5' direction synthesis of an oligonucleotide. Optionally, a capping step may be conducted to prevent any unreacted sites from subsequent propagation, e.g. acetylation of 5' OH with acetic anhydride. Cleavage of linker A results in a 3'-quencher labelled oligonucleotide. Composition VIII may be formed by the same steps (1), (2), and (3), with iteration to give an oligonucleotide synthesized in the 5' to 3' direction, when 5'-phosphoramidites are employed in step (2). Cleavage of linker A then results in a 5'-quencher labelled oligonucleotide.

V.3 QUENCHER LABELLED NUCLEOSIDES AND NUCLEOTIDES

The sugar or nucleobase moieties of nucleotide 5'-triphosphates may be labelled with the quencher moieties I and II for use in certain embodiments of the invention. Nucleobase labelling sites include the 8-C of a purine nucleobase, the 7-C or 8-C of a 7-deazapurine nucleobase, and the 5-position of a pyrimidine nucleobase (Nardone, U.S. Pat. No. 6,117,986). The labelled nucleotide may be enzymatically incorporatable and enzymatically extendable by polymerases or reverse transcriptase. Quencher labelled nucleosides and nucleotides may have the following formula:

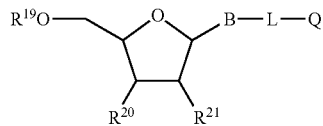

where Q is a protected or unprotected quencher. Alternatively, quencher labelled nucleosides and nucleotides may have the following formula:

where E is an energy transfer pair comprising a reporter dye and a quencher moiety attached by a linker. B is a nucleobase, e.g. uracil, thymine, cytosine, adenine, 7-deazaadenine, guanine, and 8-deazaguanosine. $R^{19}$ is triphosphate, thiophosphate, or phosphate ester analog. Alternatively, the quencher labelled nucleosides may be intermediates useful for conversion to nucleotide 5'-triphosphates or other compounds, where $R^{19}$ is H or an acid-labile protecting group. The acid-labile protecting group may be a trityl group, such as DMT. $R^{20}$ and $R^{21}$, when taken alone, are each independently H, HO, and F. Linker L may include alkynyl, propargyl, propargylethoxyamido, vinyl, and allyl groups. For example, L may be:

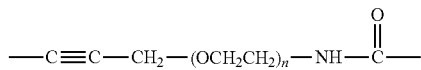

wherein n is 0, 1, or 2 (Khan, U.S. Pat. Nos. 5,770,716 and 5,821,356; Hobbs, U.S. Pat. No. 5,151,507).

V.4 QUENCHER LABELLED POLYNUCLEOTIDES

Polynucleotides are commonly synthesized on solid supports by the phosphoramidite method (Caruthers, U.S. Pat. No. 4,973,679; Beaucage (1992) Tetrahedron 48:2223-2311), using commercially available phosphoramidite nucleosides (Caruthers, U.S. Pat. No. 4,415,732), supports, e.g. silica, controlled-pore-glass (Caruthers, U.S. Pat. No. 4,458,066) and polystyrene (Andrus, U.S. Pat. Nos. 5,047,524 and 5,262,530) and automated synthesizers such as Models 392, 394, 3948, 3900 DNA/RNA Synthesizers (Applied Biosystems, Foster City, Calif.).

Labelled polynucleotides may be formed by coupling a reactive linking group on a label, e.g. a quencher moiety, with a polynucleotide in a suitable solvent in which both are soluble or appreciably soluble, using methods well-known in the art. For labelling methodology, see Hermanson, *Bioconjugate Techniques*, (1996) Academic Press, San Diego, Calif. pp. 40-55, 643-71; Garman, 1997, *Non-Radioactive Labelling: A Practical Approach*, Academic Press, London. Crude, labelled polynucleotides may be purified from any starting materials or unwanted by-products, and stored dry or in solution for later use, preferably at low temperature.

The label may bear a reactive linking group at one of the substituent positions, e.g. an aryl-carboxyl group of a quencher moiety I or II, or the 5- or 6-carboxyl of fluorescein or rhodamine, for covalent attachment through a linkage. Generally, the linkage linking a label and the polynucleotide or nucleotide should not (i) interfere with hybridization affinity or specificity, (ii) diminish quenching, (iii) interfere with primer extension, (iv) inhibit polymerase activity, or (v) adversely affect the fluorescence or quenching properties of the label. Electrophilic reactive linking groups form a covalent bond with nucleophilic groups such as amines and thiols on a polynucleotide or polypeptide. Examples of electrophilic reactive linking groups include active esters, isothiocyanate, sulfonyl chloride, sulfonate ester, silyl halide, 2,6- dichlorotriazinyl, phosphoramidite, maleimide, haloacetyl, epoxide, alkylhalide, allyl halide, aldehyde, ketone, acylazide, anhydride, and iodoacetamide. Active esters include succinimidyl (NHS), hydroxybenzotriazolyl (HOBt) and pentafluorophenyl esters.

An NHS ester of a quencher moiety may be preformed, isolated, purified, and/or characterized, or it may be formed in situ and reacted with a nucleophilic group of a polynucleotide or polypeptide. Typically, a quencher moiety carboxyl group is activated by reacting with some combination of: (1) a carbodiimide reagent, e.g. dicyclohexylcarbodiimide, diisopropylcarbodiimide, EDC (1-ethyl-3-(3-dimethylaminopropyl)carbodiimide); or a uronium reagent, e.g. TSTU (O—(N-Succinimidyl)-N,N,N',N'-tetramethyluronium tetrafluoroborate, HBTU (O-benzotriazol-1-yl)-N,N,N',N'-tetramethyluronium hexafluorophosphate), or HATU (O-(7-azabenzotriazol-1-yl)-N,N,N',N'-tetramethyluronium hexafluorophosphate); (2) an activator, such as HOBt (1-hydroxybenzotriazole) or HOAt (1-hydroxy-7-azabenzotriazole; and (3) N-hydroxysuccinimide to give the NHS ester.

The general quencher-phosphoramidite VI reacts with a hydroxyl group, e.g. 5' terminal OH of a polynucleotide bound to a solid support, under mild acid activation, to form an internucleotide phosphite group which is then oxidized to an internucleotide phosphate group. Alternatively, the quencher-phosphoramidite reagent reacts with a hydroxyl group on the side chain of an amino acid of a polypeptide such as serine, threonine, or tyrosine. In some instances, the quencher moiety contains functional groups that require protection either during the synthesis of the phosphoramidite reagent or during its subsequent use to label polynucleotides or polypeptides. The protecting group(s) used will depend upon the nature of the functional groups, and will be apparent to those having skill in the art (Greene, T. and Wuts, P. *Protective Groups in Organic Synthesis,* 2nd Ed., John Wiley & Sons, New York, 1991). The quencher will be attached at the 5' terminus of the polynucleotide, as a consequence of the common 3' to 5' direction of synthesis method. Alternatively, the 3' terminus of a polynucleotide may be labelled with a quencher-phosphoramidite when synthesis is conducted in the less-common 5' to 3' direction with 3'-protected, 5' phosphoramidite nucleosides (Wagner, (1997) Nucleosides & Nucleotides 16:1657-60). Other quencher-phosphoramidite reagents, nucleosidic and non-nucleosidic, allow for labelling at other sites of a polynucleotide, e.g. 3' terminus, nucleobase, internucleotide linkage, sugar. Labelling at the nucleobase, internucleotide linkage, and sugar sites allows for internal and multiple labelling.

A nucleobase-labelled polynucleotide may have the following formula:

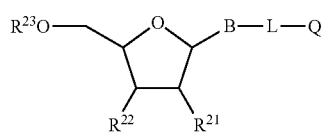

where the primer or probe comprises 2 to 100 nucleotides and Q is a protected or unprotected quencher. Alternatively, a nucleobase-labelled polynucleotide may have the following formula:

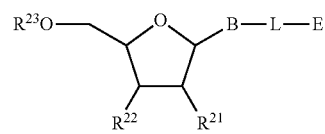

where E is an energy transfer pair comprising a reporter dye and a quencher moiety attached by a linker. B is a nucleobase, e.g. uracil, thymine, cytosine, adenine, 7-deazaadenine, guanine, and 8-deazaguanosine. L is a linker, e.g. propargyl, propargylethoxyamido, allyl, vinyl, or $C_1$-$C_{12}$ alkyldiyl. $R^{21}$ is H, OH, halide, azide, amine, $C_1$-$C_6$ aminoalkyl, $C_1$-$C_6$ alkyl, allyl, $C_1$-$C_6$ alkoxy, —$OCH_3$, or —$OCH_2CH=CH_2$. $R^{22}$ is H, phosphate, internucleotide phosphodiester, or internucleotide analog. $R^{23}$ is H, phosphate, internucleotide phosphodiester, or internucleotide analog. In this embodiment, the nucleobase-labelled polynucleotide may bear multiple fluorescent labels, e.g. dyes, attached through the nucleobases. Nucleobase-labelled polynucleotides may be formed by: (i) enzymatic incorporation of enzymatically incorporatable nucleotide reagents where $R^{19}$ is triphosphate, by a DNA polymerase or ligase, and (ii) coupling of a nucleoside phosphoramidite reagent by automated synthesis (Theisen (1992) "Fluorescent dye phosphoramidite labelling of polynucleotides", in *Nucleic Acid Symposium Series* No. 27, Oxford University Press, Oxford, pp. 99-100). 5' quencher-labelled polynucleotides of the invention include the following structure:

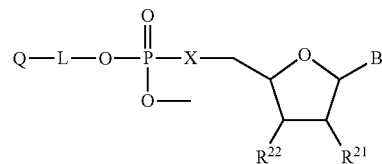

where Q is structure I or II. X is O, NH, or S; $R^{21}$ is H, OH, halide, azide, amine, $C_1$-$C_6$ aminoalkyl, $C_1$-$C_6$ alkyl, allyl, $C_1$-$C_6$ alkoxy, —$OCH_3$, or —$OCH_2CH=CH_2$; and $R^{22}$ is internucleotide phosphodiester, or internucleotide analog. L is a linker, including $C_1$-$C_{12}$ alkyldiyl, e.g. n-hexyldiyl, aryldiyl, or polyethyleneoxy (U.S. Pat. No. 4,757,141; Andrus, "Chemical methods for 5' non-isotopic labelling of PCR probes and primers" (1995) in *PCR 2: A Practical Approach,* Oxford University Press, Oxford, pp. 39-54; Hermanson, in *Bioconjugate Techniques,* (1996) Academic Press, San Diego, Calif. pp. 40-55, 643-71; Mullah (1998) Nucl. Acids Res. 26:1026-1031). The 5' quencher-polynucleotide may have additional covalently attached labels, such as a fluorescent dye or a minor groove binder.

A solid support bearing a quencher of the present invention, or bearing functionality which can be labelled by a quencher in a post-synthesis reaction, can be utilized as a solid support for polynucleotide synthesis (U.S. Pat. Nos. 5,141,813; 5,231,191; 5,401,837; 5,736,626). By this approach, the quencher or the functionality is present during synthesis of the polynucleotide. During cleavage and deprotection, the quencher or the functionality remains covalently attached to the polynucleotide. Polynucleotides labelled at the 3' terminus may have the following structure:

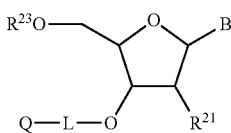

where the probe comprises 2 to 100 nucleotides. Q is structure I or II. B is any nucleobase, e.g. uracil, thymine, cytosine, adenine, 7-deazaadenine, guanine, and 8-deazaguanosine. L is a linker, including $C_1$-$C_{12}$ alkyldiyl, e.g. n-hexyldiyl, aryldiyl, or polyethyleneoxy. $R^{21}$ is H, OH, halide, azide, amine, $C_1$-$C_6$ aminoalkyl, $C_1$-$C_6$ alkyl, allyl, $C_1$-$C_6$ alkoxy, —$OCH_3$, or —$OCH_2CH$=$CH_2$. $R^{23}$ is internucleotide phosphodiester or internucleotide analog. The 3' quencher-polynucleotide may have additional covalently attached labels, such as a fluorescent dye or a minor groove binder.

In another embodiment of the invention, 3' quencher-polynucleotides bound to a solid support may be derived from VII and have the general structure:

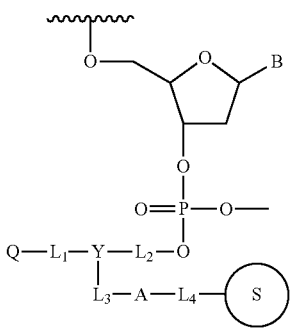

where the polynucleotide comprises 2 to 100 nucleotides. Alternatively, 5' quencher labelled polynucleotides bound to a solid support may be derived from VIII and have the general structure:

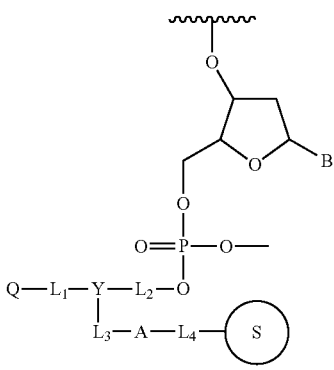

where the polynucleotide comprises 2 to 100 nucleotides.

Polynucleotides can be immobilized on solid supports by a covalent bond attachment, ionic interaction, hybridization to an immobilized probe, hydrophobic interaction, or ligand/receptor interaction, using a variety of known procedures (Lane, U.S. Pat. No. 5,902,724; Mirkin, WO 98/04740). Covalent bonds between a polynucleotide and solid support include Schiff-base type linkages (Lukhtanov, WO 01/09385) and phosphoramidate linkages (Rampal, U.S. Pat. No. 6,013,789).

Nucleic acid analogs are structural analogs of DNA and RNA and which are designed to hybridize to complementary nucleic acid sequences. Through modification of the internucleotide linkage, the sugar, and/or the nucleobase, nucleic acid analogs of the invention may attain any or all of the following desired properties: 1) optimized hybridization specificity or affinity, 2) nuclease resistance, 3) chemical stability, 4) solubility, 5) membrane-permeability, and 6) ease or low costs of synthesis and purification. The fluorescence quencher compositions of the invention include nucleic acid analogs labelled with quencher moieties, e.g. structures III, IV, and V, where X=a nucleic acid analog.

One useful and accessible class of nucleic acid analogs is the family of peptide nucleic acids (PNA) in which the sugar/phosphate backbone of DNA or RNA has been replaced with acyclic, achiral, and neutral polyamide linkages. The N-[2-(aminoethyl)]glycine polyamide linkage with nucleobases attached to nitrogen through a methylene carbonyl linkage by an amide bond has been well-studied as an embodiment of PNA and shown to possess exceptional hybridization specificity and affinity (Buchardt, WO 92/20702; Nielsen (1991) Science 254:1497-1500; Egholm (1993) Nature, 365:566-68; Nielsen, P. and Egholm, M. (1999) in *Peptide Nucleic Acids; Protocols and Applications*, Horizon Scientific Press, Norfolk, England).

PNA may be synthesized at any scale, e.g. 2-100 μmole scale or more, using Fmoc/Bhoc, tBoc/Z, or MMT protecting group monomers on an Expedite Synthesizer (Applied Biosystems) on XAL or PAL support; or on the Model 433A Synthesizer (Applied Biosystems) with MBHA support; or on other automated synthesizers. PNA may be synthesized on many of the solid supports commonly used for peptide synthesis (M. W. Pennington and B. M. Dunn (Eds.) "Methods in molecular biology, Vol. 35: Peptide synthesis protocols", Humana Press, Totowa, N.J. (1994), pp. 91; G. Grant (Ed.), "Synthetic peptides", W.H. Freeman & Co., New York, N.Y., 1992; G. B. Fields, Int. J. Peptide Protein Res. (1990) 35:161; G. B. Fields (Eds.), "Methods in enzymology: Vol. 289", Academic Press, New York, N.Y., 1997; W. C. Chan and P. D. White, "Fmoc solid phase peptide synthesis: a practical approach, Oxford University Press, Oxford, UK, 2000; P. Lloyd-Williams and F. Albericio (Eds.), "Chemical approaches to the synthesis of peptides and proteins", CRC Press, New York, N.Y. 1997.

PNA-DNA chimera are oligomer molecules with discrete PNA and nucleotide moieties. They can be synthesized by covalently linking PNA monomers and nucleotides in virtually any combination or sequence. Efficient and automated methods have been developed for synthesizing PNA-DNA chimera (Vinayak (1997) Nucleosides & Nucleotides 16:1653-56; Uhlmann (1996) Angew. Chem., Intl. Ed. Eng. 35:2632-35; Uhlmann, EP 829542; Van der Laan (1997) Tetrahedron Lett. 38:2249-52; Van der Laan (1998) Bioorg. Med. Chem. Lett. 8:663-68. PNA-DNA chimera are designed to have desirable properties found in PNA and DNA, e.g. superior hybridization properties of PNA and biological functions like DNA, including primer extension through the 3' OH terminus of the DNA moiety (Uhlmann (1998) Biol. Chem. 379:1045-52). PNA and PNA-DNA chimera can be labelled with a quencher moiety I or II, and a fluorescent reporter, to form PNA FRET probes (Hyldig-Nielsen, U.S. Pat. No. 5,985,563; Coull, WO 98/24933; Coull, WO 99/22018; Gildea, WO 99/21881; Coull, WO 99/49293).

The linker between a PNA monomer unit and a label is: (i) a covalent bond; (ii) an $C_1$-$C_{12}$ alkyldiyl; (iii) ethyleneoxy —$(CH_2CH_2O)_n$—, where n is 1 to 12, (iv) $C_5$-$C_{14}$ aryidiyl; (v) 2-(2-aminoethoxy)acetic acid; or (vi) one or more amino acids (Gildea (1998) Tetrahedron Letters 39:7255-58). Lysine, aspartic acid, and glutamic acid side chains in the linker may be quencher-linkage sites in quencher-labelled PNA. The ε-amino group of the sidechain of lysine may be the reactive linking group for attachment of a label, e.g. fluorescent reporter or quencher moiety. Linkers are typically attached to the amino and/or carboxyl terminus of the PNA by the corresponding monomer units with compatible protecting groups and reactive functionality for condensation with PNA monomer units and the solid support. For example, the "O linker", units of 2-(2-aminoethoxy)acetic acid, can be attached to the amino terminus of any PNA backbone amino group, or on amino functionality of a solid support.

V.5 QUENCHER LABELLED POLYPEPTIDES

Polypeptides that are labeled with a quencher of the invention can be used in both in vivo and in vitro enzymatic assays. For example, the present invention provides generally for methods to determine if a sample contains an enzyme. A method may comprise: (a) contacting the sample with a polypeptide labelled with a fluorescent reporter and a quencher moiety; (b) exciting the fluorophore; and (c) determining a fluorescence property of the sample, wherein the presence of the enzyme in the sample results in a change in the fluorescence property. The change in fluorescence may be due to cleavage or assembly of a recognition site for the enzyme.

When the labelled polypeptide is used to detect an enzyme, such as a degradative enzyme (e.g. protease), the degree of donor-acceptor energy transfer in the sample can be determined, for example, as a function of the amount of fluorescence from the donor moiety, the amount of fluorescence from the acceptor moiety, the ratio of the amount of fluorescence from the donor moiety to the amount of fluorescence from the acceptor moiety or the excitation state lifetime of the donor moiety. The assay methods can also be used to determine whether a compound alters the activity of an enzyme, i.e. screening assays, and determining the amount of activity of an enzyme in a sample from an organism. Screening compounds produced by combinatorial chemistry requires convenient enzymatic assays. In one embodiment, the amount of enzyme activity in the sample is determined as a function of the degree of donor-acceptor energy transfer in the sample and the amount of activity in the sample is compared with a standard activity for the same or different concentration of enzyme.

Representative enzymes with which the present invention can be practiced include, for example, trypsin, enterokinase, HTV-1 protease, prohormone convertase, kininogenase, and proteases in general. The most convenient assays for proteases are based on donor-acceptor energy transfer from a donor fluorophore to a quencher placed at opposite ends of a short peptide chain containing the potential cleavage site (Knight C. G., (1995) Methods in Enzymol. 248:1 8-34). Proteolysis separates the fluorophore and quencher, resulting in increased intensity in the emission of the donor fluorophore.

In one embodiment, the polypeptide sequence includes a cleavage recognition site, specific for an enzyme or other cleavage agent of interest. A cleavage recognition sequence for a protease is a specific amino acid sequence recognized by the protease during proteolytic cleavage. Many protease cleavage sites are known in the art, and these and other cleavage sites can be included in the linker moiety (Matayoshi, (1990) Science 247:954; Dunn in Meth. in Enzymol. 241:254 (1994); Seidah in Meth. in Enzymol. 244: 175 (1994); Thornberry in Meth. in Enzymol. 244:615 10 (1994); Weber in Meth. in Enzymol. 244:595 (1994); Smith in Meth. in Enzymol. 244:412 (1994); Bouvier in Meth. in Enzymol. 248:614 (1995), Hardy in Amyloid Protein Precursor In Development, Aging, And Alzheimer's Disease, ed. Masters, pp. 190-198 (1994)). Cleavage of the sequence results in separation of the fluorescent dye and the quencher moiety of a FRET peptide. The cleavage may be measurable as a change in donor-acceptor energy transfer, with a resulting increase in detectable fluorescence. Conversely, peptide assembly can be detected by an increase in donor-acceptor energy transfer (quenching) between a peptide fragment bearing quencher moiety and a peptide fragment bearing a fluorescent reporter.

Labelling of polypeptides with reporter moieties and other labels for research in immunology, histochemistry, and cell biology has been reviewed. See: Lundblad, R. L. and Noyes, C. M. (1984) Chemical Reagents for Protein Modification, Vols. I and II, CRC Press, New York; Pfleiderer, G. (1985) Chemical Modification of Proteins, In Modern Methods in Protein Chemistry, H. Tschesche, Ed., Walter DeGryter, Berlin and New York; Wong (1991) Chemistry of Protein Conjugation and Cross-linking, CRC Press, Boca Raton, Fla.

An electrophilic reactive linking group of a quencher moiety of the invention can react with a nucleophilic side chain of an amino acid in a polypeptide (Brinkley, 1992, Bioconjugate Chem. 3:2). The aliphatic ε-amine of the amino acid lysine is often a good nucleophile above pH 8.0 ($pK_a$=9.18) (Fasman, G. D. Ed. (1989) Practical Handbook of Biochemistry and Molecular Biology, p13, CRC Press, Boca Raton, Fla.) and therefore reacts easily and cleanly with a variety of electrophilic reagents to form stable bonds. Other reactive amines that are found in proteins are the α-amino groups of the N-terminal amino acids. The α-amino groups are less basic than lysines and are reactive at around pH 7.0. Sometimes they can be selectively modified in the presence of lysines. There is usually at least one α-amino acid in a protein, and in the case of proteins that have multiple peptide chains or several subunits, there can be more (one for each peptide chain or subunit). Since either N-terminal amines or lysines are almost always present in any given protein or peptide, and since they are easily reacted, the most commonly used method of protein modification is through these aliphatic amine groups. The quencher moiety may be conjugated to the N-terminus of a resin-bound polypeptide before removal of other protecting groups and release of the labeled peptide from the resin. About five equivalents of an amine-reactive quencher reagent may be used per amine of the immobilized peptide (Haugland, 1996, Molecular Probes Handbook of Fluorescent Probes and Research Chemicals, Molecular Probes, Inc.)

Another reactive linking group in many polypeptides is a thiol residue from the sulfur-containing amino acid cystine and its reduction product cysteine (or half-cystine), which are counted together as one of the 20 amino acids. Cysteine contains a free thiol group, which is more nucleophilic than amines and is generally the most reactive functional group in a protein. It reacts with some of the same modification reagents as do amines and in addition can react with reagents that are not very reactive toward amines. Unlike most amines, thiols are reactive at neutral pH, and therefore they can be coupled to other molecules selectively in the presence of amines. Since free sulfhydryl groups are relatively reactive, proteins with these groups often exist in their oxidized form as disulfide-linked oligomers or have internally bridged disulfide groups. Reduction of the disulfide bonds with a reagent such as dithiothreitol (DTT) is required to generate the reactive free thiol. In addition to cystine and cysteine, some proteins also have the amino acid methionine, which contains sulfur in a thioether linkage.

Acylation reactions may be performed at polypeptide amino groups with quencher reagents. Acylation reactions may be described by the following general scheme:

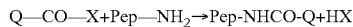

where Pep is the polypeptide, X is a leaving group and Q is the quencher moiety. The reactive reagent Q-CO—X may be produced in situ by the action of an activating agent, such as a carbodiimide, on the free carboxylic acid, but more preferable is the use of stable active esters that may be stored as solid reagents, e.g. N-hydroxysuccinimide (NHS) esters, and also more water-soluble sulfonated forms. Other amine-reactive reagents which may serve as reactive linking groups for the quencher moiety to prepare quencher-labelled polypeptide include other succinimidyl esters, isothiocyanates (—NCS), sulphonyl halides (—$SO_2Cl$) and dichlorotriazine derivatives. Thiol-reactive reagents include iodoacetyl (—C(O)$CH_2$I) and maleimido derivatives.

V.6 NUCLEIC ACID ASSAY METHODS

Oligonucleotides labelled with a fluorescent dye and a quencher of the invention are useful in a wide variety of important nucleic acid hybridization and amplification applications, including allelic discrimination and real-time PCR quantitation. The specificity of such oligonucleotides as primers and probes is effective for distinguishing single base-pair differences and mismatches.

The fluorescent/quencher probes of the invention are useful as detection agents in a variety of DNA amplification/quantification strategies including, for example, 5'-nuclease assay, Strand Displacement Amplification (SDA), Nucleic Acid Sequence-Based Amplification (NASBA), Rolling Circle Amplification (RCA), Oligonucleotide Ligation Assay (OLA), Ligase Chain Reaction (LCR), Transcription-Mediated Amplification (TMA) and Q-beta replicase. Fluorescent/quencher, probes are also useful for direct detection of targets in other solution phase or solid phase (e.g., array) assays. Furthermore, the fluorescent/quencher probes can be used in any format, including, for example, molecular beacons, Scorpion Probes™, Sunrise Probes™, light up probes, Invader™ Detection probes, and TaqMan™ probes. See, for example, Cardullo, R. (1988) Proc. Natl. Acad. Sci. USA, 85:8790-8794; Stryer, L., (1978) Ann. Rev. Biochem., 47:819-846; Rehman, F. N., (1999) Nucleic Acids Research, 27:649-655; Gibson, E. M., (1996) Genome Methods, 6:995-1001; Livak, U.S. Pat. No. 5,538,848; Wittwer, C. T., (1997) BioTechniques, 22:176-181; Wittwer, C. T., (1997) BioTechniques, 22:130-38; Tyagi, WO 95/13399, U.S. Pat. Nos. 6,037,130, 6,150,097, and 6,103,476; Uehara, H. (1999) BioTechniques, 26:552-558; Whitcombe, (1999) Nature Biotechnology, 17:804-807; Lyamichev, V. (1999) Nature Biotechnology, 17:292; Daubendiek, (1991) Nature Biotechnology, 15:273-350; Nardone, WO 99/64432; Nadeau, U.S. Pat. Nos. 5,846,726 and 5,928,869; and Nazarenko, U.S. Pat. No. 5,866,336.

A method of the invention includes nucleic acid amplification, i.e. amplifying a target polynucleotide, i.e. template DNA, with nucleotide 5'-triphosphates, a polymerase, and two or more primers. The primers are complementary to the target polynucleotide sequence. One or more of the primers can be covalently attached by a linkage to an aryl carbon of a quencher moiety I or II. A detectable probe, complementary to the target polynucleotide sequence, may also be included in the amplification reaction.

The ability to detect and quantitate gene targets rapidly, in real time or by end-point PCR detection, can be carried out with the 5'-nuclease assay, often referred to as "TaqMan®" (Gelfand, U.S. Pat. No. 5,210,015; Holland, Proc. Natl. Acad. Sci. USA, 88: 7276-7280 (1991); Lee, Nucleic Acids Res., 21: 3761-3766 (1993); Livak, U.S. Pat. No. 5,723,591; Lyamichev, (1993) Science, 260:778-783). The process uses the 5' to 3' exonuclease activity of TAQ polymerase, and other thermo-stable polymerases, to digest the double-labelled, self-quenched, detectable probe during the PCR amplification process. The probe is cleaved by the 5'-exonuclease activity of DNA polymerase if, and only if, it hybridizes within the target sequence being amplified, i.e. between the primer-binding sites. Cleavage of the probe generates an increase in the fluorescence intensity of the fluorescent reporter. The fluorescent donor and quencher are preferably each located at or near the 3'- and 5'-ends of the probe. For example, a probe may be designed with a 5' fluorescent reporter dye, e.g. carboxyfluorescein, and a 3' quencher moiety of the present invention. The Tm of the probe (about 65° C.) is selected primarily on the basis of length and G+C content and known algorithms to insure binding to the target polynucleotide under extension conditions.

In one embodiment, the detectable probe is synthesized using a 3'-quencher support, e.g. 65 (Example 46) or 69 (Example 47). The dual-labelled, detectable probe is synthesized on the support including the step of covalent attachment of the fluorescent reporter. The fluorescent reporter may be added as a phosphoramidite reagent (e.g. VI, X=DMT) within the oligonucleotide, or as the last base (3' to 5' direction) at the 5' terminus of the oligonucleotide. Alternatively, the fluorescent reporter can be attached via a reactive linking group, e.g. NHS ester, at the 5' terminus of a 5' nucleophile (amino or thiol) oligonucleotide which has been cleaved from the support and deprotected. The fluorescent reporter may then be deprotected, if necessary, and the dual labelled oligonucleotide can be analyzed and purified. To function as a nuclease assay probe, i.e. "TaqMan" probe, the 3'-terminal nucleotide of the probe is blocked or rendered incapable of extension by a nucleic acid polymerase. Such blocking is achieved conveniently by the quencher moiety or the fluorescent reporter at the terminal 3'-hydroxyl. Alternatively, the 3' hydroxyl may be phosphorylated or blocked by other functionality.

One method of the invention includes nucleic acid amplification, i.e. amplifying a target polynucleotide with nucleotide 5'-triphosphates, a polymerase, two or more primers, and a detectable probe. The detectable probe may be labelled with a fluorescent reporter dye and a quencher moiety. The primers are complementary to the target polynucleotide sequence. The probe is complementary to the target polynucleotide at a binding site between the primer binding sites. The probe is covalently attached by a linkage to an aryl carbon of a quencher moiety I or II. A signal can be detected from the detectable probe, either upon hybridization of the probe to the target, or upon cleavage of the probe by the polymerase, during amplification.

Cleavage of the dual labelled, self-quenching probe by TAQ polymerase with 5'-nuclease activity generates free fluorescent reporter each cycle of amplification, leading to exponential accumulation of fluorescent signal, correlated to the exponential production of PCR product ("amplicon"). By plotting the fluorescent signal vs. PCR cycle number and comparing with a standard reference curve, the number of starting gene copies can be determined. A threshold cycle, $C_T$, is designated, as the fractional cycle number, at which the increase in fluorescence crosses some fixed threshold above baseline. Thus, the 5'-nuclease assay determines both the presence of a gene as well as the amount of gene present. By using different probes with unique reporter fluorophores, several gene determinations can be performed simultaneously in the same reaction tube. As probes can be designed to discern a single base mismatch, specific alleles may be determined.

The power and utility of the 5'-nuclease assay has been expanded by the introduction of instrument systems (e.g. ABI PRISM® 7700 and 7900HT Sequence Detector Systems, Applied Biosystems) which automatically conduct the 5'-nuclease PCR process in 96- and 384-tube or well microtiter formats. Since the vessels are closed throughout the process, by-products derived by contamination are prevented. The instrument monitors the fluorescence (at several wavelengths to allow multiplexing with multiple reporter dyes) in each well. Fluorophore multiplexing further expands the number of assays possible by allowing more than one target sequence to be interrogated per vessel, with multiple probes labelled with different dyes.

By configuring standard primer pairs and probes as reagent kits and robotic dispensing into the vessels (i.e. tubes, wells, array loci, or spots), high-throughput assays for the rapid profiling of single-nucleotide polymorphisms (SNP), allelic discrimination, or disease related genes are enabled.

Sensitivity and accuracy of 5'-nuclease PCR and hybridization assays are limited where the self-quenching probes have inherent noise, i.e. background fluorescence. The non-fluorescent quencher moieties of the invention have the advantages of not adding fluorescence to detection, and obviating: (1) labor-intensive or costly steps, such as post-PCR purification; (2) elaborate controls; and (3) complicated data processing.

A series of 5'-fluorescent reporter, 3'-quencher probes were synthesized with a 3' quencher support 69 (Example 48) and fluorescent dye phosphoramidites for the 5' labelling (Example 50). These probes were used in the 5' nuclease assay, i.e. "TaqMan", on the ABI Prism 7700 instrument (Example 51). By way of comparison, the same probe sequence was labelled with the same set of 5' fluorescent dyes. The variable of study was the quencher moiety. The second set of probes was labelled with TAMRA (tetramethylrhodamine), a fluorescent quencher. Efficiency of amplicon production and detection was measured by the change in fluorescence, relative to baseline ($\Delta$Rn) and the threshold cycle number ($C_T$). The results are summarized in the table below. No significant differences in the average $\Delta$Rn and $C_T$ values were observed for quencher 34 and TAMRA. $\Delta$Rn is the increase in reporter fluorescence at any cycle minus baseline fluorescence. The $\Delta$Rn values reported are after 40 cycles of PCR. Threshold cycle $C_T$ is the fractional PCR cycles number at which $\Delta$Rn crosses some fixed threshold above baseline. Four replicates were run to determine the average and standard deviation for each value. By all comparisons, the non-fluorescent quencher probes (Example 51) gave equal or superior performance relative to the TAMRA probes.

| Reporter dye | | $\Delta$Rn | | $C_T$ | |
|---|---|---|---|---|---|
| | | 34 | TAMRA | 34 | TAMRA |
| $F_1$ | Average | 1.74 | 1.66 | 19.58 | 19.71 |
| | Standard deviation | 0.04 | 0.01 | 0.21 | 0.10 |
| $F_2$ | Average | 1.47 | 1.82 | 20.08 | 19.92 |
| | Standard deviation | 0.02 | 0.02 | 0.02 | 0.09 |
| $F_3$ | Average | 0.70 | 0.63 | 20.96 | 21.41 |
| | Standard deviation | 0.05 | 0.04 | 0.06 | 0.19 |

-continued

| Reporter dye | | $\Delta$Rn | | $C_T$ | |
|---|---|---|---|---|---|
| | | 34 | TAMRA | 34 | TAMRA |
| $F_4$ | Average | 0.84 | 0.87 | 20.71 | 20.75 |
| | Standard deviation | 0.02 | 0.02 | 0.08 | 0.11 |

Probes containing a fluorescent dye-quencher pair have been developed for hybridization assays where the probe forms a hairpin structure due to a self-complementary sequence. A hairpin probe hybridizes to itself to form a stem/loop structure. In this conformation and in the absence of a complementary nucleic acid sequence, the quencher molecule may brought into proximity with the fluorescent reporter dye to effectively quench the fluorescence of the fluorescent dye (WO 90/03446; EP 0601889 A2). When a complementary target sequence is present, hybridization of the hairpin FRET probe to the complementary target sequence disrupts the hairpin structure and causes the probe to adopt a conformation where the quencher molecule is no longer close enough to the reporter molecule to quench the reporter molecule. As a result, the probes provide an increased fluorescent signal when hybridized to a target sequence than when they are unhybridized (Tyagi (1996) (Nature Biotech., 14:303-309; U.S. Pat. Nos. 5,119,801 and 5,312,728). In one embodiment, the hybridization probe may be labelled at the 5' or 3' terminus with the fluorescent dye and at the other terminus with a quencher moiety of the invention. When the FRET probe is hybridized to a target polynucleotide, i.e. open conformation, the fluorescence of the fluorescent dye is detectable, whereas when the FRET probe is in hairpin (closed) conformation, the fluorescence of the donor fluorophore is quenched. The probes for hybridization detection may comprise a nucleic acid analog, e.g. one or more PNA (N-[2-(aminoethyl)]glycine) units having a nucleobase attached to nitrogen through a methylene carbonyl linkage, or LNA (2'-4' or 3'-4' bicyclic sugar modifications). When employed in PCR, the FRET probe hybridized to one of the strands of the PCR product is "open" and is detected, while those that remain closed in the hairpin conformation, i.e. unbound to target, do not fluoresce because the fluorescent dye is quenched. As a result, the amount of fluorescence will increase as the amount of PCR product increases, and thus can be used as a measure of the progress of the PCR. In other words, fluorescent intensity is correlated with PCR.

Polynucleotide fragments labelled with quencher moieties I and II may be generated through template-directed enzymatic synthesis using quencher-labelled primers or quencher-labelled nucleotides, e.g. by ligation or polymerase-directed primer extension. The resulting polynucleotide fragments may be further labelled with fluorescent reporters to form energy-transfer pairs. Quencher labelled polynucleotide fragments may serve to intermolecularly quench the fluorescence of other fluorescent-labelled compounds. Polynucleotide fragments may be subjected to a size-dependent separation process, e.g., electrophoresis or chromatography, and the separated fragments are detected subsequent to the separation, e.g., by laser-induced fluorescence (Hunkapiller, U.S. Pat. No. 4,811,218). Multiple classes of polynucleotides may be separated simultaneously and the different classes are distinguished by spectrally resolvable fluorescent reporters. In electrophoresis, the classes separate on the basis of electrophoretic migration rate.

The chain termination methods of DNA sequencing, i.e. dideoxy DNA sequencing, or Sanger-type sequencing, and fragment analysis may be employed (Sanger (1977) "DNA sequencing with chain-terminating inhibitors", Proc. Natl. Acad. Sci. USA 74:5463-5467) with the fluorescence quenching compositions of the invention Exemplary chain-terminating nucleotide analogs "terminators" include the 2',3'-dideoxynucleoside 5'-triphosphates (ddNTP) which lack the 3'-OH group necessary for 3' to 5' DNA chain elongation. A primer or ddNTP may be labelled with a quencher moiety and a fluorescent reporter to form an energy transfer pair within the primer extension product. The change in fluorescence from each fragment may be detected after separation of the fragments by high-resolution electrophoresis.

In another embodiment of the invention, a ligation event may be detected and monitored with oligonucleotide probes labelled with quencher moieties I and II. Covalent joining of nucleic acid probes by ligase enzymes is one of the most useful tools available to molecular biologists. When two probes are annealed to a template nucleic acid where the two probes are adjacent and without intervening gaps, a phosphodiester bond can be formed between a 5' terminus of one probe and the 3' terminus of the other probe by a ligase enzyme, (Whiteley, U.S. Pat. No. 4,883,750; Landegren, (1988) "A ligase mediated gene detection technique", Science 241:1077-80; Nickerson, "Automated DNA diagnostics using an ELISA-based oligonucleotide assay" (1990) Proc. Natl. Acad. Sci USA 87:8923-27). Oligonucleotide ligation assays detect the presence of specific sequences in target DNA sample. Where one probe is labelled with a fluorescent reporter and the other probe is labelled with a quencher moiety of the invention, the ligation product may be detected by fluorescence. Ligation products may be separated by electrophoresis, chromatography, or other size- or charge-based separation method.

In one embodiment, a quencher-oligonucleotide of the present invention may be immobilized on a solid support and used as a capture probe. The probe may be covalently attached directly to a solid support, for example by attachment of the 3'- or 5'-terminal nucleotide of the probe to the solid support. The probe may be attached to the solid support by a linker which serves to distance the probe from the solid support. The linker may be about 5 to about 30 atoms in length, or more.

Examples of preferred types of solid supports for immobilization of the oligonucleotide probe include controlled pore glass, glass plates, polystyrene, avidin-coated beads; cellulose, nylon, polystyrene grafted with polyethylene glycol, polyacrylamide gel and activated dextran. These solid supports are preferred for hybridization and diagnostic studies because of their chemical stability, ease of functionalization and well defined surface area. Solid supports such as controlled pore glass (CPG) and non-swelling, high cross-linked polystyrene are advantageous due to their compatibility with oligonucleotide synthesis, precluding the necessity to cleave and reattach the oligonucleotide.

The probe may be attached to the solid support through a variety of structures and synthetic routes. For example, the probe may be attached to the solid support by attachment of the 3' or 5' hydroxyl of the terminal nucleotide of the probe to the solid support. In other embodiments, the probe is attached to the solid support through a nucleobase, a sugar, or an internucleotide linkage. In one embodiment, the solid support is used as the synthesis support in preparing the fluorescent/quencher oligonucleotide probe. For oligonucleotide synthesis, the linker arm can be attached to the 3'-OH of the 3'-terminus by an ester linkage which can be cleaved with basic reagents to free the oligonucleotide from the solid support.

A wide variety of linkers are known in the art which may be used to attach the oligonucleotide probe to the solid support. The linker should not significantly interfere with the hybridization of the target sequence to the probe attached to the solid support. The linker may be formed of a non-target complementary oligonucleotide which can be readily added on to the linker by automated synthesis. Alternatively, polymers such as functionalized polyethylene glycol can be, used as the linker. Polyethylene glycol is commercially available, soluble in both organic and aqueous media, easy to functionalize, and stable under oligonucleotide synthesis and post-synthesis conditions. The linker between the solid support and the probe is preferably not cleaved during removal of base protecting groups under basic conditions at high temperature. These linkers can, however, be selected from groups that are cleavable under a variety of conditions. Exemplary linkers include carbamate and amide functionality.

V.7 KITS

The invention includes kits comprising polynucleotides labelled with quencher moieties of structures I or II, and other reagents such as nucleotide 5'-triphosphates, polymerase, primers, a detectable probe, and buffer. Such kits are useful in primer extension, hybridization assay, and 5' nuclease "TaqMan®" PCR detection assay. The kits may further comprise one or more target polynucleotides, or standard/control polynucleotides.

In another embodiment, the kits are useful for coupling fluorescence quencher compositions of the invention to polynucleotides and polypeptides. Such kits generally comprise a fluorescence quencher composition with a reactive linking group, e.g. a phosphoramidite or active ester, and any activator, coupling agent, buffer, solvent, or other reagent necessary to effect coupling to a polynucleotide or polypeptide. One such kit may contain a fluorescence quencher on solid-support and other reagents for the synthesis of a 3'-quencher labelled polynucleotide.

V.8 EXAMPLES

The invention having been described, the following Examples are offered by way of illustration, and not limitation.

Example 1

Synthesis of Ethyl 4-[(2,5-dimethoxyphenyl)ethylamino]butanoate 4

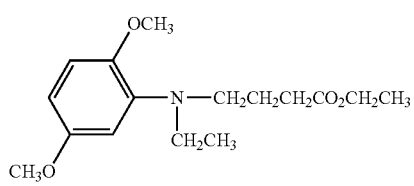

2,5-Dimethoxyaniline 1 (7.7 gm, 0.050 moles) was dissolved in 40 ml tetrahydrofuran (THF) and chilled to 0° C. under argon. Acetic anhydride (7.72 ml, 0.082 moles) was added. After stirring for 2 hours, thin-layer chromatography (TLC) indicated the reaction was complete. The mixture was evaporated under reduced pressure and kept under vacuum overnight.

Crude 2,5-dimethoxyacetanilide 2 was dissolved in 80 ml THF and stirred under argon. Borane-methylsulfide complex (62.5 ml, 2.0M in THF, 0.125 moles) was added by syringe over 10 minutes. After 10 minutes at ambient temperature, the mixture was heated to reflux for 3 hours. Analysis by TLC showed only a trace of 2. After cooling to room temperature, 42 ml water was cautiously added with stirring, followed by 4.5 ml conc. HCl. The reaction was heated for 1 hour. Next added sequentially with vigorous stirring were 125 ml water, 250 ml dichloromethane (DCM), and 16.6 ml 10N NaOH. The mixture was extracted with three 100 ml portions of DCM which were combined, dried over $Na_2SO_4$, and filtered. After concentration by rotary evaporation under reduced pressure, the crude product was purified by flash chromatography on silica gel, eluting with a gradient mixture of ethyl acetate and hexane. (2,5-Dimethoxyphenyl)ethylamine 3 (8.33 gm, 91% yield) was isolated after removing the solvent as a colorless liquid.

(2,5-Dimethoxyphenyl)ethylamine 3 (8.33 gm, 0.046 moles), ethyl 4-bromobutyrate (11.64 gm, 0.060 moles) and diisopropylethylamine (7.76 gm, 0.060 moles) were stirred at 110-120° C. for 18 hours, cooled, and partitioned between 50 ml DCM and 50 ml water. The aqueous layer was extracted thrice with 50 ml portions of DCM. The combined organic extracts were washed with saturated NaCl, dried over $Na_2SO_4$, filtered, and concentrated by rotary evaporation under reduced pressure. The crude product was purified by flash chromatography on silica gel, eluting with a gradient mixture of ethyl acetate and hexane. Ethyl 4-[(2,5-dimethoxyphenyl)ethylamino]butanoate 4 (12.73 gm, 94% yield) was isolated after removing the solvent. $^1$H NMR (CDCl$_3$) δ 6.44-6.78, 3H, m; 4.11, 2H, q; 3.79, 3H, s; 3.76, 3H, s; 3.08-3.19, 4H, m; 2.30, 2H, t; 1.79, 2H, m; 1.24, 3H, t; 1.03, 3H, t.

Example 2

Synthesis of Ethyl 4-(ethylphenylamino)butanoate 6

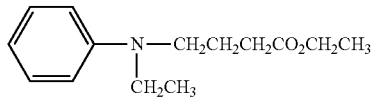

6

N-ethylaniline 5 (2.0 gm, 0.016 moles), triethylamine (5.0 ml, 0.036 moles), and ethyl 4-bromobutyrate (3.45 gm, 0.018 moles) were heated at 110° C. for 14 hours under argon. The mixture was cooled to room temperature, diluted with 50 ml ethyl acetate, washed with 50 ml water and 50 ml saturated NaCl, dried over MgSO$_4$, filtered, and evaporated under reduced pressure to give crude ethyl 4-(ethylphenylamino) butanoate 6 (3.0 gm, 77% yield). $^1$H NMR (CDCl$_3$) δ 7.2, 2H, m; 6.6; 3H, m; 4.15, 2H, q; 3.3, 4H, m; 2.38, 2H, t; 1.9, 2H, m; 1.25, 3H, t; 1.10, 3H, t.

Example 3

Synthesis of Methyl 2-(ethylphenylamino)acetate 7

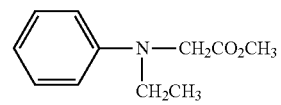

7

N-Ethylaniline 5 (2 g, 16.52 mmol) was added to a stirred suspension of sodium hydride (436 mg, 18.17 mmol) in DMF (20 ml) at ambient temperature under argon. After 45 minutes, bromomethyl acetate (3.02 g, 18.17 mmol) was added and the reaction mixture was stirred for 22 hr. DMF was removed under reduced pressure and the residue was treated with ethyl acetate (60 ml) and water (50 ml). The organic extract was washed with saturated brine (50 ml), dried (Na$_2$SO$_4$), filtered and evaporated to give crude Methyl 2-(ethylphenylamino) acetate 7 as liquid (3.06 g, 96%).

Example 4

Synthesis of Ethyl 4-(ethylnaphthylamino)butanoate 9

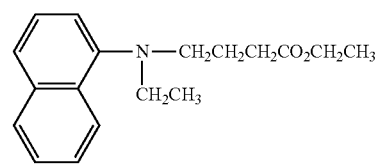

9

N-Ethyl-1-naphthylamine 8 (11.4 gm, 0.066 moles), diisopropylethylamine (11.2 gm, 0.087 moles), and ethyl 4-bromobutyrate (19 gm, 0.097 moles) were heated at 110-120° C. for 16 hours under argon at which time, HPLC indicated the reaction was complete. The mixture solidified upon cooling to room temperature. The solid was partitioned between DCM and water. The aqueous layer was extracted with two portions of DCM. The combined organic extracts were washed with saturated NaCl, dried over MgSO$_4$, filtered, concentrated under reduced pressure by rotary evaporation to give 22 gm of a crude solid. The solid was purified by flash chromatography, eluting with ethyl acetate and hexane, to give ethyl 4-(ethylnaphthylamino)butanoate 9 (6.04 gm, 32% yield) as an orange oil. $^1$H NMR (CDCl$_3$) δ 8.3, 1H, m; 7.8, 1H, m; 7.35-7.55, 4H, m; 7.15, 1H, m; 4.05, 2H, q; 3.18, 4H, m; 2.32, 2H, t; 1.8, 2H, m; 1.20, 3H, t; 1.05, 3H, t.

NMR (CDCl$_3$) δ 7.12, 1H, t; 6.31, 1H, d; 6.22, 2H, m; 4.12, 2H, q; 3.79, 3H, s; 3.3, 4H, m; 2.35, 2H, t; 1.9, 2H, m; 1.26, 3H, t; 1.14, 3H, t.

Example 5

Synthesis of Ethyl 4-[ethyl(3-methoxyphenyl)amino]butanoate 15

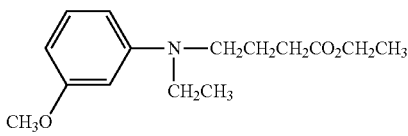

Example 6

Synthesis of Ethyl 4-[(2,5-dimethylphenyl)ethylamino]butanoate 19

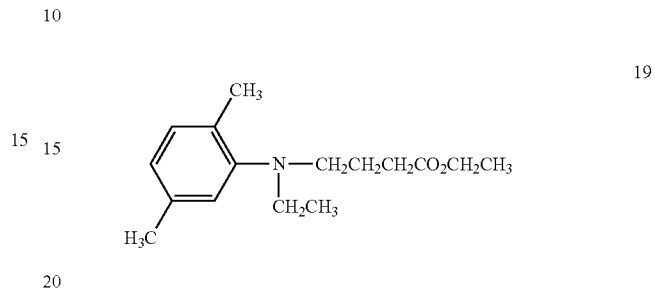

3-Methoxyaniline 12 (5 gm, 0.041 moles) was dissolved in 30 ml tetrahydrofuran (THF) at room temperature under argon. Acetic anhydride (5.8 ml, 0.061 moles) was added. After stirring for 2 hours, the mixture was evaporated under reduced pressure, dissolved in several mls of toluene and purified by flash chromatography on silica gel, eluting with a mixture of ethyl acetate and hexane. 3-Methoxyacetanilide 13 (6.63 gm, 99% yield) was isolated after removing the solvent. $^1$H NMR (CDCl$_3$) δ 7.6, 1H, br; 7.2, 2H, m; 6.95, 1H, d; 6.66, 1H, d; 3.78, 3H, s; 2.16, 3H, s.

3-Methoxyacetanilide 13 (6.63 gm, 0.040 moles) was dissolved in 65 ml THF and stirred under argon. Borane-methylsulfide complex (52 ml, 2.0 M, 0.10 moles) was added by syringe over 10 minutes. After 10 minutes at ambient temperature, the mixture was heated to reflux for 3 hours. After cooling to room temperature, 40 ml water was cautiously added with stirring over 10 minutes, followed by 3.6 ml conc. HCl. After heating for 30 minutes, 100 ml DCM and 67 ml 2N NaOH were added sequentially with vigorous stirring. An emulsion resulted which was eventually separated. The aqueous portion was extracted with three 50 ml portions of DCM which were combined, dried over MgSO$_4$, and filtered. After concentration by rotary evaporation under reduced pressure, the crude product was purified by flash chromatography on silica gel, eluting with a gradient mixture of ethyl acetate and hexane. (3-Methoxyphenyl)ethylamine 14 (5.73 gm, 93% yield) was isolated after removing the solvent as a colorless oil. NMR (CDCl$_3$) δ 7.07, 1H, t; 6.15-6.28, 3H, m; 3.76, 3H, s; 3.13, 2H, q; 1.23, 3H, t.

(3-Methoxyphenyl)ethylamine 14 (5.73 gm, 0.038 moles), ethyl 4-bromobutyrate (9.60 gm, 0.049 moles) and diisopropylethylamine (6.40 gm, 0.050 moles) were heated at 110-120° C. overnight, cooled, and partitioned between 100 ml DCM and 100 ml water. The aqueous layer was extracted twice with 50 ml portions of DCM. The combined organic extracts were washed with saturated NaCl, dried over Na$_2$SO$_4$, filtered, and concentrated by rotary evaporation under reduced pressure. The crude product was purified by flash chromatography on silica gel, eluting with a gradient mixture of ethyl acetate and hexane. Ethyl 4-[ethyl(3-methoxyphenyl)amino]butanoate 15 (9.6 gm, 95% yield) was isolated as a slightly yellow oil after removing the solvent. $^1$H 2,5-Dimethylaniline 16 (5.0 gm, 0.041 moles) was dissolved in 30 ml tetrahydrofuran (THF) at room temperature under argon. Acetic anhydride (5.9 ml, 0.062 moles) was added. Within 15 minutes, solids formed and the mixture became a solid white mass after 1 hour. Methanol was added which dissolved the mass. The mixture was evaporated under reduced pressure, dissolved in hot DCM and purified by flash chromatography on silica gel, eluting with a mixture of methanol and DCM. 2,5-Dimethylacetanilide 17 (6.67 gm, 99% yield) was isolated after removing the solvent. NMR (CDCl$_3$) δ 7.53, 1H, br s; 6.89-7.06, 3H, m; 2.30, 3H, s; 2.19, 3H, s; 2.17, 3H, s.

2,5-Dimethylacetanilide 17 (6.67 gm, 0.041 moles) was dissolved with heating in 65 ml THF and stirred under argon. The solution was cooled to room temperature and borane-methylsulfide complex (52 ml, 2.0M, 0.10 moles) was added by syringe over 10 minutes. After 10 minutes at ambient temperature, the mixture was heated to reflux for 3 hours. After cooling to room temperature, 40 ml water was cautiously added with stirring over 10 minutes, followed by 3.6 ml conc. HCl. After heating for 30 minutes, 100 ml DCM and 67 ml 2N NaOH were added sequentially with vigorous stirring. An emulsion resulted which was eventually separated. The aqueous portion was extracted with three 50 ml portions of DCM which were combined, dried over MgSO$_4$, and filtered. After concentration by rotary evaporation under reduced pressure, the crude product was purified by flash chromatography on silica gel, eluting with a gradient mixture of ethyl acetate and hexane. (2,5-Dimethylphenyl)ethylamine 18 (5.36 gm, 88% yield) was isolated after removing the solvent as a colorless oil. $^1$H NMR (CDCl$_3$) δ 6.92, 1H, d; 6.63, 2H, m; 3.18, 2H, q; 2.29, 3H, s; 2.08, 3H, s; 1.29, 3H, t.

(2,5-Dimethylphenyl)ethylamine 18 (5.36 gm, 0.036 moles), ethyl 4-bromobutyrate (9.11 gm, 0.046 moles) and diisopropylethylamine (6.07 gm, 0.047 moles) were heated at 110-120° C. overnight, cooled, and partitioned between 100 ml DCM and 100 ml water. The aqueous layer was extracted twice with 50 ml portions of DCM. The combined organic extracts were washed with saturated NaCl, dried over Na$_2$SO$_4$, filtered, and concentrated by rotary evaporation under reduced pressure. The crude product was purified by flash chromatography on silica gel, eluting with a gradient mixture of methanol and DCM. Ethyl 4-[(2,5-dimethylphenyl)ethylamino]butanoate 19 (4.66 gm, 49% yield) was isolated as a slightly yellow oil after removing the solvent. $^1$H NMR (CDCl$_3$) δ 7.07, 1H, d; 6.88, 1H, br s; 6.79, 1H, d; 4.10, 2H, q; 2.9, 4H, m; 2.35, 2H, t; 2.29, 3H, s; 2.24, 3H, s; 1.74, 2H, m; 1.24, 3H, t; 0.98, 3H, t.

Example 7

Synthesis of [3-(Ethylamino)-4-methoxyphenyl]dimethylamine 27

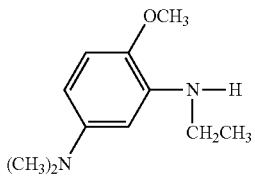

2-Methoxy-5-nitroaniline 23 (13.17 gm, 0.078 moles) was dissolved in 60 ml tetrahydrofuran (THF) at room temperature under argon. Acetic anhydride (11.1 ml, 0.118 moles) was added. An orange solution was formed. The mixture was evaporated under reduced pressure, and kept under vacuum overnight to give N-(2-Methoxy-5-nitrophenyl)acetamide 24 ($^1$H NMR (CDCl$_3$) δ 9.20, 1H, br s; 7.99, 1H, d; 6.95, 1H, d; 4.02, 3H, s; 3.12, 1H, s; 2.26, 3H, s), which was suspended in 115 ml ethanol. 5% Palladium on carbon (8.05 gm) was added, followed by the slow addition of 8.05 ml hydrazine hydrate (1 ml/5 minutes). After 90 minutes of heating, TLC indicated the reduction was complete. The mixture was filtered and the cake was washed with six 100 ml portions of methanol. The combined filtrate was concentrated under reduced pressure, taken up in 100 ml methanol and filtered again through Celite. The filtrate was concentrated to an oil and triturated with DCM and methanol to give crystals of N-(3-amino-6-methoxyphenyl)acetamide 25 (12.8 gm, 91% from 23) in two crops. $^1$H NMR (CDCl$_3$) δ 7.85, 1H, m; 7.80, 1H, br s; 6.67, 1H, d; 6.37, 1H, dd; 3.79, 3H, s; 3.5, 2H, br; 2.17, 3H, s.

N-(3-amino-6-methoxyphenyl)acetamide 25 (1.0 gm, 0.0055 moles) was dissolved in 30 ml DCM at room temperature under argon with stirring. Diisopropylethylamine (4.83 ml, 0.028 moles) and dimethylsulfate (2.36 ml, 0.025 moles) were added. After stirring at room temperature for 8 hours, 30 ml DCM and 40 ml 0.3 N NaOH were added. The mixture was partitioned and the aqueous layer was washed with three 30 ml portions of DCM. The combined organic extract was washed with saturated NaCl, dried over MgSO$_4$, filtered, and concentrated to give N-(3-dimethylamino-6-methoxyphenyl)acetamide 26 (0.57 gm, 50%). $^1$H NMR (CDCl$_3$) δ 8.01, 1H, m; 7.75, 1H, br s; 6.79, 1H, d; 6.43, 1H, dd; 3.82, 3H, s; 2.89, 6H, s, 2.19; 3H, s.

N-(3-dimethylamino-6-methoxyphenyl)acetamide 26 (0.10 gm, 0.48 mmoles) was dissolved in 2 ml THF and stirred under argon at room temperature. Borane-methylsulfide complex (0.6 ml, 2.0M, 1.2 mmoles) was added by syringe. After 10 minutes at ambient temperature, the mixture was heated to reflux for 3 hours. After cooling to room temperature, 0.6 ml water was cautiously added with stirring 0.1 ml conc. HCl. After heating for 1 hour, 5 ml DCM and 0.3 ml 2N NaOH were added sequentially with vigorous stirring. The aqueous portion was extracted with three 30 ml portions of DCM which were combined, dried over MgSO$_4$, filtered, and concentrated by rotary evaporation under reduced pressure to give 95 mg of crude [3-(ethylamino)-4-methoxyphenyl]dimethylamine 27.

Example 8

Synthesis of Diazo-diaryl compound 39

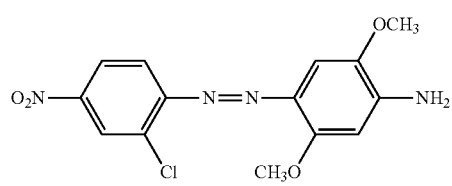

In a first flask, crushed 2-chloro-4-nitrophenylamine 10 (6.25 gm, 0.036 moles) was suspended in 110 ml water at 0° C. and 10.8 ml conc. HCl was added. After 10 minutes, NaNO$_2$ (2.57 gm, 0.037 moles) in 20 ml water was added over 10 minutes.

After stirring at 0° C. for one hour, 420 mg sulfuric acid (0.004 mole) in 5 ml water was added to the reaction solution. The reaction solution was directly filtered through a fritted funnel, collecting and retaining the filtrate.

To a one-liter three neck flask with overhead stirring was added 2,5-dimethoxyaniline 1 (5.73 gm, 0.037 moles), 500 ml water, and 3.6 ml conc. HCl. The mixture was heated to 80° C. to achieve a yellow solution. The solution was cooled to 0° C. and the filtrate from the first flask containing the diazonium compound was added. The thick orange-brown suspension was stirred at 0° C. for 2 hours. After adding 20 ml 10 N NaOH, the reaction was stirred for 5 minutes during which it became a homogeneous purple. The mixture was extracted exhaustively with DCM. The combined organic extracts were dried over MgSO$_4$, filtered, concentrated under reduced pressure and triturated with methanol and DCM to give crystals of diazo-diaryl compound 39 (11.85 gm, 97%).

Example 9

Synthesis of Diazo-diaryl compound 61

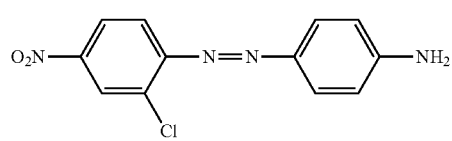

Following the procedure of Example 8, 2-chloro-4-nitrophenylamine 10 (1.21 gm, 7.0 mmoles) was diazotized and reacted with aniline (0.67 gm, 7.2 mmoles) to give diazo-diaryl compound 61 (1.48 gm, 76%). ¹H NMR (CDCl₃) δ 9.97, 1H, br s; 8.31, 1H, d; 8.17, 1H, d; 7.83, 1H, d; 7.63, 1H, d; 7.4, 3H, m.

Example 10

Synthesis of Diazo-diaryl compound 72

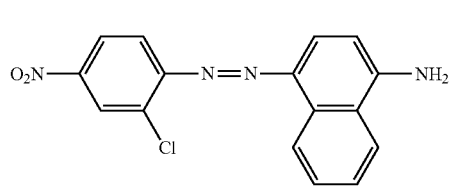

Following the procedure of Example 8, 2-chloro-4-nitrophenylamine 10 (1.21 gm, 7.0 mmoles) was diazotized and reacted with 1-aminonaphthalene (1.03 gm, 7.2 mmoles) to give diazo-diaryl compound 72 (1.48 gm, 76%).

Example 11

Synthesis of Diazo-diaryl compound 62

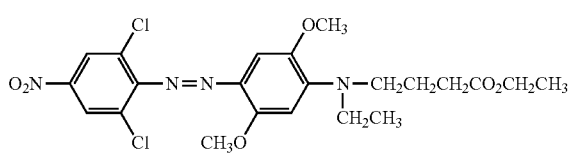

Following the procedure of Example 13, 2,6-dichloro-4-nitrophenylamine 28 (0.57 gm, 2.73 mmoles) was diazotized and reacted with ethyl 4-[(2,5-dimethoxyphenyl)ethylamino]butanoate 4 (0.765 gm, 2.6 mmoles) to give diazo-diaryl compound 62 (0.55 gm, 41%). ¹H NMR (CDCl₃) δ 8.24, 2H, s; 7.38, 1H, s; 6.50, 1H, s; 4.13, 2H, q; 4.01, 3H, s; 3.85, 3H, s; 3.44, 4H, m; 2.36, 2H, m; 1.98, 2H, m; 1.27, 3H, t; 1.24, 3H, t. Absorbance max. 474 nm (methanol.

Example 12

Synthesis of Diazo-diaryl Compound 57

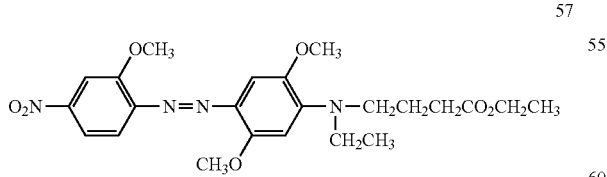

Following the procedure of Example 8, 2-methoxy-4-nitrophenylamine 23 (0.40 gm, 2.4 mmoles) was diazotized and reacted with ethyl 4-[(2,5-dimethoxyphenyl)ethylamino]butanoate 4 (0.65 gm, 2.80 mmoles) to give diazo-diaryl compound 57 (0.71 gm, 68%). NMR (CDCl₃) δ 7.9, 2H, m; 7.69, 1H, d, 7.36, 1H, s, 6.52, 1H, s; 4.13, 2H, q; 4.08, 3H, s; 4.03, 3H, s; 3.87, 3H, s; 3.41, 4H, m; 2.35, 2H, t; 1.94, 2H, m; 1.26, 3H, t; 1.20, 3H, t. Absorbance max. 525 nm (methanol.

Example 13

Synthesis of Diazo-diaryl Ester Compound 42

2,4-Dinitroaniline (0.64 gm, 3.5 mmoles) was dried under vacuum with P₂O₅ and suspended in 3 ml acetic acid at room temperature under argon with stirring. Nitrosylsulfuric acid (40%, 0.75 ml, 3.8 mmoles) was added and stirred as a yellowish solution for 2 hours. The solution was cooled to 0° C. and ethyl 4-(ethylphenylamino)butanoate 6 (0.77 gm, 3.27 mmoles) in 2 ml acetic acid was added which caused an immediate dark red solution. After stirring at room temperature for 2.5 hours, 10 ml water was cautiously added, followed by 100 ml DCM, 10 ml 2 N NaOH, and approximately 14.5 gm of solid sodium carbonate. The mixture was transferred to a separatory funnel, shaken, and the organic phase was removed. The aqueous phase was extracted twice with 50 ml DCM. The combined organic extracts was washed with saturated sodium chloride, dried over Na₂SO₄, filtered, and concentrated under reduced pressure. The crude product was purified by silica gel chromatography, eluting with ethyl acetate and hexane, to give diazo-diaryl ester 42 (0.92 gm, 66%) after removal of solvent. Abs. max. 519 nm (methanol). ¹H NMR (CDCl₃) δ 8.68, 1H, s; 8.41, 1H, d; 7.9, 2H, m; 6.88, 1H, d; 4.15, 2H, q; 3.5, 4H, m; 2.40, 2H, t; 1.98, 2H, m; 1.29, 3H, t; 1.26, 3H, t.

Example 14

Synthesis of Diazo-diaryl Ester 47

Following the procedure of Example 13, 2,4-dinitroaniline (0.51 gm, 2.8 mmoles) and ethyl 4-[(2,5-dimethoxyphenyl) ethylamino]butanoate 4 (0.765 gm, 2.59 mmoles) were converted to diazo-diaryl ester 47 (0.48 gm, 38%). Abs. max. 563 nm (methanol). ¹H NMR (CDCl₃) δ 8.62, 1H, s; 8.38, 1H, d;

7.93, 1H, d; 7.34, 1H, s; 6.42, 1H, s; 4.15, 2H, q; 4.04, 3H, s; 3.82, 3H, s; 3.5, 4H, m; 2.4, 2H, t; 2.0, 2H, m; 1.27, 3H, t; 1.26, 3H, t.

Example 15

Synthesis of Diazo-diaryl Acid 48

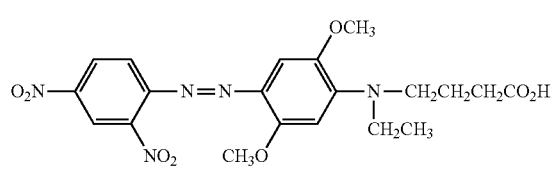

48

Diazo-diaryl ester 47 (480 mg, 0.98 mmole) was stirred at room temperature in 6 ml THF. Lithium hydroxide hydrate (0.164 gm, 3.9 mmoles) in 3 ml water was added. The mixture was stirred overnight, then 10 ml 1 N acetic acid/sodium acetate buffer (pH 5.0) was added. The mixture was extracted with three portions of DCM. The combined organic extract was washed with saturated NaCl, dried over $Na_2SO_4$, filtered, and concentrated under vacuum. The crude product was purified by silica gel chromatography to give diazo, diaryl acid 48 (0.324 gm, 72%) after removal of solvent. Absorbance max. 568 nm (methanol); 587 nm (0.1M TEAA). $^1H$ NMR ($CD_3OD$) δ 8.68, 1H, s; 8.39, 1H, d; 7.95, 1H, d; 7.33, 1H, s; 6.42, 1H, s; 4.03, 3H, s; 3.82, 3H, s; 3.5, 4H, m; 2.4, 2H, t; 1.98, 2H, m; 1.26, 3H, t.

Example 16

Synthesis of Diazo-diaryl Ester 46

46

Following the procedure of Example 13, 2,4-dinitroaniline (0.51 gm, 2.8 mmoles) and ethyl 4-(ethylnaphthylamino)butanoate 9 (0.739 gm, 2.59 mmoles) were converted to diazo-diaryl ester 46 (0.58 gm, 47%). Abs. max. 515 nm (methanol). $^1H$ NMR ($CDCl_3$) δ 8.90, 1H, d; 8.67, 1H, s; 8.41, 1H, d; 8.17, 1H, d; 7.96, 2H, m; 7.6, 2H, dt; 7.13, 1H, d; 4.10, 2H, q; 3.45, 4H, m; 2.38, 2H, t; 1.94, 2H, m; 1.22, 3H, t; 1.19, 3H, t.

Example 17

Synthesis of Diazo-diaryl Ester 43

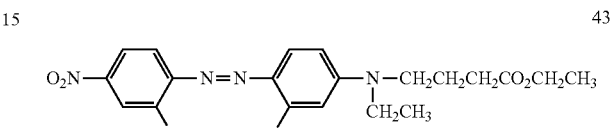

43

Following the procedure of Example 13, 2,4-dinitroaniline (0.51 gm, 2.8 mmoles) and ethyl 4-[ethyl(3-methoxyphenyl)amino]butanoate 15 (0.69 gm, 2.59 mmoles) were converted to diazo-diaryl ester 43 (0.49 gm, 41%). Abs. max. 537 nm (methanol). $^1H$ NMR ($CDCl_3$) δ 8.62, 1H, s; 8.35, 1H, d; 7.8, 2H, dd; 6.38, 1H, d; 6.30, 1H, s; 4.09, 2H, q; 4.05, 3H, s; 3.5, 4H, m; 2.4, 2H, m; 1.28, 3H, t; 1.27, 3H, t.

Example 18

Synthesis of Diazo,diaryl Acid 44

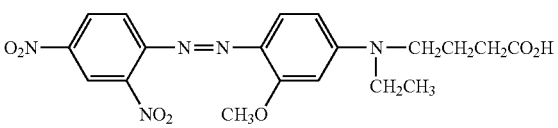

44

Following the procedure of Example 15, diazo-diaryl ester 43 (420 mg, 0.91 mmole) was stirred at room temperature in 6 ml THF. Lithium hydroxide hydrate (0.153 gm, 3.6 mmoles) in 3 ml water was added. The mixture was stirred overnight, then 10 ml 1 N acetic acid/sodium acetate buffer (pH 5.0) was added. The mixture was extracted with three portions of DCM. The combined organic extract was washed with saturated NaCl, dried over $Na_2SO_4$, filtered, and concentrated under vacuum. The crude product was purified by silica gel chromatography to give diazo,diaryl acid 44 (0.346 gm, 88%) after removal of solvent. Absorbance max. 537 nm (methanol); 556 nm (0.1M TEAA).

Example 19

Synthesis of Diazo-diaryl Ester 45

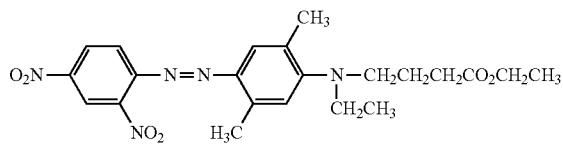

45

Following the procedure of Example 13, 2,4-dinitroaniline 11 (0.51 gm, 2.8 mmoles) and Ethyl 4-[(2,5-dimethylphenyl)ethylamino]butanoate 19 (0.68 gm, 2.59 mmoles) were converted to diazo-diaryl ester 45 (0.22 gm, 19%). Abs. max. 479 nm (THF), 469 nm (methanol). $^1$H NMR (CDCl$_3$) δ 8.66, 1H, s; 8.42, 1H, d; 7.80, 1H, d; 7.56, 1H, s; 6.89, 1H, s; 4.12, 2H, q; 3.20, 4H, m; 2.67, 3H, s; 2.32, 2H, m; 2.27, 3H, s; 1.86, 2H, m; 1.25, 3H, t; 1.11, 3H, t.

Example 20

Synthesis of Diazo-diaryl Ester 49

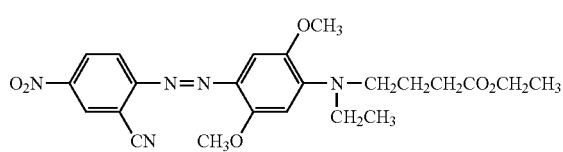

49

Following the procedure of Example 13, 2-amino-5-nitrobenzonitrile 20 (0.45 gm, 2.73 mmoles) and ethyl 4-[(2,5-dimethoxyphenyl)ethylamino]butanoate 4 (0.765 gm, 2.59 mmoles) were converted to diazo-diaryl ester 49 (0.27 gm, 22%). Abs. max. 574 nm (methanol). $^1$H NMR (CDCl$_3$) δ 8.57, 1H, s; 8.38, 1H, d; 7.94, 1H, d; 7.56, 1H, s; 6.41, 1H, s; 4.15, 2H, q; 4.05, 3H, s; 3.86, 3H, s; 3.5, 4H, m; 2.39, 2H, t; 2.0, 2H, m; 1.27, 6H, t.

Example 21

Synthesis of Diazo,diaryl Acid 50

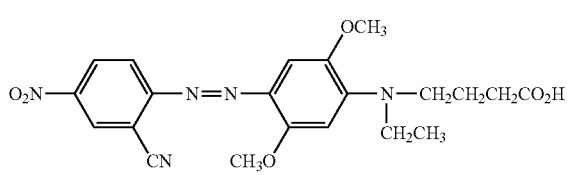

50

Following the procedure of Example 15, diazo-diaryl ester 49 (145 mg, 0.31 mmole) was stirred at room temperature in 4 ml THF. Lithium hydroxide hydrate (52 mg, 1.2 mmoles) in 1.5 ml water was added. The mixture was stirred overnight, then 10 ml 1N acetic acid/sodium acetate buffer (pH 5.0) was added. The mixture was extracted with three portions of DCM. The combined organic extract was washed with saturated NaCl, dried over Na$_2$SO$_4$, filtered, and concentrated under vacuum. The crude product was purified by silica gel chromatography to give diazo,diaryl acid 50 (112 mg, 82%) after removal of solvent. Abs. max. 577 nm (methanol), 584 nm (0.1M TEAA).

Example 22

Synthesis of Bis-diazo,triaryl PFP Ester 51

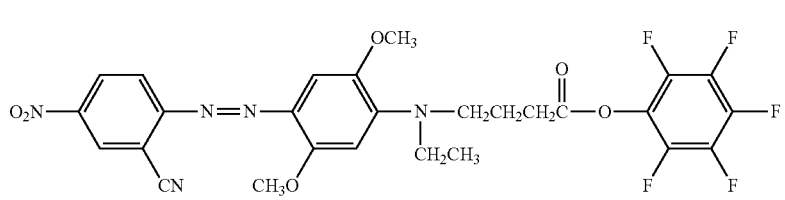

51

Diazo,diaryl acid 50 (106 mg, 0.24 mmoles) was suspended in 2.5 ml DCM at room temperature under argon with stirring. Triethylamine (67 µl, 0.5 mmoles) and pentafluorophenyl trifluoroacetate (53 µl, 0.31 mmoles) and the mixture was stirred overnight. The mixture was concentrated under vacuum and purified by silica gel chromatography, eluting with ethyl acetate and hexane to give the bis-diazo, triaryl PFP ester 51 (117 mg, 80%) after removal of solvent. $^1$H NMR (CDCl$_3$) δ 8.55, 1H, s; 8.38, 1H, d; 7.95, 1H, d; 7.54, 1H, s; 6.39, 1H, s; 4.02, 3H, s; 3.88, 3H, s; 3.56, 4H, m; 2.78, 2H, t; 2.15, 2H, m; 1.27, 3H, t; 1.30, 3H, t.

Example 23

Synthesis of Diazo-diaryl Ester 52

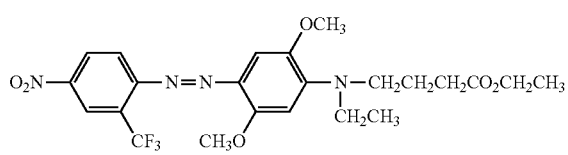

Following the procedure of Example 13, 4-nitro-2-(trifluoromethyl)-aniline 21 (0.56 gm, 2.73 mmoles) and ethyl 4-[(2,5-dimethoxyphenyl)ethylamino]butanoate 4 (0.765 gm, 2.59 mmoles) were converted to diazo-diaryl ester 52 (0.47 gm, 35%). Abs. max. 549 nm (methanol). $^1$H NMR (CDCl$_3$) δ 8.62, 1H, s; 8.39, 1H, d; 7.95, 1H, d; 7.44, 1H, s, 6.42, 1H, s; 4.15, 2H, q; 4.05, 3H, s; 3.84, 3H, s; 3.49, 4H, m; 2.37, 2H, t; 198, 2H, m; 1.27, 3H, t; 1.24, 3H, t.

Example 24

Synthesis of Diazo,diaryl Acid 53

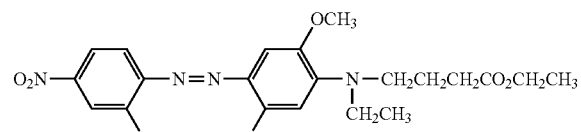

Following the procedure of Example 15, diazo-diaryl ester 52 (230 mg, 0.45 mmole) was stirred at room temperature in 4 ml THF. Lithium hydroxide hydrate (75 mg, 1.8 mmoles) in 1.5 ml water was added. The mixture was stirred overnight, then 10 ml 1N acetic acid/sodium acetate buffer (pH 5.0) was added. The mixture was extracted with three portions of DCM. The combined organic extract was washed with saturated NaCl, dried over Na$_2$SO$_4$, filtered, and concentrated under vacuum. The crude product was purified by silica gel chromatography to give diazo,diaryl acid 53 (221 mg, 100%) after removal of solvent. Abs. max. 550 nm (methanol), 556 nm (0.1M TEAA).

Example 25

Synthesis of Diazo-diaryl Ester 54

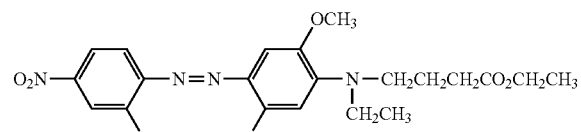

Following the procedure of Example 8, 2-chloro-4-nitrophenylamine 10 (0.21 gm, 1.2 mmoles) and ethyl 4-[(2,5-dimethoxyphenyl)ethylamino]butanoate 4 (0.325 gm, 1.1 mmoles) were converted to diazo-diaryl ester 54 (0.43 gm, 81%). Abs. max. 538 nm (methanol). $^1$H NMR (CDCl$_3$) δ 8.38, 1H, s; 8.15, 1H, d; 7.78, 1H, d; 7.44, 1H, s; 6.46, 1H, s; 4.15, 2H, q; 4.04, 3H, s; 3.86, 3H, s; 3.46, 4H, m; 2.37, 2H, t; 1.98, 2H, m; 1.27, 3H, t; 1.23, 3H, t.

Example 26

Synthesis of Diazo,diaryl Acid 55

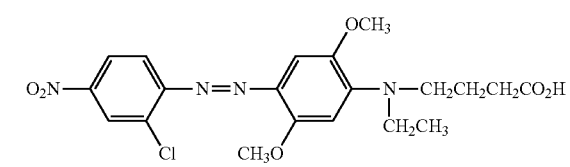

Following the procedure of Example 15, diazo-diaryl ester 54 (385 mg, 0.80 mmole) was stirred at room temperature in 6 ml THF. Lithium hydroxide hydrate (134 mg, 3.2 mmoles) in 3 ml water was added. The mixture was stirred overnight, then 10 ml 1 N acetic acid/sodium acetate buffer (pH 5.0) was added. The mixture was extracted with three portions of DCM. The combined organic extract was washed with saturated NaCl, dried over Na$_2$SO$_4$, filtered, and concentrated under vacuum. The crude product was purified by silica gel chromatography to give diazo,diaryl acid 55 (197 mg, 55%) after removal of solvent. Abs. max. 543 nm (methanol), 554 nm (0.1M TEAR).

Example 27

Synthesis of Diazo-diaryl Ester 56

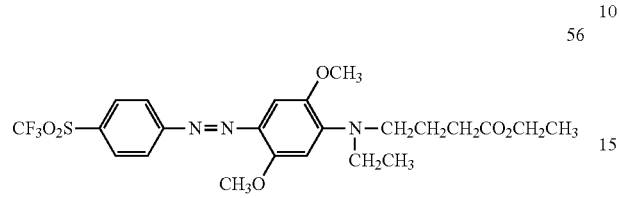

Following the procedure of Example 8, 4-(trifluoromethylsulfonyl)aniline 22 (0.27 gm, 1.2 mmoles) and ethyl 4-[(2,5-dimethoxyphenyl)ethylamino]butanoate 4 (0.325 gm, 1.1 mmoles) were converted to diazo-diaryl ester 56 (0.43 gm, 73%). Abs. max. 519 nm (methanol). $^1$H NMR (CDCl$_3$) δ 8.05, 4H, dd; 7.42, 1H, s; 6.51, 1H, s; 4.13, 2H, q; 4.04, 3H, s; 3.87, 3H, s; 3.45, 4H, m; 2.37, 2H, t; 1.99, 2H, m; 1.24, 3H, t; 1.22, 3H, t.

Example 28

Synthesis of Bis-diazo,triaryl Compound 40

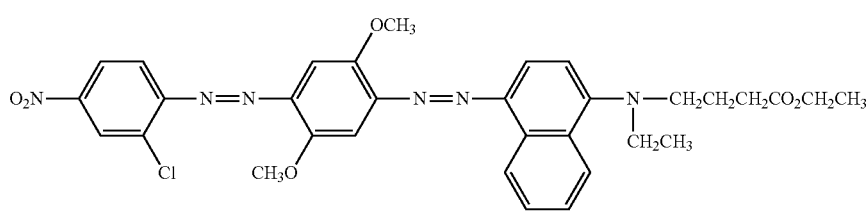

A mixture of ethyl 4-(ethylnaphthylamino)butanoate 9 (611 mg, 2.14 mmoles) and diazo,diaryl compound 39 (793 mg, 2.35 mmoles) in 42 ml DMF and 0.6 ml conc. HCl was stirred vigorously at room temperature under argon. After 10 minutes, NaNO$_2$ (403 mg, 5.8 mmoles) in 4.3 ml water was added as a 0.5 ml aliquot every 15 minutes. When addition was complete, the dark brown solution was stirred another hour, then partitioned between 60 ml DCM and 30 ml 1 N acetic acid. The aqueous layer was extracted with two 20 ml portions of DCM. The combined organic extracts were combined, dried over MgSO$_4$, filtered, and concentrated under reduced pressure. The residue was purified by silica gel chromatography, eluting with a gradient of ethyl acetate and hexane, then methanol and DCM to give bis-diazo,triaryl 40 (690 mg, 51%) after removal of solvent as a purple solid. Abs. max. 553 nm (methanol). $^1$H NMR (CDCl$_3$) δ 9.0, 1H, d; 8.43, 1H, s; 8.2, 2H, m; 7.9, 2H, dd; 7.6, 4H, m; 7.20, 1H, d; 4.15, 3H, s; 4.05, 3H, s; 3.6, 4H, m; 2.35, 2H, t; 1.9, 2H, m; 1.6, 2H, m; 1.22, 3H, t; 1.06, 3H, t.

Example 29

Synthesis of Diazo-diaryl Compound 63

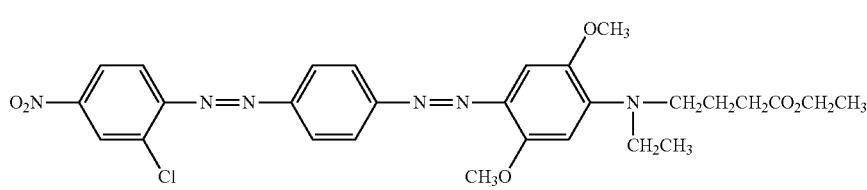

Following the procedure of Example 28, diazo-diaryl 61 (650 mg, 2.35 mmoles) was diazotized and reacted with ethyl 4-[(2,5-dimethoxyphenyl)ethylamino]butanoate 4 (632 mg, 2.14 mmoles) to give diazo-diaryl compound 63 (0.34 gm, 27%). $^1$H NMR (CDCl$_3$) δ 8.35, 1H, s; 8.1, 2H, m, 7.78, 2H, d; 7.57, 1H, s; 7.46, 1H, s; 6.47, 2H, d; 4.15, 2H, q; 4.04, 3H, s; 3.96, 3H, s; 3.47, 4H, m; 2.35, 2H, m; 1.98, 2H, m; 1.27, 3H, t; 1.26, 3H, t. Absorbance max. 539 nm (methanol).

Example 30

Synthesis of Diazo-diaryl Compound 64

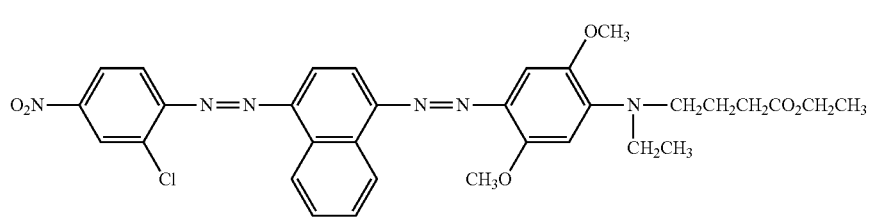

64

Following the procedure of Example 28, diazo-diaryl 72 (768 mg, 2.35 mmoles) was diazotized and reacted with ethyl 4-[(2,5-dimethoxyphenyl)ethylamino]butanoate 4 (632 mg, 2.14 mmoles) to give diazo-diaryl compound 64 (0.17 gm, 12%). Absorbance max. 582 nm (methanol).

Example 31

Synthesis of Bis-diazo,triaryl Compound 31 from Fast Black K Salt 29

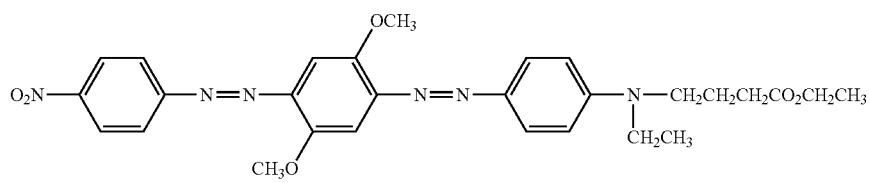

31

Fast Black K salt 29 (Aldrich, Abs. max. (methanol) 330+ 416 nm, 14.0 gm, 33.9 mmoles) was dissolved in 40 ml acetic acid and 10 ml water at 0° C. under argon with stirring. Ethyl 4-(ethylphenylamino)butanoate 6 (8.0.0 gm, 33.9 mmoles) dissolved in 5 ml acetic acid was added.

After one hour, the mixture was allowed to rise to room temperature and stirring was continued overnight. The solution was adjusted to pH 4 with 1N NaOH, causing precipitation of the crude product. The precipitate was dissolved in acetone filtered through Celite, concentrated under reduced pressure and purified by silica gel chromatography, eluting with ethyl acetate and hexane. Bis-diazo,triaryl compound 31 (9.0 gm, 45%) was isolated after removal of solvent.

Example 32

Synthesis of Bis-diazo,triaryl Compound 31 from 38

Following the procedure of Example 28, 2,5-dimethoxy-4-[(4-nitrophenyl)diazenyl]phenylamine 38 (0.50 gm, 2.14 mmoles) was diazotized and reacted with ethyl 4-(ethylphenylamino)butanoate 6 (0.79 gm, 2.38 mmoles) to give bis-diazo,triaryl 31 (950 mg, 76%).

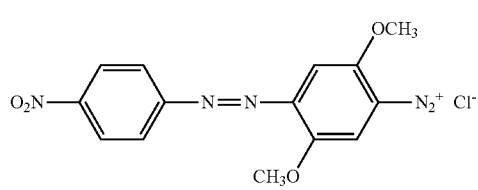

29

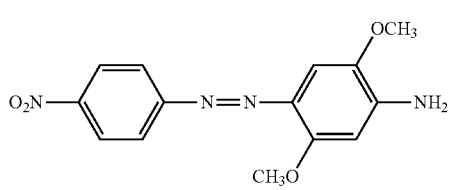

38

Example 33

Synthesis of Bis-diazo,triaryl Compound 30

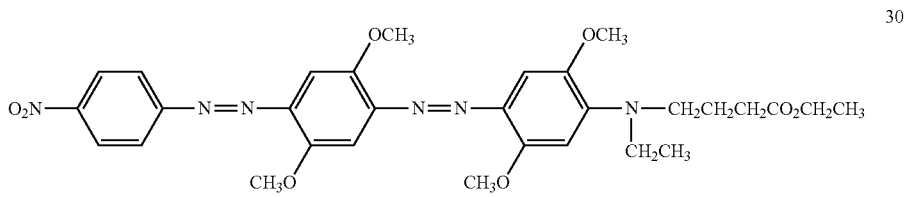

Tetramethoxy bis-diazo,triaryl compound 30 is prepared from Fast Black K salt 29 and ethyl 4-[(2,5-dimethoxyphenyl)ethylamino]butanoate 4 (Example 1) by the procedure of Example 31.

Example 34

Synthesis of Quencher-NHS Compound 36

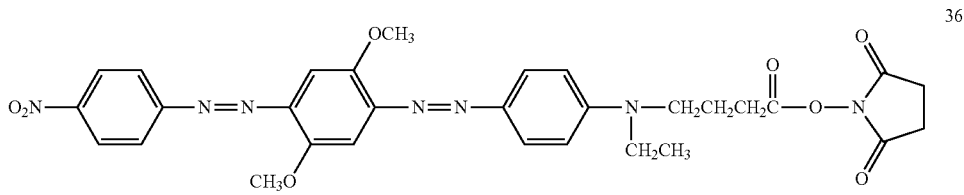

Bis-diazo,triaryl compound 31 (2.40 gm, 4.74 mmoles) was mixed with lithium hydroxide hydrate (2.00 gm, 47 mmoles), 80 ml THF, and 20 ml water at room temperature for 26 hours. The mixture was concentrated under vacuum and partitioned between 200 ml ethyl acetate and 100 ml water and acidified with 0.5 N HCl. The organic extract was concentrated under reduced pressure, dried over $Na_2SO_4$, filtered, concentrated to give a dark blue solid which was purified by silica gel chromatography, eluting with 1% acetic acid in ethyl acetate to give bis-diazo,triaryl acid 34 after removal of solvent.

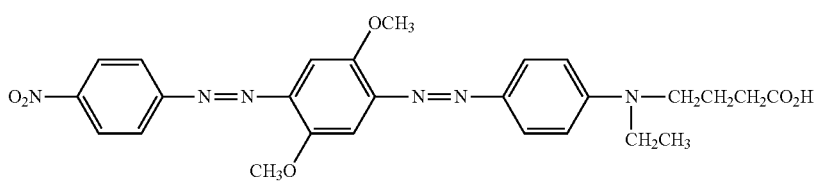

A mixture of bis-diazo,triaryl acid 34 (80 mg, 0.16 mmoles), EDC (62 mg, 0.32 mmoles), N-hydroxysuccinimide (22 mg, 0.19 mmoles) and 10 ml DMF was stirred for 18 hours at room temperature under argon. The mixture was concentrated under reduced pressure, dissolved in ethyl acetate and washed with two 40 ml portions of sat. NaCl. The organic extract was dried over $Na_2SO_4$, filtered, and evaporated to give quencher-NHS 36 as a dark blue solid (60 mg).

Example 35

Synthesis of Bis-diazo, Triaryl Acid 41

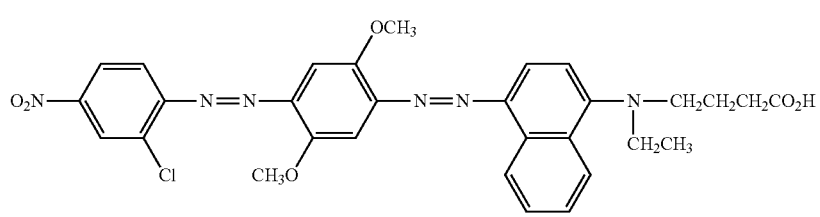
41

The ethyl ester of bis-diazo,triaryl 40 (460 mg, 0.73 mmole) was hydrolyzed by the procedure in Example 15 to give bis-diazo, triaryl acid 41.

Example 36

Synthesis of Bis-diazo, Triaryl Compound 32

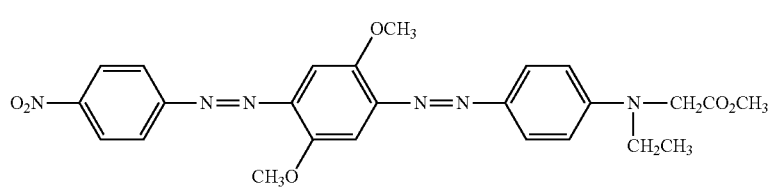
32

Fast Black K salt 29 (Aldrich, Abs. max. (methanol) 330+ 416 nm, 1.0 gm, 2.39 mmoles) was dissolved in 15 ml acetic acid and 5 ml water at 0° C. under argon with stirring. Methyl 2-(ethylphenylamino)acetate 7 (0.462 gm, 2.39 mmoles) dissolved in 2 ml acetic acid was added. After one hour, the mixture was allowed to rise to room temperature and stirring was continued overnight. The solution was neutralized with a slight excess of conc. $NH_4OH$, causing precipitation of the crude product. The precipitate was dissolved in 70 ml ethyl acetate, dried over $MgSO_4$, filtered, concentrated under reduced pressure and purified by silica gel chromatography, eluting with ethyl acetate and hexane. Bis-diazo,triaryl compound 32 (0.504 gm, 40%) was isolated after removal of solvent. Absorbance max. (methanol) 540 nm. Exact mass by mass spectroscopy: 506.19133, MW 506.51700 ($C_{25}H_{26}N_6O_6$).

Example 37

Synthesis of Bis-diazo,triaryl Compound 70

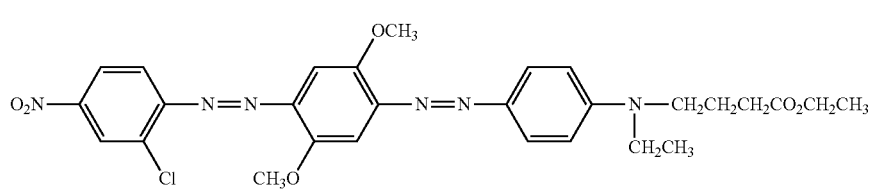
70

Following the procedure of Example 28, a mixture of ethyl 4-(ethylphenylamino)butanoate 6 (0.50 gm, 2.14 mmoles) and diazo,diaryl compound 39 (793 mg, 2.35 mmoles) in 42 ml DMF and 0.6 ml conc. HCl was stirred vigorously at room temperature under argon. After 10 minutes, NaNO$_2$ (403 mg, 5.8 mmoles) in 4.3 ml water was added as a 0.5 ml aliquot every 15 minutes. When addition was complete, the dark brown solution was stirred another hour, then partitioned between 60 ml DCM and 30 ml 1 N acetic acid. The aqueous layer was extracted with two 20 ml portions of DCM. The combined organic extracts were combined, dried over MgSO$_4$, filtered, and concentrated under reduced pressure. The residue was purified by silica gel chromatography, eluting with a gradient of ethyl acetate and hexane, then methanol and DCM to give bis-diazo,triaryl 70 (950 mg, 76%) after removal of solvent as a blue-purple solid. Absorbance max. (methanol) 569 nm. $^1$H NMR (CDCl$_3$) δ 8.40, 1H, s; 8.18, 1H, d; 7.9, 2H, d; 7.8, 1H, d; 7.55, 1H, s; 7.42, 1H, s; 6.78, 1H, d; 4.18, 2H, q; 4.09, 3H, s; 4.04, 3H, s; 3.5, 4H, m; 2.4, 2H, t; 2.0, 2H, m; 1.29, 3H, t; 1.27, 3H, t.

Example 38

Synthesis of Bis-diazo,triaryl Acid 60

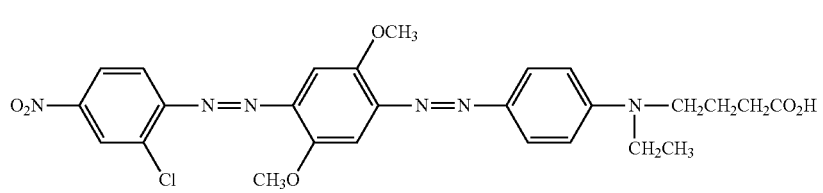

The ethyl ester of bis-diazo,triaryl 70 (950 mg, 1.63 mmole) was hydrolyzed by the procedure in Example 15 to give bis-diazo, triaryl acid 60 (527 mg, 58%) as a blue solid. Absorbance max. 571 nm (methanol); 487 nm (0.1M TEAA). NMR (CDCl$_3$) δ 8.42, 1H, s; 8.20, 1H, d; 7.94, 2H, d; 7.82, 1H, d; 7.55, 1H, s; 7.43, 1H, s; 6.78, 2H, d; 4.10, 3H, s; 4.04, 3H, s; 3.5, 4H, m; 2.42, 2H, m; 2.0, 2H, m; 1.25, 3H, t.

Example 39

Synthesis of Bis-diazo,triaryl Compound 71

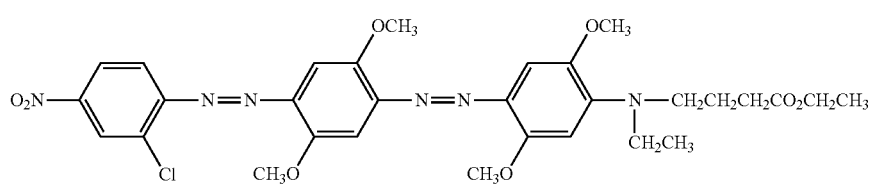

Following the procedure of Example 28, diazo,diaryl compound 39 (793 mg, 2.35 mmoles) and ethyl 4-[(2,5-dimethoxyphenyl)ethylamino]butanoate 4 (632 mg; 2.14 mmoles) were reacted to give bis-diazo,triaryl compound 71 as a blue solid (470 mg, 34%). Absorbance max. (methanol) 592 nm. $^1$H NMR (CDCl$_3$) δ 8.62, 1H, s; 8.2, 1H, d; 7.82, 1H, d; 7.54, 1H, s; 7.4, 2H, s; 6.52, 1H, s; 4.10, 3H, s; 4.06, 3H, s; 4.04, 3H, s; 3.89, 3H, s; 3.8, 2H, m; 3.40, 4H, m; 2.38, 2H, t; 1.9, 2H, m; 1.26, 3H, t; 1.21, 3H, t.

Example 40

Synthesis of Bis-diazo,triaryl PFP Ester 59

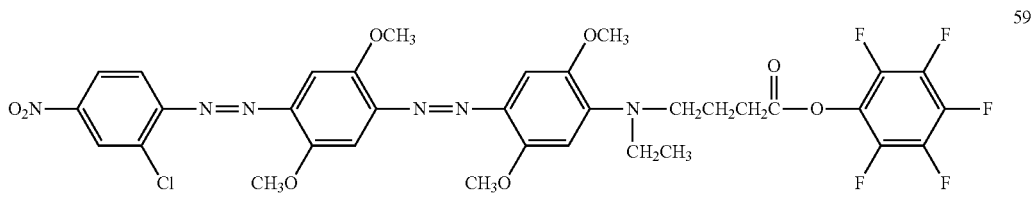

Following the procedure of Example 15, the ethyl ester of bis-diazo,triaryl compound 71 (470 mg, 0.73 mmoles) was hydrolyzed to give bis-diazo,triaryl acid 58 (275 mg, 61%) as a blue solid. Absorbance max. 601 nm (methanol); 553 nm (0.1M TEAA). $^1$H NMR (CDCl$_3$) δ 8.42, 1H, s; 8.20, 1H, d; 7.82, 1H, d; 7.57, 1H, s; 7.40, 2H, s; 6.55, 1H, s; 4.10, 3H, s; 4.04, 3H, s; 4.03, 3H, s; 3.88, 3H, s; 3.4, 4H, m; 2.75, 2H, t; 2.1, 2H, m; 1.23, 3H, t.

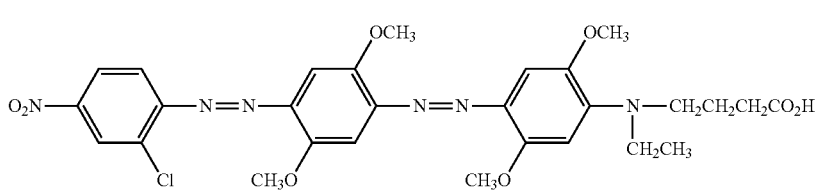

Following the procedure of Example 22, bis-diazo,triaryl acid 58 (261 mg, 0.42 mmoles) was suspended in 4 ml DCM at room temperature under argon with stirring. Triethylamine (0.12 ml, 0.86 mmoles) and pentafluorophenyl trifluoroacetate (0.094 ml, 0.55 mmoles) and the mixture was stirred overnight. The mixture was concentrated under vacuum and purified by silica gel chromatography, eluting with ethyl acetate and hexane to give the bis-diazo,triaryl PFP ester 59 (251 mg, 76%) after removal of solvent.

Example 41

Synthesis of Hydroxy Phenazonium Compound 73

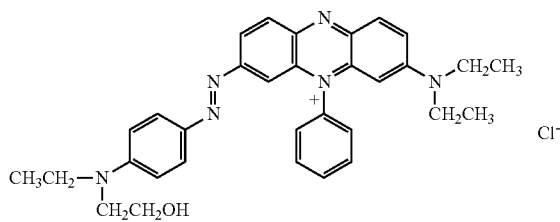

A solution of 3-amino-7-(diethylamino)-5-phenyl-phenazinium chloride 74 (Methylene violet 3RAX, Aldrich, 0.379 gm, 1.0 mmole) in 12 ml sulfolane (tetramethylene sulfone) and 4 ml CH$_3$CN was added to nitrosonium tetrafluoroborate (NOBF$_4$, 0.129 gm, 1.1 mmoles) dissolved in 4 ml sulfolane (tetramethylene sulfone) and 12 ml CH$_3$CN at 0° C. under argon with stirring.

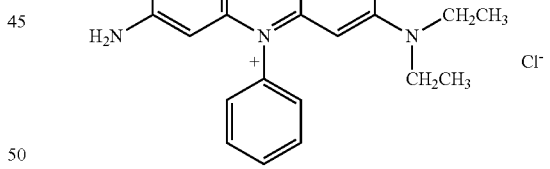

After stirring for 15 minutes, 2-(N-ethylanilino)ethanol (0.182 gm, 1.1 mmoles) was added. After stirring for 30 minutes, the mixture was poured into 120 ml 1N HCl. The crude product was purified by reverse phase HPLC to give hydroxy-phenazonium 73 (110 mg, 20%) as a blue solid. Absorbance max. (methanol) 662 nm. Exact mass by mass spectroscopy: 519.29; MW 519.66; C$_{32}$H$_{35}$N$_6$O. $^1$H NMR (CD$_3$OD) δ 7.5-8.2, 11H, m; 7.1, 1H, d; 6.7, 2H, dd; 5.7, 1H, d; 3.5-3.9, 10H, m; 1.2, 9H, m. $^{13}$C NMR (CD$_3$OD) δ 157.22, 156.65, 154.34, 144.93, 144.43, 140.37, 138.90, 137.17, 135.77, 134.71, 133.79, 133.03, 132.97, 128.82, 128.22, 124.79, 121.44, 113.17, 111.73, 93.24, 60.38, 53.68, 47.97, 47.88, 47.23, 12.64.

Example 42

Synthesis of Quencher Phosphoramidite Compound 75

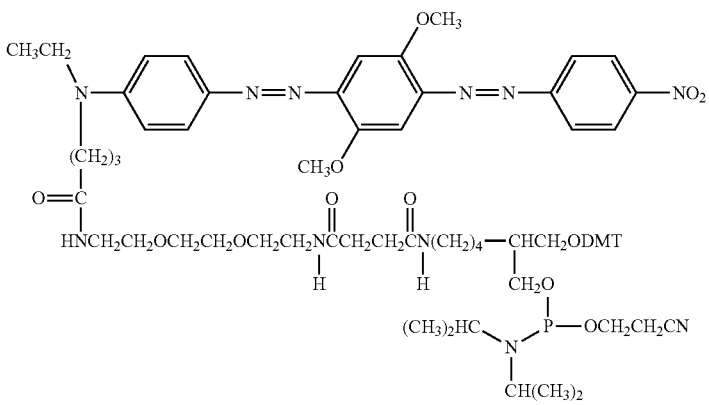

75

Quencher-NHS 36 is coupled with amino linker 76 to give hydroxyl quencher linker 77.

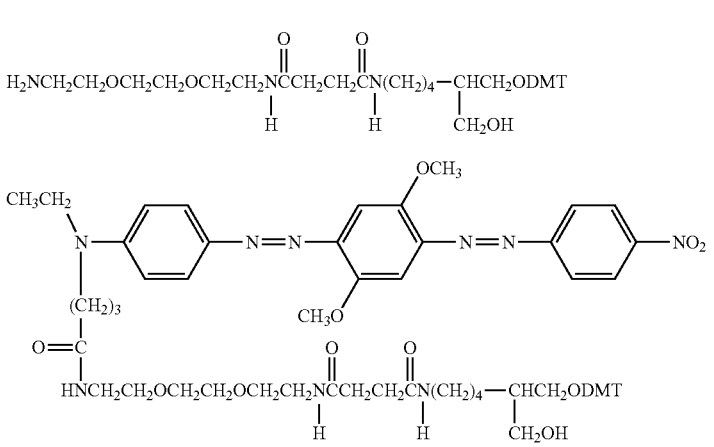

76

77

Hydroxyl-quencher compound 77 (1.97 gm, 1.67 mmoles) and diisopropylammonium 5-H-tetrazolide (0.337 gm, 1.69 mmoles) are dissolved in 55 ml DCM. 2-Cyanoethyl-N,N-tetraisopropyl phosphoramidite $((iPr_2N)_2$—P—$OCH_2CH_2CN$, 1.28 ml, 1.206 gm, 4.00 mmoles) was added. The solution was stirred at room temperature under argon overnight, then diluted with DCM, washed with saturated $NaHCO_3$ and saturated NaCl, dried over $Na_2SO_4$, filtered, and concentrated under reduced pressure. The crude product was purified by silica gel chromatography, eluting with acetone, triethylamine, and DCM to give quencher phosphoramidite 75 (2.30 gm, 85%) as a purple foam after removal of solvent. 31P NMR showed 99.5% purity.

Example 43

Synthesis of Hydroxyl Quencher Linker 77

Fmoc linker compound 82 (3 g, 4.46 mmol) was treated with tert-butyl dimethylsilyl chloride (807 mg, 5.35 mmol) and imidazole (425 mg, 6.24 mmol) in DMF (15 ml) at room temperature for 18 h. DMF was removed under reduced pressure. The residue was dissolved in 70 ml ethyl acetate and washed with 50 ml water and 50 ml saturated brine. The organic extract was dried over $Na_2SO_4$ and evaporated to give Fmoc silyl 83 as a sticky foam, which was treated with 20% piperidine in 70 ml DMF at ambient temperature for 8 h. The DMF and piperidine were removed under reduced pressure and the residual oil was applied to a silica gel column. The column was eluted with 0-5% methanol in DCM gradient. Appropriate fractions were combined and evaporated to give silyl-amino compound 84 as an oil (1.78 g, 70% yield).

A mixture of silyl-amino 84 (1.77 g, 3.13 mmol), succinic anhydride (408 mg, 4.08 mmol), triethylamine (474 mg, 4.69 mmol) and dimethylaminopyridine (191 mg, 1.56 mmol) in dichloromethane (20 ml) was stirred at ambient temperature for 18 h. The mixture was diluted with DCM (20 ml) and washed with 30 ml 5% aqueous citric acid solution and 30 ml saturated brine. The organic extract was dried over $Na_2SO_4$ and concentrated. The crude product was applied to a silica gel column and eluted with 5-10% methanol in DCM gradient. Appropriate fractions were combined and evaporated to give succinate amide ester 85 as a thick gum (1.78 g, 85%).

82

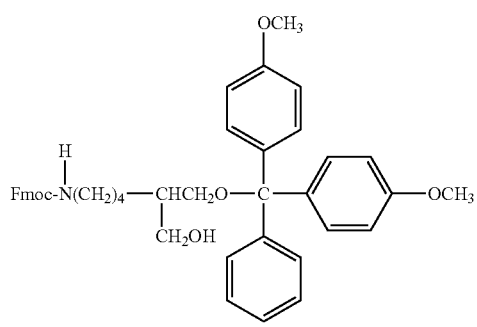

84

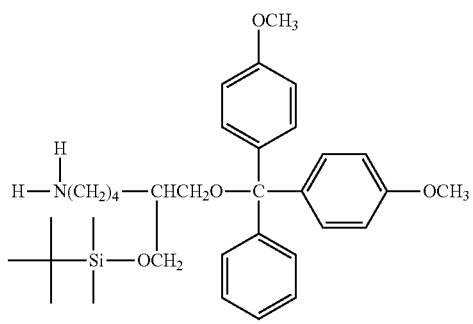

85

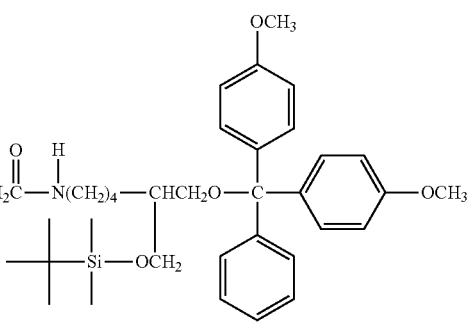

A solution of 79 (Example 48, 3.15 g, 4.59 mmol) in DCM (30 ml) was added to a stirred solution of 2,2'(ethylenedioxy) bis-ethylamine (6.78 g, 45.90 mmol) in 50 ml DCM at ambient temperature under argon. After 1 hour the mixture was washed with 40 ml water and 50 ml saturated brine. The organic extract was dried ($Na_2SO_4$) and concentrated and loaded on a silica gel column. The column was eluted with 5-15% methanol in DCM gradient containing 5% triethylamine. Appropriate fractions were combined and evaporated to give amino quencher 86 as purple foam (2.79 g, 93%).

83

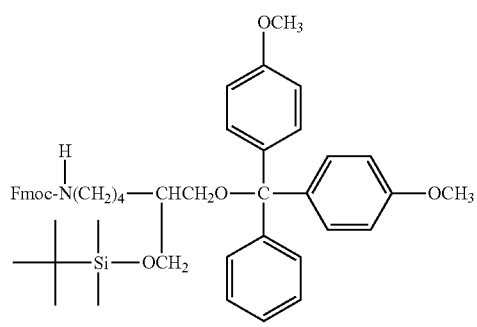

86

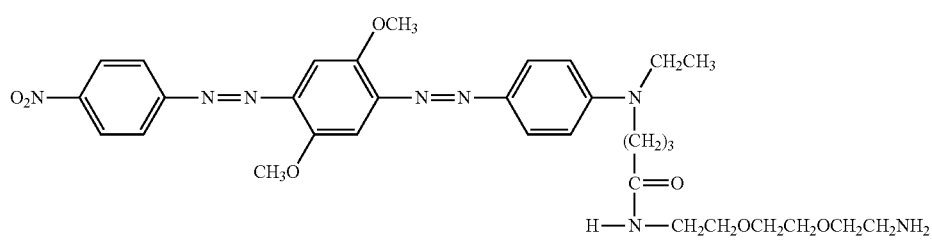

Diisopropylethyl amine (1.04 g, 8.04 mmol) and O-benzotriazol-1-yl-N,N,N',N'-tetramethyluronium hexafluorophosphate (1.02 g, 2.68 mmol) were added to a solution of succinate amide ester 85 (1.78 g, 2.68 mmol) and amino-quencher 86 (1.92 g, 2.94 mmol) in DMF (70 ml). The mixture was stirred at ambient temperature for 24 h. DMF was removed under reduced pressure. The residue was dissolved in DCM (100 ml) and washed with water (1×50 ml) and sat. brine (1×50 ml). The organic extract was dried (Na$_2$SO$_4$) and evaporated. The product was purified by silica gel column eluting with a 0-5% methanol in DCM gradient to give silyl 87 as a purple foam (3.2 g, 87%). Tetrabutylammonium fluoride (1M, 5 ml, 5 mmol) was added to a solution of silyl 87 (3.2 g, 2.46 mmol) in THF (50 ml) at ambient temperature. After 48 h THF was removed and the residue was dissolved in DCM (15 ml) and applied to a silica gel column. The column was eluted with 0-10% methanol in DCM gradient containing 2% triethylamine. Appropriate fractions were combined and evaporated to give 77 as a purple foam (2.4 g, 82%).

Hydroxy-quencher compound 81 (Example 48; 2.2 g, 2.31 mmol) and diisopropylammonium-5-H-tetrazole (230 mg, 1.15 mmol) dissolved in DCM (30 ml). 2-Cyanoethyl-N,N-tetraisopropyl phosphoramidite ((iPr$_2$N)$_2$P—OCH$_2$CH$_2$CN (1.04 g, 3.46 mmol) was added. The solution was stirred at ambient temperature under argon for 23 h. The solution was diluted with DCM (30 ml), washed with 10% NaHCO$_3$ and saturated brine, dried over Na$_2$SO$_4$, filtered and concentrated under reduced pressure. The crude product was purified by silica gel column eluting with 10-30% ethyl acetate in DCM containing 1% triethylamine. Appropriate fractions were combined and evaporated to give quencher phosphoramidite 88 as a purple foam (2.27 g, 84%). $^{31}$P NMR showed 99.5% purity.

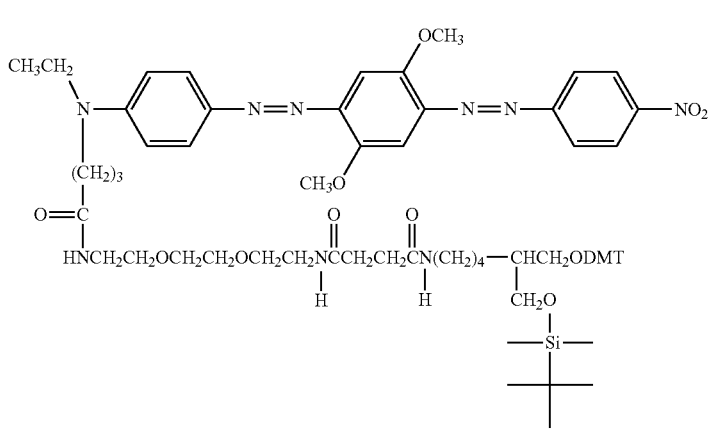

Example 44

Synthesis of Quencher Phosphoramidite Compound 88

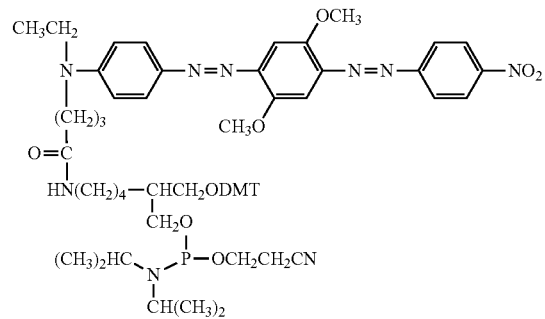

Example 45

Synthesis of Quencher-oligonucleotides with Quencher Phosphoramidite 88

5'Q-T$_5$ and 5' T$_2$-Q-T$_5$ 3' oligonucleotides were synthesized at the 0.2 µmole scale using quencher phosphoramidite 88, 3' phosphoramidite thymidine and 3' thymidine on polystyrene support in a synthesis column. Automated trityl monitoring showed 98.5% coupling efficiency for quencher phosphoramidite 88

Example 46

Synthesis of Quencher-support Compound 65 from 32

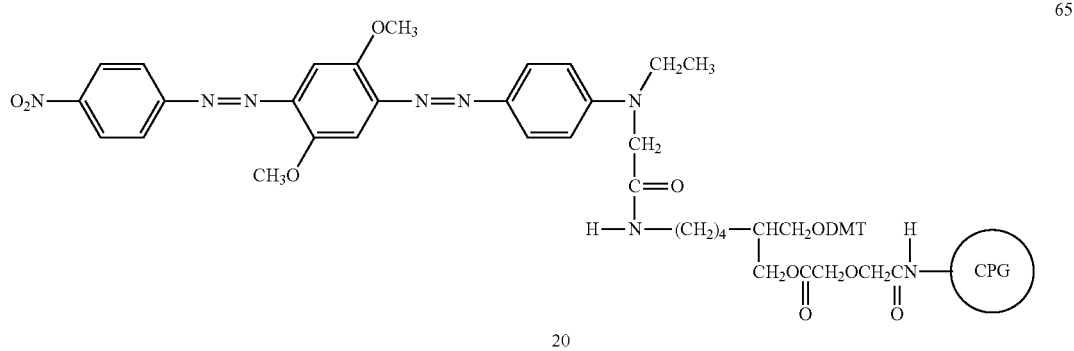

65

Bis-diazo,triaryl compound 32 (2.40 gm, 4.74 mmoles) was mixed with lithium hydroxide hydrate (2.00 gm, 47 mmoles), 80 ml THF, and 20 ml water at room temperature for 26 hours. The mixture was concentrated under vacuum and partitioned between 200 ml ethyl acetate and 100 ml water and acidified with 0.5 N HCl. The organic extract was concentrated under reduced pressure, dried over $Na_2SO_4$, filtered, concentrated to give a dark blue solid which was purified by silica gel chromatography, eluting with 1% acetic acid in ethyl acetate to give bis-diazo,triaryl acid 35 after removal of solvent. Abs. max: 548 nm, $\epsilon$ (extinction coefficient): 15,023; 260 nm, $\epsilon$: 4273 (methanol). Abs. max: 570 nm, $\epsilon$: 8062; 260 nm, $\epsilon$: 2160 (0.1M TEAA). Exact mass by mass spectroscopy: 492.17568, MW 492.49020 ($C_{24}H_{24}N_6O_6$).

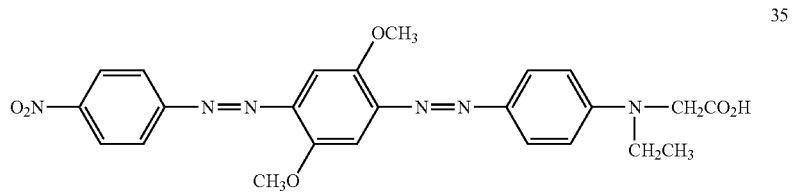

35

A mixture of O-benzotriazol-1-yl)-N,N,N',N'-tetramethyluronium hexafluorophosphate (HBTU, 20 mg, 52 µmoles), 1-hydroxybenzotriazole (HOBt, 7 mg, 52 µmoles), diisopropylethylamine (23 µl, 130 µmoles), bis-diazo,triaryl acid 35 (13 mg, 26 µmoles), amino, DMT, CPG support 66 (200 mg, 26 µmoles/gm, 5.2 µmoles),

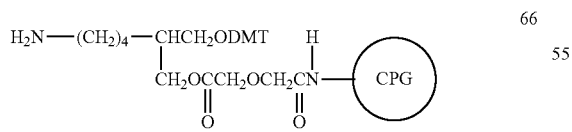

66 and 1.5 ml dimethylformamide (DMF) was shaken at room temperature for 24 hours (Mullah, U.S. Pat. No. 5,736,626). The support was washed with DMF, $CH_3CN$, and capped with a mixture of acetic anhydride, N-methylimidazole, pyridine, and THF for 45 minutes. The support was washed with $CH_3CN$ and DCM, and dried under vacuum to give quencher support 65. From HPLC analysis, the coupling yield of 35 to support 66 was measured at 78%.

Example 47

Synthesis of Quencher-support Compound 69 from Quencher-NHS 36

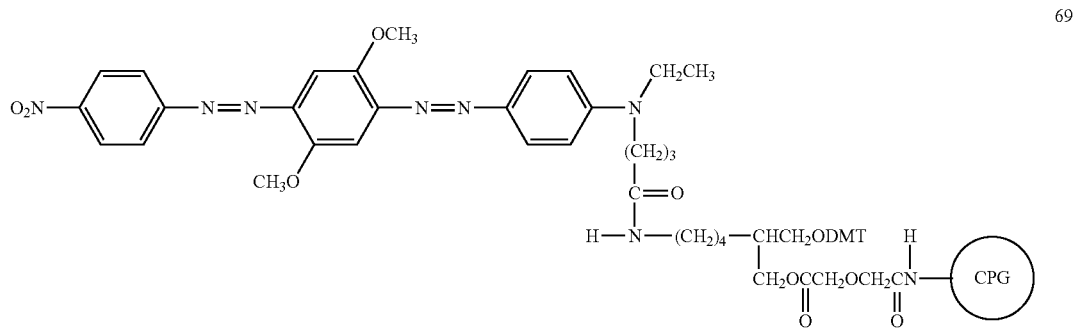

69

A mixture of quencher-NHS 36 (21 mg, 44 µmoles), amino, DMT, CPG support 66 (125 mg, 35 µmoles/gm, 4.4 µmoles), diisopropylethylamine (23 µl, 132 µmoles) and 1 ml DMF was shaken at room temperature for 25 hours. The support was washed with DMF, $CH_3CN$, and capped with a mixture of acetic anhydride, N-methyl imidazole, pyridine, and THF for 1 hour. The support was washed with $CH_3CN$ and DCM, and dried under vacuum to give quencher support 69. From HPLC analysis, the coupling yield of 36 to support 66 was measured at 90%.

Example 48

Synthesis of Quencher-support Compound 69 from Diglycolate Ester 80

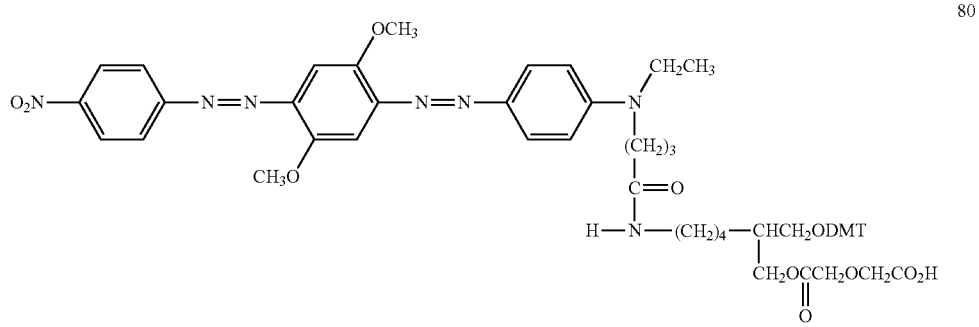

80

Diglycolic anhydride (85 mg, 0.73 mmol) was added to a mixture of compound 81 (500 mg, 0.52 mmol) and triethylamine (105 mg, 1.03 mmol) in DCM (15 ml) at 0° C. (ice bath). After 30 min the reaction mixture was transferred to ambient temperature and stirred for 2 h. The mixture was diluted with DCM (20 ml) and washed with 20 ml 5% aqueous citric acid solution. Triethylamine (0.5 ml) was added to the organic extract and the extract was dried over $Na_2SO_4$. Evaporation of solvent gave diglycolate ester 80 as a purple foam (triethylamine salt, 600 mg).

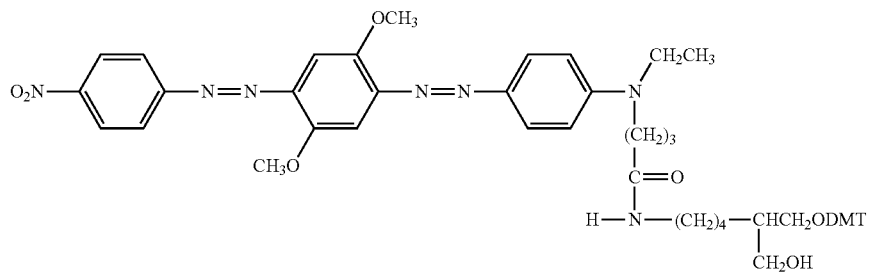

81

Hydroxyl-quencher 81 is prepared from a mixture of amino-DMT compound 78 (2.5 g, 5.39 mmol) and PFP ester 79 (4.07 g, 5.90 mmol) in DCM (60 ml), treated with triethylamine (1.09 g, 10.8 mmol) at ambient temperature for 16 h (overnight). PFP ester 79 was prepared from acid 34 by the procedure of Examples 22 and 40. The mixture was concentrated and applied to a silica gel column. The column was eluted with a 0-5% methanol in DCM containing 1% triethylamine. Fractions containing products were combined and evaporated to give hydroxyl-quencher 81 as a purple foam (4.65 g, 90%).

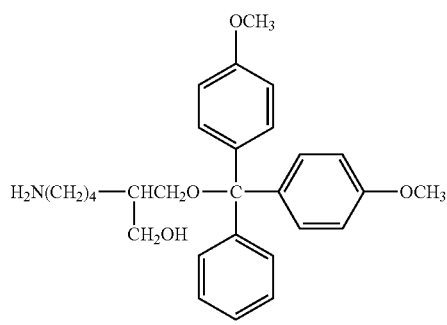

78

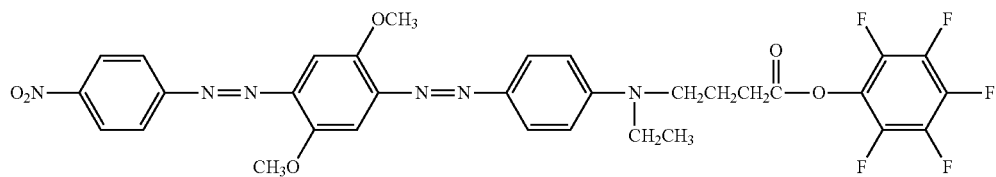

79

A mixture of 80 (428 mg, 450 μmol), aminopropyl CPG (5 g, 225 μmol amine per gram loading), diisopropylethylamine (87 mg, 675 μmol), HBTU (85 mg, 225 μmol) and DMF (12 ml) was shaken at ambient temperature for 23 h. The support was washed with DMF, THF, and capped with a mixture of acetic anhydride, N-methyl imidazole, pyridine and THF for 1 h. The support was washed with THF, $CH_3CN$ and DCM, and dried under vacuum. The dye loading was calculated from trityl assay to be 33.6 μmol/g.

Example 49

Synthesis of 3' Quencher-T₅ Oligonucleotide 68

SEQ ID NO: 1
5' F-CGC CTG GTC ACC AGG GCT GC-Q 3'

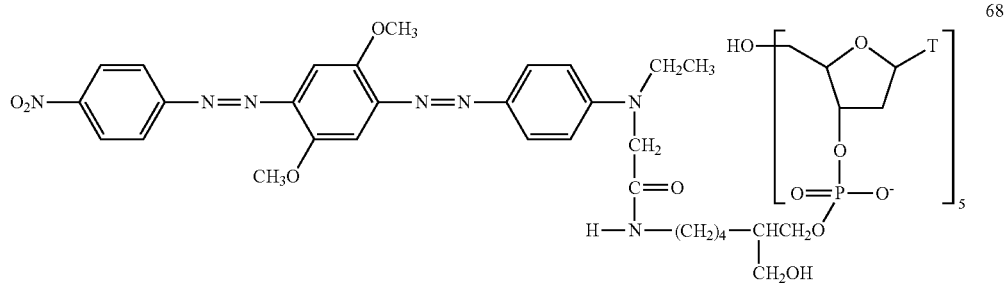

Quencher support 65 (Example 46, 8 mg, 200 nmoles) was loaded into a standard synthesis column and used to synthesize a $T_5$ oligonucleotide on an ABI 394 Synthesizer (Applied Biosystems, Foster City, Calif.) by five successive couplings of thymidine 3' cyanoethylphosphoramidite with the standard reagents, conditions, and cycle recommended and provided by the manufacturer (Applied Biosystems) to give about 8 odu (A260 nm) of approximately 58% pure, 3' quencher $T_5$ on CPG support 67:

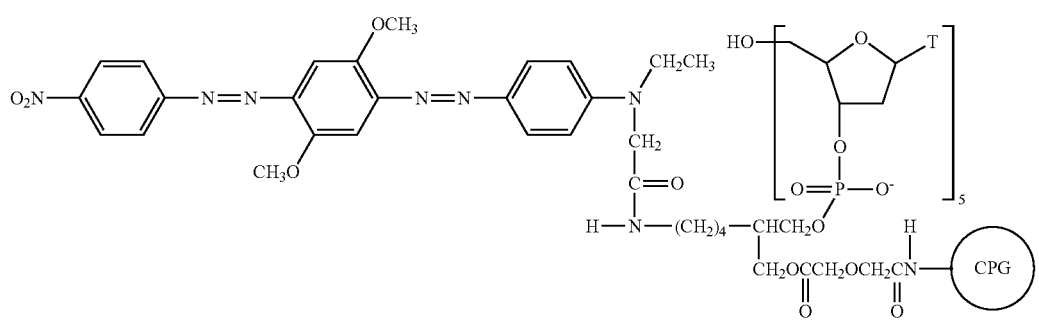

After cleavage of the diglycolate ester of 67 with conc. NH₄OH for 2 hours at room temperature, the mixture was filtered and the eluate containing about 8 odu (A260 nm) of 68 was dried under vacuum (Abs. max. 560 nm in 50 mM TEAA at pH 8.0) and analyzed by reverse phase HPLC, eluting with CH₃CN in aqueous TEAA (triethylamine acetate) to be 58% pure.

The corresponding 3' quencher-T₅ oligonucleotide synthesized from support 69 was prepared and analyzed by the same procedure above, in 78% purity (8 odu) using 69 prepared by the method of Example 47, and in 92% purity (9 odu) using 69 prepared by the method of Example 48.

Example 50

Synthesis of 3' Quencher, 5' Fluorescent Dye Oligonucleotides-GAPDH Probes

Four 3'-quencher, 5'-fluorescent dye oligonucleotides probes:

where F is a reporter dye and Q is a quencher moiety, were synthesized on an ABI 394 Synthesizer (Applied Biosystems) with 3' nucleoside cyanoethylphosphoramidites ($A^{bz}$, $G^{dmf}$, $C^{bz}$, T), ancillary reagents, cycle, and post-synthesis procedures recommended and provided by the manufacturer (Applied Biosystems) and in Mullah, U.S. Pat. No. 5,736,626. Syntheses were conducted on quencher support 69 (Example 48) at the 200 nmole scale. After addition of 3' nucleoside phosphoramidites to complete the sequence from 3' to 5', the last coupling was with each of the four fluorescent dye phosphoramidite reagents:

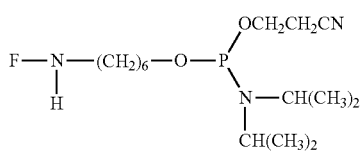

where F was one of $F_1$-$F_4$:

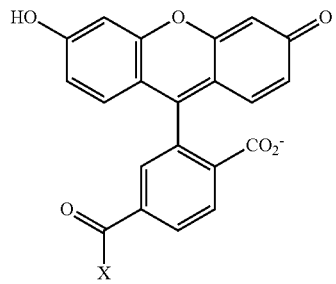
$F_1$

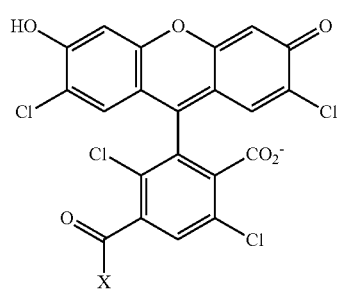
$F_2$

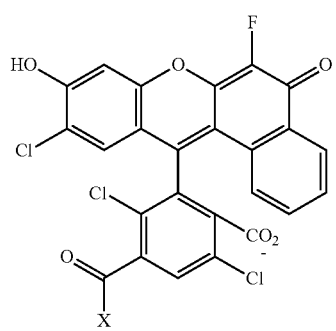
$F_3$

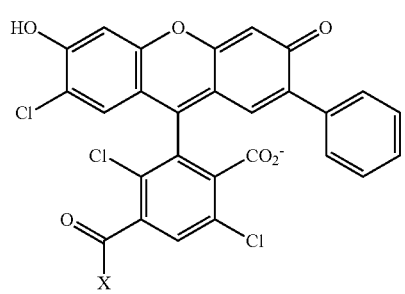
$F_4$ (Menchen, U.S. Pat. No. 5,188,934; Benson, U.S. Pat. Nos. 6,020,481 and 6,008,379) where X is the site of attachment to the nitrogen of the linker to form an amide bond and the phenolic oxygen atoms were protected as pivalate (tert-butyl) esters (Theisen (1992) "Fluorescent dye phosphoramidite labelling of polynucleotides", in *Nucleic Acid Symposium Series* No. 27, Oxford University Press, Oxford, pp. 99-100). The average yield per cycle was about 98%, as measured by trityl monitoring. The dual-labelled probes were cleaved from the CPG support, and the nucleobase and phosphate protecting groups were removed, with concentrated $NH_4OH$. Deprotection can also be accomplished with a mixture of tert-butylamine/methanol/water: 1/1/2. The crude probes were analyzed and purified by reverse phase HPLC.

Example 51

PCR Assay with 3'-Quencher, 5'-Fluorescent Dye GAPDH Probes

A 5' nuclease detection assay of PCR was conducted on the ABI Prism 7700 Sequence Detection System (Applied Biosystems) with the four dual-labelled probes of Example 50. PCR amplification reactions (50 μl) contained cDNA template nucleic acid from Raji cell RNA, 2× TaqMan universal Master mix (25 μl) including PCR buffer, dNTPs (dATP, dGTP, dCTP, TTP), and $MgCl_2$ (Applied Biosystems), AmpliTaq Gold DNA polymerase, forward (SEQ ID NO:2) and reverse (SEQ ID NO:3) primers:

```
Forward Primer:
                                 SEQ ID NO: 2
5' GGG AAG GTG AAG GTC GGA GTC 3'

Reverse Primer:
                                 SEQ ID NO: 3
5' CTG GAA GAT GGT GAT GGG ATT TC 3'
``` and a probe from Example 50, each at 100 nM final concentration. The target sequence was the GAPDH region. The thermal cycling protocol began with 2 min at 50° C. and 10 min at 95° C., then proceeded with 40 cycles of 95° C. for 15 sec and 60° C. for 1 min. Reaction conditions were programmed on a Power Macintosh G3 (Apple Computer, CA) linked directly to the ABI 7700 Sequence Detector. Analysis of data was also performed on a Macintosh computer with collection and analysis software (Applied Biosystems). Results of the real-time detection assay using Example 50 probes with the bis-diazo, triaryl quencher moiety (34) were compared with the same set of probes (SEQ ID NO:1) labelled with the same fluorescent dye reporters, $F_1$-$F_4$, but with TAMRA as the 3' quencher.

Example 52

Synthesis of Quencher-polypeptide with a Quencher-isothiocyanate Reagent

A procedure for labelling a polypeptide with a quencher-isothiocyanate is illustrated by the steps:
1. Prepare the polypeptide at 1-5 mg ml$^{-1}$ in 0.1 M NaHCO$_3$/Na$_2$CO$_3$ buffer, pH 8.5.
2. Prepare a solution of the quencher-isothiocyanate at 50 mM in DMSO and add to the protein to give a final concentration of 2 mM. Mix and allow to react overnight at room temperature in the dark.
3. De-salt the product, e.g. on a size-exclusion gel media cartridge, into the buffer of choice.
4. Characterize as follows: record absorbance spectrum at 1:20 dilution, blanked against the column buffer. Determine protein concentration by a standard method (e.g. Coomassie or BCA methods) allowing for carrier BSA if present, or from the spectrum.

Example 53

Synthesis of Quencher-polypeptide with a Quencher-NHS Reagent

A procedure for labelling a polypeptide, where the polypeptide is a relatively dilute protein (1 mg ml$^{-1}$), with a quencher-NHS ester is illustrated by the steps:

1. Prepare protein in 50 mM sodium phosphate, pH 7.5 at ca 1 mg ml$^{-1}$ (1.0 ml). Higher protein concentrations may be used.
2. Prepare a fresh 20 mM solution of quencher-NHS ester in DMSO, and add 20 μl of the reagent to the protein, stirring with the pipette tip during addition. Final reagent concentration is 0.4 mM. Allow to react at room temperature for 1 h.
3. Equilibrate a size exclusion gel media cartridge, e.g. Sephadex™ G25 (Pharmacia PD-10) with PBS containing 1 mg ml$^{-1}$ BSA (heat-treated for 30 mM at 56° C.). BSA is optional but helps improve protein recovery.
4. Stop reaction by addition of 1/10th volume of 0.1 M ethanolamine, pH 8.5 (0:1 ml) and allow to react for a further 10 min.
5. Apply the reaction to the equilibrated cartridge, followed by 1.8 ml buffer. Then add further 1.6 ml and collect the colored product band.
6. Characterize as follows: record absorbance spectrum at 1:20 dilution, blanked against the column buffer. Determine protein concentration by a standard method (e.g. Coomassie, or BCA) allowing for carrier BSA if present, or from the spectrum (less accurate if carrier protein is present) or assume a column recovery factor.
7. Store at 4° C. with 0.05% NaN$_3$ (away from light) or at -20° C.

Example 54

Synthesis of Fluorescein/Quencher-polypeptide

A general procedure for labelling a polypeptide with a quencher-NHS ester to prepare a fluorescein/quencher FRET protease substrate is illustrated by the steps:
1. Dissolve the polypeptide (having a free N-terminus, no other amines and a cysteine in 0.1 M NaH$_2$PO$_4$/Na$_2$HPO$_4$ buffer, pH 7.5, to a concentration of 2 mM. Allow for non-peptidic material in calculating the concentration. Peptides with free thiols are prone to dimerization. Handle in degassed buffers and react the thiol as soon as possible after dissolution. It is advisable to check the free thiol content before reaction. If the peptide does not dissolve, reduce the ionic strength of the buffer and/or the peptide concentration. Water may be used provided the resulting pH is in the range 6-8. Alternatively, co-solvent such as DMSO may be added.
2. Prepare a 10 mM solution of fluorescein-5-maleimide (Molecular Probes) in DMSO. Add one molar equivalent to the peptide and allow to react for 10 min. Because of uncertainties in the peptide and fluorescein-5-maleimide concentration, it is advisable to react, say, 0.75 equivalents of reagent, measure the thiol content and then add smaller reagent aliquots until the thiol is all reacted. The maleimido-thiol reaction is fast at these concentrations, but will require longer incubations at lower concentrations.
3. Measure the thiol content using Ellman's method: take 10 μl of the reaction, dilute to 1.0 ml in PBS (or above phosphate buffer) in a cuvette and zero the spectrophotometer. Add 20 μl of 2 mM DTNB and record the OD at 412 nm. This should be zero (check also unreacted peptide).
4. Prepare a 50 mM solution of quencher NHS ester in DMSO. Add to the fluoresceinylated peptide to a final concentration of 10 mM and react for 30 mm at room temperature.
5. Prepare a size-exclusion gel media column, e.g. Sephadex™ G10, of volume greater than 10 times the reaction volume in a disposable column. Equilibrate in 50 mM Tris-HCl, pH 7.5, or running buffer of choice. If insolubility problems have been encountered, there is a possibility of the product precipitating on the column. Experiment to find a suitable buffer: water may be a good choice.
6. Apply the reaction mixture to the column. Add buffer to elute and collect the first eluting colored band.
7. Run spectrum to confirm that peaks corresponding to both fluorescein (495 nm) and quencher are present. Analyze and purify by reverse-phase HPLC and characterize by mass spectrometry.

All publications, patents and patent applications mentioned in this specification are herein incorporated by reference to the same extent as if each individual publication, patent or patent application was specifically and individually indicated to be incorporated by reference.

The invention now having been fully described, it will be apparent to one of ordinary skill in the art that many changes and modifications can be made thereto without departing from the spirit or scope of the invention.

We claim:
1. A composition useful for synthesizing a quencher-labeled polynucleotide which has the structure (II):

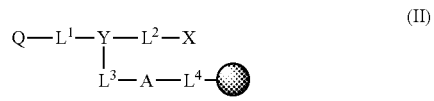

(II)

wherein:
Q is a quencher moiety Q1 having the following structure:

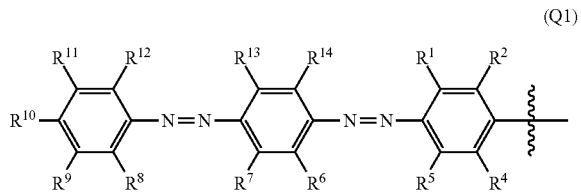

(Q1)

wherein:
R$^1$, R$^2$, R$^4$, R$^5$, R$^6$, R$^7$, R$^8$, R$^9$, R$^{10}$, R$^{11}$, R$^{12}$, R$^{13}$ and R$^{14}$ are each, independently of one another, selected from hydrogen, an electron-withdrawing group and an electron-donating group, or, alternatively R$^4$ may be taken together with R$^5$ or R$^6$ may be taken together with R$^7$ to form a benzo group, further wherein:
at least one of R$^1$, R$^2$, R$^4$, R$^5$, R$^6$, R$^7$, R$^8$, R$^9$, R$^{10}$, R$^{11}$, R$^{12}$, R$^{13}$ or R$^{14}$ is an electron-withdrawing group; and
at least one of R$^1$, R$^2$, R$^4$, R$^5$, R$^6$, R$^7$, R$^8$, R$^9$, R$^{10}$, R$^{11}$, R$^{12}$, R$^{13}$ or R$^{14}$ is an electron-donating group; and
a reactive linking group linking the aryl carbon of the quencher moiety to L$^1$, either directly or by way of a linker NR"R" moiety, where each R" is independently C$_1$-C$_{12}$ alkyl;
L$^1$, L$^3$ and L$^4$ are each, independently of one another, selected from a bond, C$_1$-C$_{12}$ alkyldiyl, C$_1$-C$_{12}$ alkoxyldiyl, C$_1$-C$_{12}$ alkylaminodiyl, C$_1$-C$_{12}$ alkylamidediyl, C$_5$-C$_{14}$ aryldiyl, and 1-20 ethyleneoxy units;
L$^2$ is a C$_1$-C$_{12}$ alkoxyldiyl, wherein the hydroxyl group is attached to X;
A is a cleavable linker;
X is an acid-labile protecting group;
Y is selected from N and CR, where R is selected from H, C$_1$-C$_6$ alkyl, and C$_5$-C$_{14}$ aryl; and

represents the solid support.

2. The composition of claim 1, wherein the electron-withdrawing groups are each, independently of one another, selected from $NO_2$, CN, $CF_3$, $CO_2H$, $CO_2R'$, $C(O)NH_2$, N(O)NHR', C(O)NR'R', CHO, C(O)R', $SO_2R'$, $SO_2CF_3$, $SO_2OR'$, $SO_3H$, NO and $C_5$-$C_{14}$ aryl, wherein each R' is independently H, $C_1$-$C_{12}$ alkyl or $C_5$-$C_{14}$ aryl.

3. The composition of claim 1, wherein the electron-donating groups are each, independently of one another, selected from $O^-$, $S^-$, NR"R", NHR", $NH_2$, NHC(O)R", OR", OH, OC(O)R", SR", SH, Br, I, Cl, F, R" and $C_5$-$C_{14}$ aryl, wherein each R" is independently H, $C_1$-$C_{12}$ alkyl or $C_5$-$C_{14}$ aryl.

4. The composition of claim 1, wherein $R^{10}$ is $NO_2$.

5. The composition of claim 1, wherein at least one of $R^1$, $R^2$, $R^3$, $R^4$, $R^5$, $R^6$, $R^7$, $R^8$, $R^9$, $R^{10}$, $R^{11}$, $R^{12}$, $R^{13}$ and $R^{14}$ is $OCH_3$.

6. The composition of claim 1, wherein the reactive linking group comprises an electrophile.

7. The composition of claim 6, wherein the electrophile of the reactive linking group is a carboxylic acid or an ester.

8. The composition of claim 1, wherein one R" is substituted $C_1$-$C_{12}$ alkyl and the other R" is unsubstituted $C_1$-$C_{12}$ alkyl.

9. The composition of claim 8, wherein the one R" that is unsubstituted $C_1$-$C_{12}$ alkyl is $CH_2CH_3$.

10. A compound having a structure of one of the following formulae:

Compound 30
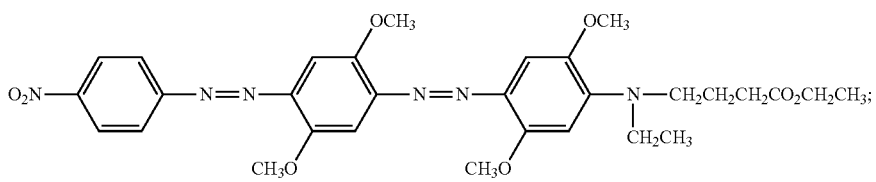

Compound 31
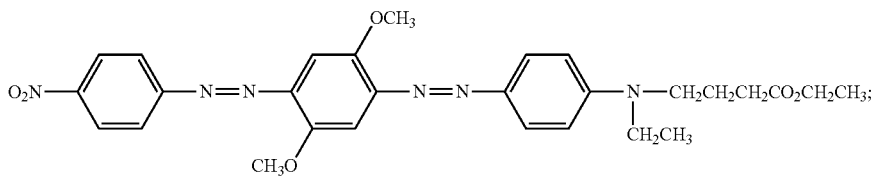

Compound 32
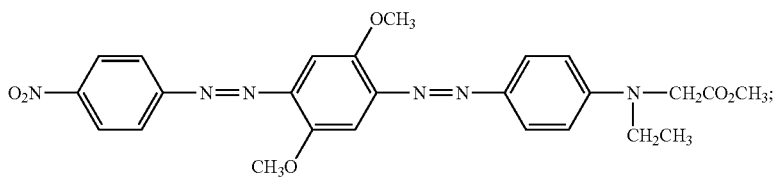

Compound 34
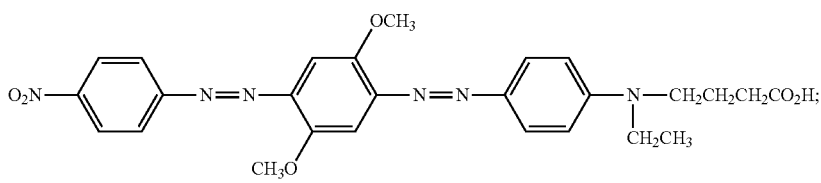

Compound 35
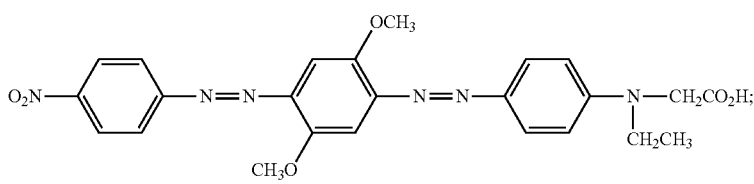

Compound 36
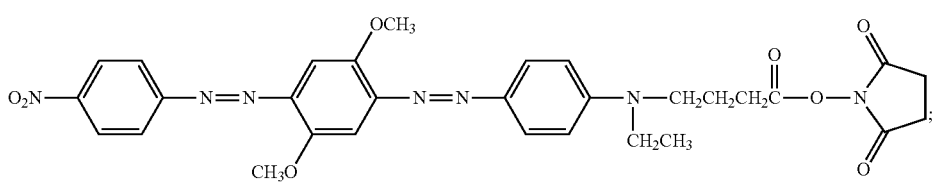

-continued
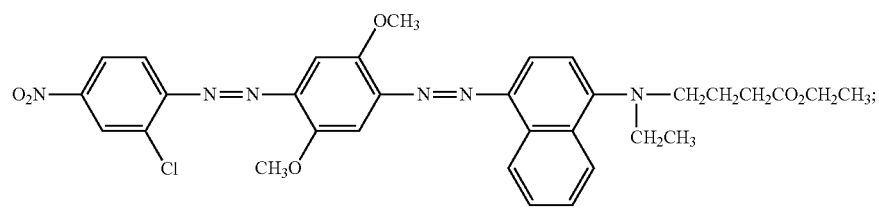
Compound 40
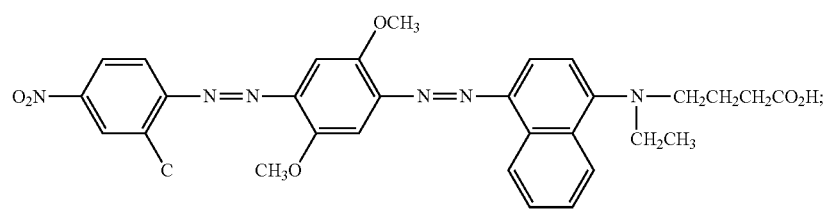
Compound 41
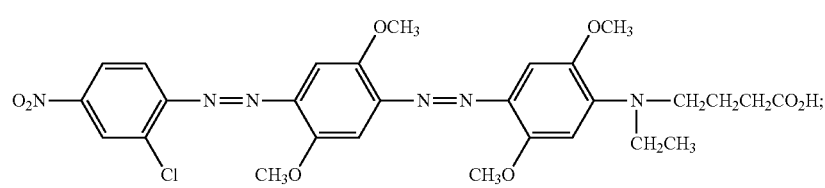
Compound 58
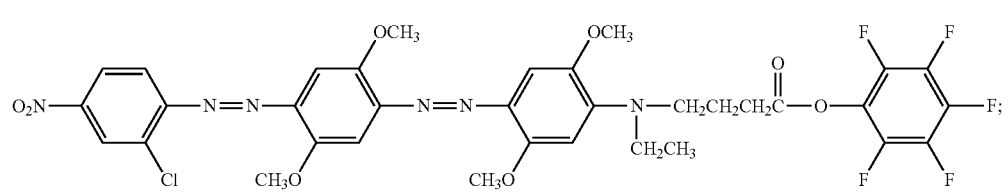
Compound 59
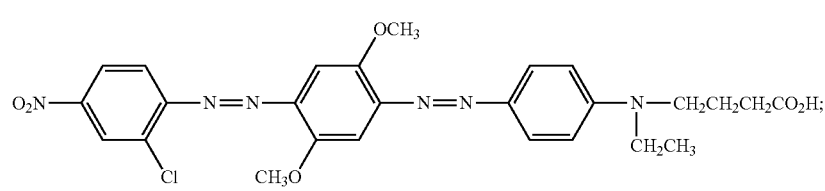
Compound 60
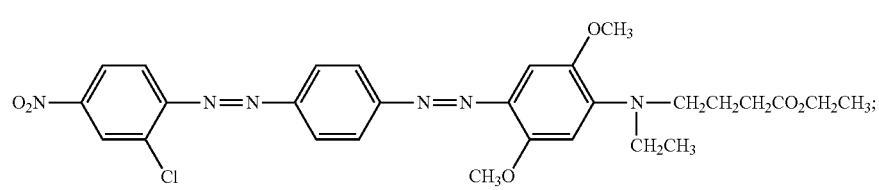
Compound 63
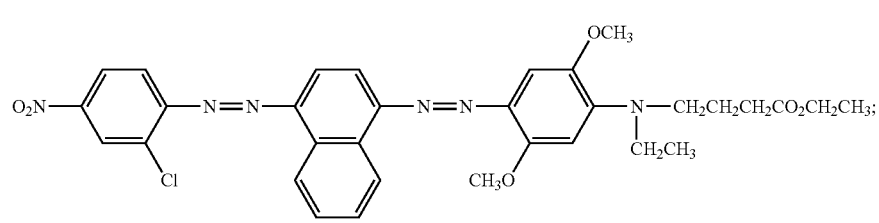
Compound 64
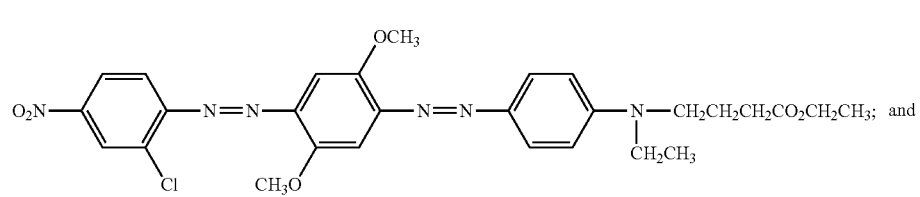
Compound 70

-continued

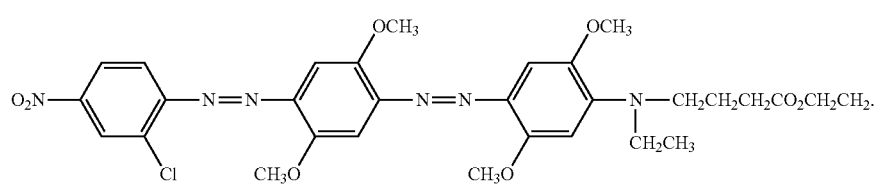

Compound 71

11. A compound having a structure of one of the following formulae:

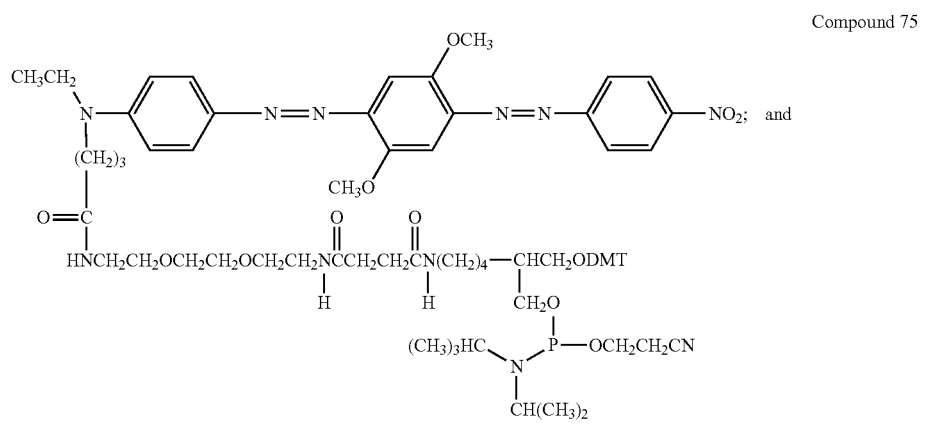

Compound 75

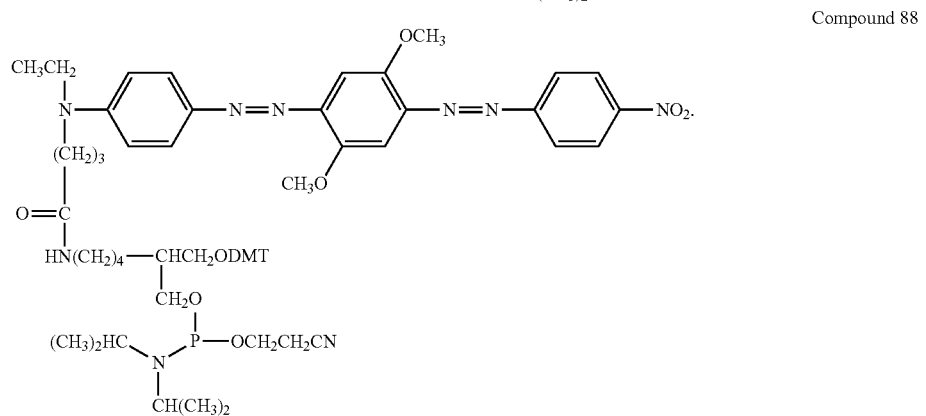

Compound 88

12. The composition of claim 1, wherein A is selected from;

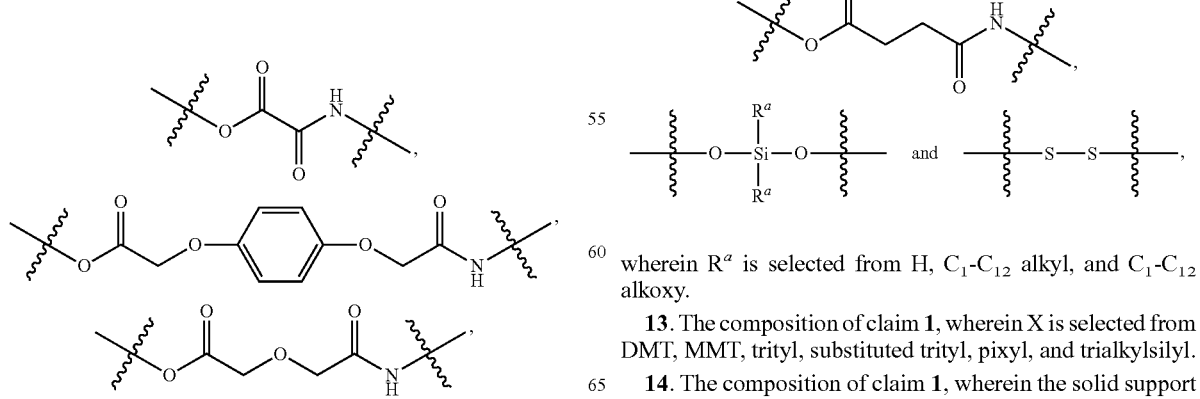

wherein $R^a$ is selected from H, $C_1$-$C_{12}$ alkyl, and $C_1$-$C_{12}$ alkoxy.

13. The composition of claim 1, wherein X is selected from DMT, MMT, trityl, substituted trityl, pixyl, and trialkylsilyl.

14. The composition of claim 1, wherein the solid support is selected from polystyrene, controlled-pore glass, silica gel, silica, polyacrylamide, polyacrylate, hydroxyethylmethycrylate, polyamide, polyethylene, polyethyleneoxy, and copolymers and grafts of such polymers.

15. A quencher-labeled conjugate, produced by reacting a phosphoramidite reagent of a nucleoside, a nucleotide or a polynucleotide with the alkoxydiyl $L^2$ moiety of the composition of claim 1, after removal of the acid labile X moiety of the composition.

16. The quencher-labeled conjugate of claim 15, wherein the conjugated substance is a polynucleotide comprising 2-100 nucleotides, and protected forms thereof.

17. The quencher-labeled conjugate of claim 16, further comprising a fluorescent moiety covalently attached to the polynucleotide, the fluorescence of which is capable of being quenched by the quencher moiety when the fluorescent and quencher moieties are in close proximity to one another.

18. A method of attaching a nucleotide to the composition of claim 1, comprising:
   removing the acid labile protecting group X from the composition thereby forming a deprotected composition;
   contacting the deprotected composition with a phosphoramidite nucleotide reagent, thereby forming a quencher labeled nucleotide.

19. A 3' quencher polynucleotide bound to a solid support, having the structure:

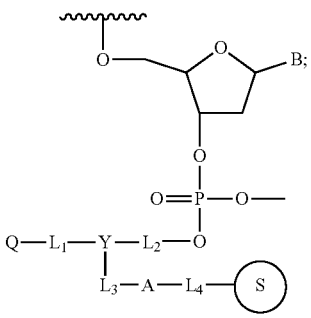

wherein the polynucleotide comprises 2 to 100 nucleotides;
Q is a quencher moiety Q1 having the following structure:

(Q1)

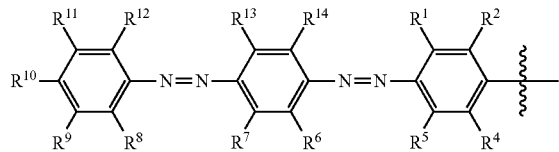

wherein:
$R^1, R^2, R^4, R^5, R^6, R^7, R^8, R^9, R^{10}, R^{11}, R^{12}, R^{13}$ and $R^{14}$ are each, independently of one another, selected from hydrogen, an electron-withdrawing group and an electron-donating group, or, alternatively $R^4$ may be taken together with $R^5$ or $R^6$ may be taken together with $R^7$ to form a benzo group, further wherein:
   at least one of $R^1, R^2, R^4, R^5, R^6, R^7, R^8, R^9, R^{10}, R^{11}, R^{12}, R^{13}$ or $R^{14}$ is an electron withdrawing group; and
   at least one of $R^1, R^2, R^4, R^5, R^6, R^7, R^8, R^9, R^{10}, R^{11}, R^{12}, R^{13}$ or $R^{14}$ is an electron donating group; and
a reactive linking group linking the aryl carbon of the quencher moiety to $L^1$, either directly or by way of a linker NR"R" moiety, where each R" is independently $C_1$-$C_{12}$ alkyl;

$L^1, L^3$ and $L^4$ are each, independently of one another, selected from a bond, $C_1$-$C_{12}$ alkyldiyl, $C_1$-$C_{12}$ alkoxyldiyl, $C_1$-$C_{12}$ alkylaminodiyl, $C_1$-$C_{12}$ alkylamidediyl, $C_5$-$C_{14}$ aryldiyl, and 1-20 ethyleneoxy units;
$L^2$ is a $C_1$-$C_{12}$ alkoxyldiyl, wherein the hydroxyl group is attached to a phosphodiester moiety of a first nucleotide;
A is a cleavable linker;
Y is selected from N and CR, where R is selected from H, $C_1$-$C_6$ alkyl, and $C_5$-$C_{14}$ aryl; and represents the solid support.

20. The 3' quencher polynucleotide of claim 19, wherein A is selected from;

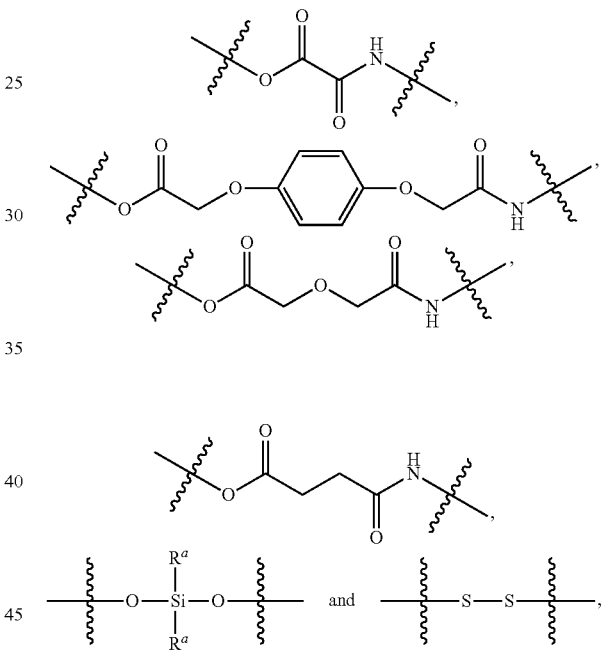

wherein $R^a$ is selected from H, $C_1$-$C_{12}$ alkyl, and $C_1$-$C_{12}$ alkoxy.

21. The 3' quencher polynucleotide of claim 19, wherein the electron-withdrawing groups are each, independently of one another, selected from $NO_2$, CN, $CF_3$, $CO_2H$, $CO_2R'$, $C(O)NH_2$, $N(O)NHR'$, $C(O)NR'R'$, CHO, $C(O)R'$, $SO_2R'$, $SO_2CF_3$, $SO_2OR'$, $SO_3H$, NO and $C_5$-$C_{14}$ aryl, wherein each R' is independently H, $C_1$-$C_{12}$ alkyl or $C_5$-$C_{14}$ aryl.

22. The 3' quencher polynucleotide of claim 19, wherein the electron-donating groups are each, independently of one another, selected from $O^-$, $S^-$, NR"R", NHR", $NH_2$, NHC(O)R", OR", OH, OC(O)R", SR", SH, Br, I, Cl, F, R'" and $C_5$-$C_{14}$ aryl, wherein each R'" is independently H, $C_1$-$C_{12}$ alkyl or $C_5$-$C_{14}$ aryl.

23. The 3' quencher polynucleotide of claim 19, wherein the reactive linking group comprises an electrophile.

24. The 3' quencher polynucleotide of claim 19, further comprising a fluorescent dye label.

25. A 5' quencher polynucleotide bound to a solid support, having the structure:

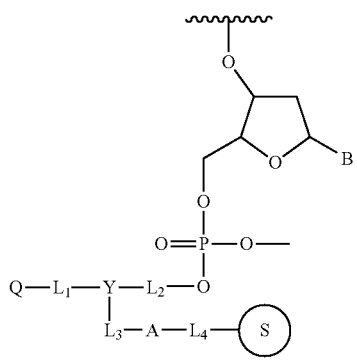

wherein the polynucleotide comprises 2 to 100 nucleotides;
Q is a quencher moiety Q1 having the following structure:

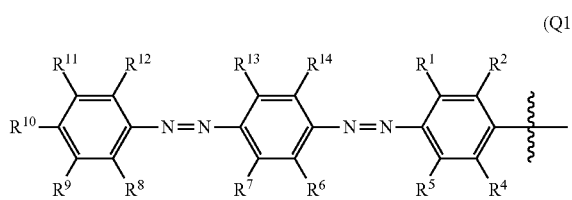

(Q1)

wherein:
$R^1, R^2, R^4, R^5, R^6, R^7, R^8, R^9, R^{10}, R^{11}, R^{12}, R^{13}$ and $R^{14}$ are each, independently of one another selected from hydrogen, an electron-withdrawing group and an electron-donating group, or, alternatively $R^4$ may be taken together with $R^5$ or $R^6$ may be taken together with $R^7$ to form a benzo group, further wherein:
at least one of $R^1, R^2, R^4, R^5, R^6, R^7, R^8, R^9, R^{10}, R^{11}, R^{12}, R^{13}$ or $R^{14}$ is an electron withdrawing group; and
at least one of $R^1, R^2, R^4, R^5, R^6, R^7, R^8, R^9, R^{10}, R^{11}, R^{12}, R^{13}$ or $R^{14}$ is an electron donating group; and
a reactive linking group linking the aryl carbon of the quencher moiety to $L^1$, either directly or by way of a linker NR"R" moiety, where each R" is independently $C_1$-$C_{12}$ alkyl;
$L^1, L^3$ and $L^4$ are each, independently of one another, selected from a bond, $C_1$-$C_{12}$ alkyldiyl, $C_1$-$C_{12}$ alkoxyldiyl, $C_1$-$C_{12}$ alkylaminodiyl, $C_1$-$C_{12}$ alkylamidediyl, $C_5$-$C_{14}$ aryldiyl, and 1-20 ethyleneoxy units;
$L^2$ is a $C_1$-$C_{12}$ alkoxyldiyl, wherein the hydroxyl group is attached to a phosphodiester moiety of a first nucleotide;
A is a cleavable linker;
Y is selected from N and CR, where R is selected from H, $C_1$-$C_6$ alkyl, and $C_5$-$C_{14}$ aryl; and

represents the solid support.

26. The 5' quencher polynucleotide of claim 25, wherein A is selected from;

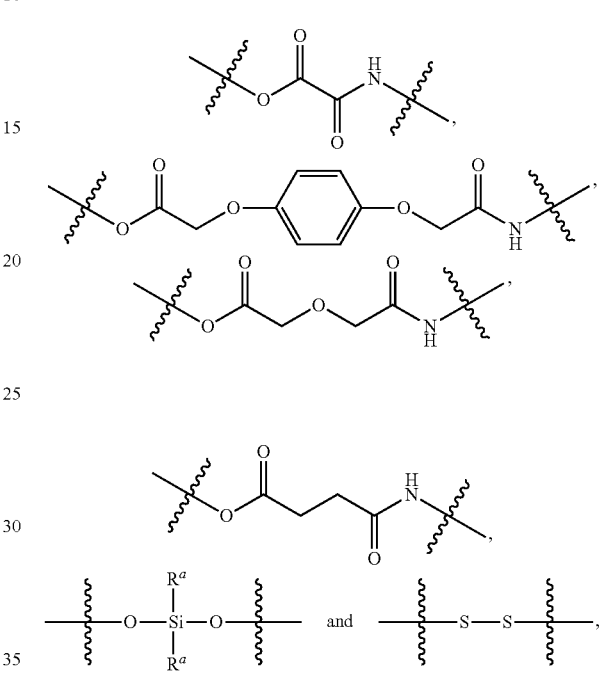

wherein $R^a$ is selected from H, $C_1$-$C_{12}$ alkyl, and $C_1$-$C_{12}$ alkoxy.

27. The 5' quencher polynucleotide of claim 25, wherein the electron-withdrawing groups are each, independently of one another, selected from $NO_2$, CN, $CF_3$, $CO_2H$, $CO_2R'$, $C(O)NH_2$, N(O)NHR', C(O)NR'R', CHO, C(O)R', $SO_2R'$, $SO_2CF_3$, $SO_2OR'$, $SO_3H$, NO and $C_5$-$C_{14}$ aryl, wherein each R' is independently H, $C_1$-$C_{12}$ alkyl or $C_5$-$C_{14}$ aryl.

28. The 5' quencher polynucleotide of claim 25, wherein the electron-donating groups are each, independently of one another, selected from O⁻, S⁻, NR"R", NHR", $NH_2$, NHC(O)R", OR", OH, OC(O)R", SR", SH, Br, I, Cl, F, R" and $C_5$-$C_{14}$ aryl, wherein each R" is independently H, $C_1$-$C_{12}$ alkyl or $C_5$-$C_{14}$ aryl.

29. The 5' quencher polynucleotide of claim 25, wherein the reactive linking group comprises an electrophile.

* * * * *

UNITED STATES PATENT AND TRADEMARK OFFICE
CERTIFICATE OF CORRECTION

PATENT NO. : 8,637,658 B2
APPLICATION NO. : 13/629021
DATED : January 28, 2014
INVENTOR(S) : Gregory Ewing et al.

Page 1 of 1

It is certified that error appears in the above-identified patent and that said Letters Patent is hereby corrected as shown below:

- Claim 5, Column 74, Line 5: "$R^2, R^3, R^4, R^5, R^6, R^7, R^8, R^9, R^{10}, R^{11}, R^{12}, R^{13}$ and $R^{14}$ is," should read -- $R^2, R^4, R^5, R^6, R^7, R^8, R^9, R^{10}, R^{11}, R^{12}, R^{13}$ and $R^{14}$ is, --

- Claim 10, Column 75, Lines 15-20:

"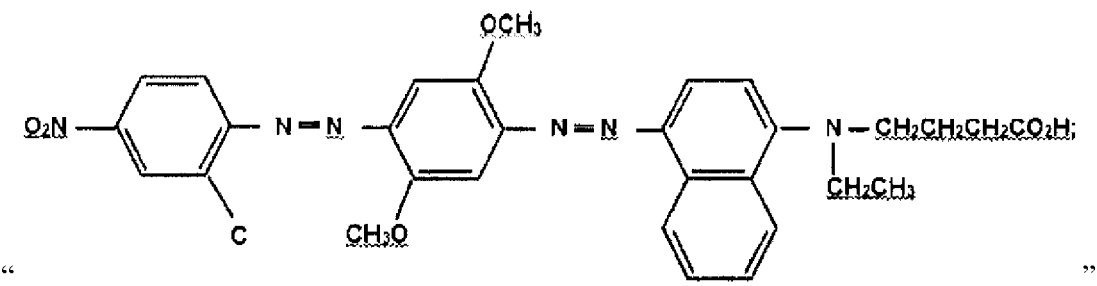"

should read

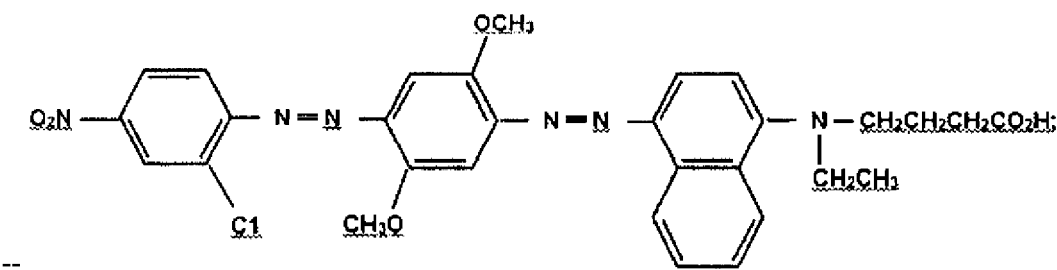
--

- Claim 19, Column 80, Lines 12-16: " 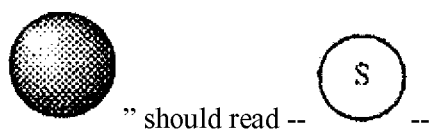 " should read -- Ⓢ --

- Claim 25, Column 82, Lines 1-5: " " should read -- Ⓢ --

Signed and Sealed this
Nineteenth Day of April, 2016

Michelle K. Lee
*Director of the United States Patent and Trademark Office*